US009650440B2

(12) United States Patent
Grasso et al.

(10) Patent No.: US 9,650,440 B2
(45) Date of Patent: May 16, 2017

(54) MONOCLONAL ANTIBODIES THAT SPECIFICALLY BLOCK BIOLOGICAL ACTIVITY OF A TUMOR ANTIGEN

(71) Applicant: Morphotek, Inc., Exton, PA (US)

(72) Inventors: Luigi Grasso, Bryn Mawr, PA (US); Nicholas C. Nicolaides, Garnett Valley, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 398 days.

(21) Appl. No.: 13/826,964

(22) Filed: Mar. 14, 2013

(65) Prior Publication Data

US 2013/0189272 A1    Jul. 25, 2013

Related U.S. Application Data

(60) Continuation of application No. 12/500,144, filed on Jul. 9, 2009, which is a division of application No. 11/056,776, filed on Feb. 11, 2005, now abandoned.

(60) Provisional application No. 60/544,364, filed on Feb. 12, 2004.

(51) Int. Cl.
| | |
|---|---|
| *A61K 39/395* | (2006.01) |
| *C07K 16/18* | (2006.01) |
| *C07K 16/28* | (2006.01) |
| *C07K 16/30* | (2006.01) |
| *A61K 39/00* | (2006.01) |

(52) U.S. Cl.
CPC ............. *C07K 16/28* (2013.01); *C07K 16/30* (2013.01); *C07K 16/3069* (2013.01); *A61K 2039/505* (2013.01); *C07K 2317/24* (2013.01); *C07K 2317/56* (2013.01); *C07K 2317/732* (2013.01); *C07K 2317/92* (2013.01)

(58) Field of Classification Search
CPC ............. A61K 39/395; A61K 39/3955; A61K 39/39558; C07K 16/18; C07K 16/28; C07K 16/2863; C07K 16/30; C07K 16/3069
See application file for complete search history.

(56) References Cited

U.S. PATENT DOCUMENTS

| | | | |
|---|---|---|---|
| 4,694,778 A | 9/1987 | Learn et al. | |
| 4,851,332 A | 7/1989 | Rettig et al. | |
| 5,006,470 A | 4/1991 | Yamaguchi et al. | |
| 5,108,921 A | 4/1992 | Low et al. | |
| 5,320,956 A | 6/1994 | Willingham et al. | |
| 5,416,016 A | 5/1995 | Low et al. | |
| 5,525,337 A | 6/1996 | Willingham et al. | |
| 5,646,253 A | 7/1997 | Wallace et al. | |
| 5,688,488 A | 11/1997 | Low et al. | |
| 5,789,650 A | 8/1998 | Lonberg et al. | |
| 5,798,230 A | 8/1998 | Pornkamm et al. | |
| 5,817,313 A | 10/1998 | Willingham et al. | |
| 5,820,847 A | 10/1998 | Low et al. | |
| 5,952,484 A | 9/1999 | Wallace et al. | |
| 6,083,502 A | 7/2000 | Pastan et al. | |
| 6,124,106 A | 9/2000 | Wallace et al. | |
| 6,146,894 A | 11/2000 | Nicolaides et al. | |
| 6,153,430 A | 11/2000 | Pastan et al. | |
| 6,191,268 B1 | 2/2001 | Liskay et al. | |
| 6,261,535 B1 | 7/2001 | Thorpe et al. | |
| 6,348,195 B1 | 2/2002 | Wallace et al. | |
| 6,365,410 B1 | 4/2002 | Schellenberger et al. | |
| 6,602,688 B1 | 8/2003 | Opper et al. | |
| 6,808,894 B1 | 10/2004 | Nicolaides et al. | |
| 6,809,184 B1 | 10/2004 | Pastan et al. | |
| 7,081,518 B1 | 7/2006 | Pastan et al. | |
| 7,807,804 B2 | 10/2010 | Sinacore et al. | |
| 2002/0192157 A1 | 12/2002 | Low et al. | |
| 2003/0027177 A1 | 2/2003 | Haseltine et al. | |
| 2004/0235108 A1 | 11/2004 | Grasso et al. | |
| 2005/0054048 A1 | 3/2005 | Grasso et al. | |
| 2005/0232919 A1 | 10/2005 | Grasso et al. | |
| 2006/0204506 A1 | 9/2006 | Ebel et al. | |
| 2006/0239910 A1 | 10/2006 | Nicolaides et al. | |
| 2008/0254499 A1 | 10/2008 | Low et al. | |

(Continued)

FOREIGN PATENT DOCUMENTS

| | | |
|---|---|---|
| EP | 0 197 435 B1 | 7/1992 |
| EP | 0 239 400 B1 | 8/1994 |

(Continued)

OTHER PUBLICATIONS

Ellison, J.W., et al. Nucleic Acids Research, 10(13): 4071-4079, 1982.*
Titani, K., et al., The Journal of Biological Chemistry, 244(13): 3550-35560, 1969.*
Armstrong et al., "Exploratory Phase 2 Efficacy Study of MORAb-003, a Monoclonal Antibody against Folate Receptor Alpha, in Platinum-Sensitive Epithelial Ovarian Cancer in First Relapse," Sep. 23, 2009, 24 pages.

(Continued)

*Primary Examiner* — Misook Yu
*Assistant Examiner* — Anne Holleran
(74) *Attorney, Agent, or Firm* — Baker & Hostetler LLP

(57) ABSTRACT

This invention relates to novel monoclonal antibodies that specifically bind to the alpha-folate receptor. In some embodiments, the antibodies inhibit a biological activity of folate receptor-α (FR-α). The antibodies are useful in the treatment of certain cancers, particularly cancers that have increased cell surface expression of the alpha-folate receptor ("FR-α"), such as ovarian, breast, renal, colorectal, lung, endometrial, or brain cancer. The invention also relates to cells expressing the monoclonal antibodies, antibody derivatives, such as chimeric and humanized monoclonal antibodies, antibody fragments, and methods of detecting and treating cancer using the antibodies, derivatives, and fragments.

16 Claims, 5 Drawing Sheets

(56) References Cited

U.S. PATENT DOCUMENTS

| | | |
|---|---|---|
| 2008/0312093 A1 | 12/2008 | Inazawa et al. |
| 2009/0081710 A1 | 3/2009 | Low et al. |
| 2009/0087849 A1 | 4/2009 | Malinowski et al. |
| 2009/0274697 A1 | 11/2009 | Grasso |
| 2009/0324594 A1 | 12/2009 | Nicolaides et al. |
| 2010/0055034 A1 | 3/2010 | Martin et al. |
| 2010/0055735 A1 | 3/2010 | Low et al. |

FOREIGN PATENT DOCUMENTS

| | | |
|---|---|---|
| EP | 1 258 255 A1 | 11/2002 |
| WO | WO 90/07861 A1 | 7/1990 |
| WO | WO 92/07081 A2 | 4/1992 |
| WO | WO 95/24482 A1 | 9/1995 |
| WO | WO 97/25068 A3 | 7/1997 |
| WO | WO 97/42329 A1 | 11/1997 |
| WO | WO 00/73346 A1 | 12/2000 |
| WO | WO 02/37967 A1 | 5/2002 |
| WO | WO 02/054856 A1 | 7/2002 |
| WO | WO 02/094879 A1 | 11/2002 |
| WO | WO 03/084469 | 10/2003 |
| WO | WO 2004/009782 A2 | 1/2004 |
| WO | WO 2004/113388 A2 | 12/2004 |
| WO | WO 2005/011735 | 2/2005 |
| WO | WO 2005/014652 A1 | 2/2005 |
| WO | WO 2005/080431 A2 | 9/2005 |
| WO | WO 2006/116592 A2 | 11/2006 |
| WO | WO 2009/002993 | 12/2008 |
| WO | WO 2009/081275 | 7/2009 |
| WO | WO 2009/132081 | 10/2009 |

OTHER PUBLICATIONS

Armstrong et al., "Efficacy and Safety of Farletuzumab, a Humanized Monoclonal Antibody to Folate Receptor Alpha, in Platinum-Sensitive Relapsed Ovarian Cancer Subjects: Preliminary Data From a Phase-2 Study," Joint ECCO 15-34[1] ESMO Multidisciplinary Congress, Berlin, Sep. 20-24, 2009, 2 pages, Abstract 0-8000.

Armstrong et al., "Exploratory Phase II Efficacy Study of MORAb-003, A Monoclonal Antibody Against Folate Receptor Alpha, In Platinum-Sensitive Ovarian Cancer in First Relapse", 2008 ASCO Annual Meeting, J. Clinical Oncology, 26, 2008, (May 20 suppl; abstract 5500), 2 pages.

Ausubel, et al., Current Protocols in Molecular Biology, John Wiley & Sons, New York, 1998.

Bolen et al., "The Src Family of Tyrosine Protein Kinases in Hemopoietic Signal Transduction", FASEB J., Dec. 1992, 6(15), 3403-3409.

Chatterjee et al., "GPI Anchoring Leads to Sphingolipid-Dependent Retention of Endocytosed Proteins in the Recycling Endosomal Compartment", The EMBO Journal, Feb. 2001, 20(7), 1583-1592.

Dennis, C., "Cancer: Off by a whisker", Nature, Aug. 17, 2006, 442(7104), 739-741.

Elit et al., "A Randomized, Double-Blind, Placebo-Controlled Phase II Study of the Efficacy and Safety of Farletuzumab (MORAb-003) in Combination With Weekly Paclitaxel in Subjects With Platinum-Resistant or Refractory Relapsed Ovarian Cancer", 2010 ASCO Annual Meeting, J. Clinical Oncology, 28, 15s, 2010, (suppl; abstr TPS255), 2 pages.

Goldenberg-Furmanov et al., "Lyn Is a Target Gene for Prostate Cancer: Sequence-Based Inhibition Induces Regression of Human Tumor Xenografts", Cancer Research, Feb. 1, 2004, 64(3), 1058-1066.

Helms et al., "Lipids as Targeting Signals: Lipid Rafts and Intracellular Trafficking", Traffic, Apr. 2004, 5(4), 247-254.

Ingley, "Src Family Kinases: Regulation of Their Activities, levels and Identification of New Pathways", BBA, Jan. 2008, 1784(1), 56-65.

Nahta et al., "Growth Factor Receptors in Breast Cancer: Potential for Therapeutic Intervention", Oncologist, Feb. 2003, 8(1), 5-17.

Parsons et al., "Src Family Kinases, Key Regulators of Signal Transduction", Oncogene, Oct. 28, 2004, 23(48), 7906-7909.

Suzuki et al., "GPI-anchored Receptor Clusters Transiently Recruit Lyn and Ga for Temporary Cluster immobilization and Lyn Activation: Single-Molecule Tracking Study 1", JCB Article, May 21, 2007, 177(4), 717-730.

Wu et al., "Expression of Folate Receptor Type a in Relation to Cell Type, Malignancy, and Differentiation in Ovary, Uterus, and Cervix", Cancer Epidemiology, Biomarkers and Prevention, Sep. 1999, 8(9), 775-782.

Ozols et al., "Systemic therapy for ovarian cancer: current status and new treatments", Seminars in Oncology, Apr. 2006, 33(2 Suppl 6), S3-S11.

Ozols et al., "No Title", Seminars in Oncology, Apr. 2006, 33(2 Suppl 6), S1-S2.

ATCC website search output for PTA-7552.

Fundamental Immunology 242, William E. Paul, M.D., ed., 3rd ed. 1993.

Huang, X., et al., "On global sequence alignment", CABIOS, Jun. 1994, 10(3), 227-235.

Jemal et al. "Cancer statistics 2008", CA Cancer J Clin, Mar.-Apr. 2008, 58, 71-96.

Presta, L. G., "Antibody engineering", Curr. Op. Biotechnol., Aug. 1992, 3(4), 394-398.

Sandhu, "Protein engineering of antibodies", Grit Rev. Biotechnol., 1992, 12(5-6):437-62.

"FY2009 Product Creation Meeting, Dramatic Leap Plan 2011", Eisai Co., Ltd., Power Point Presentation, 121 pages, Dec. 18, 2009.

Alberti, S., et al., "The CA-MOv18 molecule, a cell-surface marker of human ovarian carcinomas, is anchored to the cell membrane by phosphatidylinositol", Biochem. & Biophys. Res. Commun., Sep. 28, 1990, 171(3), 1051-1055.

Alsmadi, O., et al., "Antibody-dependent cellular cytotoxicity directed against cells expressing human immunodeficiency virus type I envelope of primary or laboratory-adapted strains by human and chimpanzee monoclonal antibodies of different epitope specificities", J. of Viral., Jan. 1998, 72(1), 286-293.

Andersson, H., et al., "Comparision of the therapeutic efficacy of211At- and 1311-Labelled monoclonal antibody MOv18 in nude mice with intraperitoneal growth of human ovarian cancer", Anticancer Res., Jan.-Feb. 2001, 21(1A), 409-412.

Backus, H.H.J., et al., "Folate depletion increases sensitivity of solid tumor cell lines to 5-fluorouracil and antifolates", Int. J. of Cancer, Sep. 15, 2000, 87(6), 771-778.

Balint, R.F., et al., "Antibody engineering by parsimonious mutagenesis", Gene, Dec. 27, 1993, 137(1), 109-118.

Beckman et al., "Antibody Constructs in Cancer Therapy", Cancer, 109(2), Jan. 15, 2007, 170-179.

Beii-McGuinn et al., "A Phase 1 Study of MORAb-003, a Fully Humanized Monoclonal Antibody against Folate Receptor Alpha, in Advanced Epithelial Ovarian Cancer", J Clin Oneal May 20, 2008, 26 (15S), ASCO abstract 5517.

Beii-McGuinn et al., "A Phase 1 Study of MORAb-003, a Fully Humanized Monoclonal Antibody against Folate Receptor Alpha, in Advanced Epithelial Ovarian Cancer", J Clin Oneal, May 20, 2008, 26, suppl, ASCO abstract 5500.

Beii-McGuinn et al., "A Phase 1 Study of MORAb-003, a Fully Humanized Monoclonal Antibody against Folate Receptor Alpha, in Advanced Epithelial Ovarian Cancer", Jun. 20, 2007, ASCO Annual Meeting Proceedings Part I. vol. 25, No. 18S, ASCO abstract 5553.

Beii-McGuinn et al., "A Phase 1 Study of MORAb-003, a Fully Humanized Monoclonal Antibody against Folate Receptor Alpha, in Advanced Epithelial Ovarian Cancer", Jun. 20, 2007, ASCO Annual Meeting Proceedings Part I. vol. 25, No. 18S, ASCO abstract 5583.

Bird, R.E., "Single-chain antigen-binding proteins", Science, Oct. 21, 1988, 242(4877), 423-442.

Boerman et al., "Comparative immunohistochemical study of four monoclonal antibodies directed against ovarian carcinoma-associated antigens", Int J Gynecol Pathoi, 1991, 10(1), 15-25.

Boerner, P., et al., "Production of antigen-specific human monoclonal antibodies from in vitro-primed human splenocytes", J. of Immunol., Jul. 1, 1991, 147(1), 86-95.

(56) References Cited

OTHER PUBLICATIONS

Bottero et al., "Gene transfection and expression of the ovarian carcinoma marker folate binding protein on NIH/3T3 cells increases cell growth in vitro and in vivo", Cancer Res, 1993, 53, 5791-5796.
Bowie et al, "Deciphering the message in protein sequences: tolerance to amino acid substitutions", Science, Mar. 16, 1990, 247(4948), 1306-1310.
Buist et al., "Tumor uptake of intravenously administered radiolabeled antibodies in ovarian carcinoma patients in relation to antigen expression and other tumor characteristics", Int J Cancer, Apr. 21, 1995, 64(2), 92-98.
Bukowski et al., "The management of recurrent ovarian cancer", Semin Oneal., 2007, 34(2 Suppl 2), S1-15.
Campbell, I.G., et al., "Folate-binding protein is a marker for ovarian cancer", Cancer Res., Oct. 1, 1991, 51(19), 5329-5338.
Cao, D., et al., "Expression of novel markers of pancreatic ductal adenocarcinoma in pancreatic nonductal neoplasms: additional evidence of different genetic pathways", Mod. Pathol., Jun. 2005, 18(6), 752-761.
Casalini, P. et al., "Use of combination of monoclonal antibodies directed against three distinct epitopes of a tumor-associated antigen: Analysis of cell binding and internalization", Int. J. Cancer, May 10, 1991, 48(2), 284-290.
Cespedes et al., 'Mouse models in oncogenisis and cancer therapy', Clin. Transl. Oneal., May 2006, (8)5, 318-329.
Chang, K., et al., "Monoclonal antibody K1 reacts with epithelial mesothelioma but not with lung adenocarcinoma", Am J. of Surgical Pathology, Mar. 1992, 16(3), 259-268.
Clynes R.A., et al., "Inhibitory Fc receptors modulate in vivo cytoxicity against tumor targets", Nat. Med., Apr. 2000, 6(4), 443-446.
Clynes, R., et al., "Fc receptors are required in passive and active immunity to melanoma", Proc. Natl. Acad. Sci. USA, Jan. 20, 1998, 95(2), 652-656.
Cogliati, T. et al., "Preparation and biological characterization of conjugates consisting of ricin and a tumor-specific non-internalizing MAb", Anticancer Res., Jan.-Feb. 1991, 11(1), 417-421.
Cole, S. P. C. et al., "The EBV-hybridoma technique and its application to human lung cancer", Monoclonal Antibodies and Cancer Therapy (vol. 27, UCLA Symposia on Molecular and Cellular Biology, New Series) (eds. R.A. Reisfeld and S.Sell), 1985, 77-96.
Coleman et al., Farletuzumab, a Novel Monoclonal Antibody Against Folate Receptor-a, Exhibits Clinical Efficacy in Platinum-Snesitive 1st Relapse of Ovarian Cancer Subjects, ESGO Slide presentation poster, Oct. 13, 2009.
Coliva, et al., Cancer Immunol. Immunother., Dec. 2005, Epub: May 31, 2005, 54(12), 1200-1213 (Abstract).
Coney, L.R., et al., "Chimeric murine-human antibodies directed against folate binding receptor are efficient mediators of ovarian carcinoma cell killing", Cancer Res., May 1, 1994, 54(9), 2448-2455.
Coney, L.R., et al., "Cloning of a tumor-associated antigen: MOV18 and MOV19 antibodies recognize a folate-binding protein", Cancer Res., Nov. 15, 1991, 51(22), 6125-6132.
Correa, "Tumor Targeting in Cancer Therapy: Internalization of Antibodies", Humana Press, Totowa, NJ, 21, 391-409.
Ebel, W. et al., "Preclinical evaluation of MORAb-003, a humanized monoclonal antibody antagonizing folate receptor-alpha", Cancer Immun., Mar. 9, 2007, 7:6.
Elwood, P. C., "Molecular Cloning and Characterization of the Human Folate-binding Protein eDNA from Placenta and Malignant Tissue Culture (KB) Cells", J. Bioi. Chem., Sep. 5, 1989, 264(25), 14893-14901.
Elwood, P.C., et al., "The divergent 5' termini of the a human folate receptor (hFR) mRNAs originate from two tissue-specific promoters and alternative splicing: characterization of the a hFR gene structure", Biochemistry, Feb. 11, 1997, 36(6), 1467-1478.
European Patent Application No. 05722917.1: Examination Report dated Jun. 18, 2012,8 pages.

Franklin, W.A., et al., "New anti-lung-cancer antibody cluster 12 reacts with human folate receptors present on adenocarcinoma", Int. J. Cancer, 1994, Suppl. 8, 89-95.
Frigerio, L., et al., "Assembly, secretion, and vacuolar delivery of a hybrid immunoglobulin in plants", Plant Physiol., Aug. 2000, 123(4), 1483-1493.
Fujimori et al., "A Modeling Analysis of Monoclonal Antibody Percolation Through Tumors: A Binding-Site Barrier", J Nuclear Med, 31(7), Jul. 1990,1191-1198.
Galmozzi, E., et al., "Exon 3 of the a folate receptor gene contains a 5' splice site which confers enhanced ovarian carcinoma specific expression", FEBS Letters, Jul. 27, 2001, 502(1-2), 31-34.
Garcia, A.A., "Salvage therapy for ovarian cancer", Curr. Oneal. Rep., Sep. 1999, 1(1), 64-70.
Garin-Chesa, P., et al., "Trophoblast and ovarian cancer antigen LK26", Am. J. of Pathol., Feb. 1993, 142(2), 557-567.
Garmestani, K. et al., "Synthesis and evaluation of a macrocyclic bifunctional chelating agent for use with bismuth radionuclides", Nucl. Med. Bioi., May 2001, 28(4), 409-418.
Gruner, B.A., et al., "The folate receptor as a potential therapeutic anticancer target", Investigational New Drugs, 1999, 205-219.
Gussow et al., "Humanization of monoclonal antibodies", Methods in Enzymology, 1991, 203, 99-121.
Hanlon, M.H., et al., "In vitro uptake, anabolism, and cellular retention of 1843U89 and other benzoquinazoline inhibitors ofthymidylate synthase", Cancer Res., Jul. 15, 1996, 56(14), 3301-3306.
Harkins, K.R., "Antibody purification methods", Basic Methods in Antibody Production and Characterization, CRC Press, Howard, G.C., et al. (Eds.), 2000, Chapter 11, 141-168.
Hassan, R., "Targeted therapy of mesothelin expressing mesotheliomas (MM), ovarian cancer (OC) and pancreatic cancer (PC)", J. of Clinical Oncology, 2004, p. 3035 (Abstract).
Hassan, R., et al., "Anti-tumor activity of K1-LysPE38QR, an immunotoxin targeting mesothelin, a cell-surface antigen overexpressed in ovarian cancer and malignant mesothelioma", J. of Immunotherapy, Jul.-Aug. 2000, 23(4), 473-479.
Hassan, R., et al., "Antitumor activity of SS(dsFv)PE38 and SS1(dsFv)PE38, recombinant antimesothelin immunotoxins against human gynecologic cancers grown in organotypic culture in vitro", Clin. Cancer Res., Nov. 2002, 8(11), 3520-3526.
Hassan, R., et al., "Mesothelin: a new target for immunotherapy", Clin. Cancer Res., Jun. 15, 2004, 10(12 pt. 1), 3937-3942.
Hassan, R., et al., "SS1(dsFv)-PE38 anti-mesothelin immunotoxin in advanced malignancies: phase I and pharmacokinetic studies of alternate-day infusion", Proc. Am. Soc. Clin. Oneal., 2002, Abstract No. 113, downloaded from the Internet on Oct. 20, 2005, 2 pages.
Holm, J., et al., "Characterization of a high-affinity folate receptor in normal and malignant human testicular tissue", Bioscience Reports, Dec. 1999, 19(6), 571-580.
Holm, J., et al., "Folate receptor of human mammary adenocarcinoma", APMIS, Jun. 1994, 102(6), 413-419.
Holm, J., et al., "Folate receptors in malignant and benign tissues of human female genital tract", Biosci. Reports, Aug. 1997, 17(4), 415-427.
Hough, C.D., et al., "Coordinately up-regulated genes in ovarian cancer", Cancer Res., May 15, 2001, 61(10), 3869-3876.
Houghton, A.N., et al., "Monoclonal antibodies: potential applications to the treatment of cancer", Seminars in Oncology, Jun. 1986, 13(2), 165-179.
Howard, G.C., et al. (Eds.), "Antibody Purification Methods", Basic Methods in Antibody Production and Characterization, CRC Press, 2000, Chapter 11, 142-168.
Huang, C., et al., "Construction of representative immunoglobulin variable region eDNA libraries from human peripheral blood lymphocytes without in vitro stimulation", J. of Immunol. Methods, 1991, 141,227-236.
Hudson, P.J., "Recombinant antibody constructs in cancer therapy", Curr. Opin. Immunol., Oct. 1999, 11(5), 548-557.
Huston, J.S., et al., "Protein engineering of antibody binding sites: recovery of specific activity in an anti-digoxin single-chain Fv analogue produced in *Escherichia coli*", Proc. Natl. Acad. Sci. USA, Aug. 1988, 85(16), 5879-5883.

(56) References Cited

OTHER PUBLICATIONS

Jackman, A.L., et al., "Cellular pharmacology and in vivo activity of a new anticancer agent, ZD9331: a water-soluble, nonpolygluamatable, quinazoline-based inhibitor of thymidylate synthase", Clin. Cancer Res., Jun. 1997, 3(6), 911-921.

Jackman, A.L., et al., "ICI D1694, a quinazoline antifolate thymidylate synthase inhibitor that is a potent inhibitor of L1210 tumor cell growth in vitro and in vivo: a new agent for clinical study", Cancer Res., Oct. 15, 1991, 51(20), 5579-5586.

Johnston, S. R., "Ovarian cancer: review of the National Institute for Clinical Excellence (NICE) guidance recommendations", Cancer Invest., Dec. 2004, 22(5), 730-742.

Jones, P.T., et al., "Replacing the complementarity-determining regions in a human antibody with those from a mouse", Nature, May 29-Jun. 4, 1986, 321(6069), 522-525.

Kalli et al., "Folate receptor alpha as a tumor target in epithelial ovarian cancer", Gynecol Oneal., 2008, 108(3), 619-626.

Kanner et al., "Farletuzumab, a Humanized Monoclonal Antibody Against Folate Receptor a, in Epithelial Ovarian Cancer: a Phase I Study", Clinical Cancer Research, Nov. 1, 2010, 16(21), 5288-5295.

Kaufman, et al. (Eds.), Handbook of Molecular and Cellular Methods in Biology and Medicine, CRC Press, Boca Raton, 1995.

Keepers, Y.P., et al., "Comparison of the sulforhodamine B protein and tetrazolium (MTT) assays for in vitro chemosensitivity testing", Eur. J. of Cancer, 1991, 27(7), 897-900.

Keleman, "The role of folate receptor alpha in cancer development, progression and treatment: cause, consequence or innocent bystander", Int J Cancer, Jul. 15, 2006, 119(2), 243-250.

Khazaeli, M.B., et al., "Human immune response to monoclonal antibodies", J Immunother Emphasis Tumor Immunol., Jan. 1994, 15(1), 42-52.

Kikuchi, Y. et al., "Apoptosis inducing bivalent single-chain antibody fragments against CD47 showed antitumor potency for multiple myeloma", Leuk. Res., Apr. 2005, Epub: Dec. 18, 2004, 29(4), 445-450.

Kohler, G., et al., "Continuous cultures of fused cells secreting antibody of predefined specificity", Nature, Aug. 7, 1975, 256(5517), 495-497.

Kontermann, et al. (Eds.), Antibody Engineering (Springer Lab Manual), Springer-Verlag, 2001.

Kozbor, D., et al., "The production of monoclonal antibodies from human lymphocytes", Immunol. Today, 1983, 4(3), 72-79.

Kreitman, R. J., et al., "Immunotoxins for targeted cancer therapy", Adv. Drug Del. Rev., Apr. 6, 1998, 31(1-2), 53-88.

Kusano, A. et al., "Immunocytochemical study on internalization of anti-carbohydrate monoclonal antibodies", Anticancer Res., Nov.-Dec. 1993, 13(6A), 2207-2212.

Kyriakos, R.J., et al., "The fate of antibodies bound to the surface of tumor cells in vitro", Cancer Res., Feb. 15, 1992, 52(4), 835-842.

Lacey, S. W. et al., "Complementary DNA for the Folate Binding Protein Correctly Predicts Anchoring to the Membrane by Glycosyi-Phosphatidylinositol", J. Clin. Invest, Aug. 1989, 84(2), 715-720.

Leamon et al., "Delivery of macromolecules into living cells: a method that exploits folate receptor endocytosis", Proc Natl Acad Sci US A, 1991, 88, 5572-5576.

Lear et al. "Improved tumor imaging with radiolabeled monoclonal antibodies by plasma clearance of unbound antibody with anti-antibody column", Radiology, 1991, 179(2), 509-512.

Li, Q., et al., "Cytotoxic activity of the recombinant anti-mesothelin immunotoxin, SS1 (dsFv) PE38, towards tumor cell lines established from ascites of patients with peritoneal mesotheliomas", Anticancer Res., May-Jun. 2004, 24(3A), 1327-1335.

Little, M., et al., "Of mice and men: hybridoma and recombinant antibodies", Immunol. Today, Aug. 2000, 21(8), 364-370.

Maddage et al., "Farletuzumab (mAb003), a neutralizing monoclonal antibody to folate receptor alpha, enhances paclitaxel efficacy in an ovarian cancer model" [abstract]. In: Proceedings of the 103rd Annual Meeting of the American Association for Cancer Research; Mar. 31-Apr. 4, 2012; Chicago, Illinois. Philadelphia (PA): AACR; 2012. Abstract nr 4411.

Markman M. et al., "Phase II trial of weekly paclitaxel (80 mg/m2) in platinum and paclitaxel-resistant ovarian and primary peritoneal cancers: a Gynecologic Oncology Group study", Gynecologic Oncology, Jun. 2006, 101(3), 436-440.

Marks, J. D. et al., "By-passing immunization. Human antibodies from V-gene libraries displayed on phage", J. Mol. Bioi., Dec. 5, 1991, 222(3), 581-597.

Maziarz, K. M. et al., "Complete Mapping of Divergent Amino Acids Responsible for Differential Ligand Binding of Folate Receptors a and 13", J. Bioi. Chem., Apr. 16, 1999, 274(16), 11066-11091.

McCall, A.M., et al., "Increasing the affinity for tumor antigen enhances bispecific antibody cytotoxicity", J. of Immunol., May 15, 2001, 166(10), 6112-6117.

McPherson, (Ed.), Directed Mutagenesis: A Practical Approach, IRL Press, Oxford, 1991.

Miotti et al., "Interaction of folate receptor with signaling molecules lyn and Ga13 in detergent-resistant complexes from the ovary carcinoma cell lines", J Cell Sci, 2000, 113, 349-357.

Miotti, S., et al., "Characterization of human ovarian carcinoma-associated antigens defined by novel monoclonal antibodies with tumor-restricted specificity", Int. J. Cancer, Mar. 15, 1987, 39(3), 297-303.

Molthoff, C.F. et al., "Experimental and Clinical Analysis of the Characteristics of a Chimeric Monoclonal Antibody, MOv18, Reactive with an Ovarian Cancer-Associated Antigen", J Nucl Med., Nov. 1992, 33(11), 2000-2005.

Morphotek, "Morphotek Announces Top-Line Results of a Phase III Study of Farletuzumab in Patients With Relapsed Platinum-Sensitive Epithelial Ovarian Cancer", Exton, PA, Jan. 10, 2013, Press Release, p. 2, http://www.morphotek.com/news-events/News-Archive/2013-News/Morphotek-Announces-Top-Line-Results-of-A-Phase-II.aspx.

Morrison, S. L., et al., "Chimeric human antibody molecules: mouse antigen-binding domains with human constant region domains", Proc. Natl. Acad. Sci. USA, Nov. 1984, 81(21), 6851-6855.

Nelson et al., "51Cr Release Assay of Antibody-Dependent Cell-Mediated Cytotoxicity (ADCC)", Current Protocols in Immunol., May 2001, Chapter 7, Unit 7.27-7.27.8, 8 pages.

Nicolaides, N.C., et al., "Analysis of the 5' region of PMS2 reveals heterogeneous transcripts and a novel overlapping gene", Genomics, Sep. 20, 1995, 29(2), 329-334.

Niwa, R. et al., "Defucosylated chimeric anti-CC chemokine receptor 4 IgG1 with enhanced antibody-dependent cellular cytotoxicity shows potent therapeutic activity to T-cellleukemia and lymphoma", Cancer Res., Mar. 15, 2004, 64(6), 2127-2133.

Ordonez, N.G., "Application of mesothelin immunostaining in tumor diagnosis", Am. J. Surg. Pathol., Nov. 2003, 27(11), 1418-1428.

Orlandi, R., et al., "Cloning immunoglobulin variable domains for expression by the polymerase chain reaction", Proc. Natl. Acad. Sci. USA, May 1989, 86(10), 3833-3837.

Ottone, F., et al. "Relationship between folate-binding protein expression and cisplatin sensitivity in ovarian carcinoma cell lines", British Journal of Cancer, (1997) 76(1): 77-82.

Parsons, R., et al., "Mismatch repair deficiency in phenotypically normal human cells", Science, May 5, 1995, 268(5211), 738-740.

Paul, M.-A., et al., "Selection of tumor-specific internalizing human antibodies from phage libraries", J. of Molecular Bioi., Sep. 1, 2000, 301(5), 1149-1161.

Peoples, G.E., et al., "Vaccine implications of folate binding protein, a novel cytotoxic T lymphocyte-recognized antigen system in epithelial cancers", Clinical Cancer Res., Dec. 1999, 5(12), 4214-4223.

Persson, M.A. A., et al., "Generation of diverse high-affinity human monoclonal antibodies by repertoire cloning", Proc. Nat. Acad. Sci. USA, Mar. 15, 1991, 88(6), 2432-2436.

Peters, G.J., et al., "Transformation of mouse fibroblasts with the oncogenes H-ras OR trk is associated with pronounced changes in drug sensitivity and metabolism", Int. J. of Cancer, May 28, 1993, 54(3), 450-455.

Powers, "Interaction among folate, riboflavin, genotype, and cancer, with reference to colorectal and cervical cancer" Dec. 2005, 135(12Suppl): 2960S-2966S.

(56) References Cited

OTHER PUBLICATIONS

Queen, C., et al., "A humanized antibody that binds to the interleukin 2 receptor", Proc. Nat. Acad. Sci. USA, Dec. 1989, 86(24), 10029-10033.
Rafi, I., et al., "Preclinical and phase I clinical studies with the nonclassical antifolate thymidylate synthase inhibitor nolatrexed dihydrochloride given by prolonged administration in patients with solid tumors", J. of Clin. Oneal., Mar. 1998, 16(3), 1131-1141.
Reichmann, L., et al., "Reshaping human antibodies for therapy", Nature, 1988, 332, 323-327.
Rettig, W.J., et al., "Cell-surface glycoproteins of human sarcomas: differential expression in normal and malignant tissues and cultured cells", Proc. Natl. Acad. Sci. USA, May 1988, 85(9), 3110-3114.
Rhee, M.S. et al., "Biochemical studies on PT523, a potent nonpolyglutamatable antifolate, in cultured cells", Mol. Pharmacal., Apr. 1994, 45(4), 783-791.
Ripani, E. et al., "Human Trop-2 is a tumor-associated calcium signal transducer", Int. J. Cancer, May 29, 1998, 76(5), 671-676, (Abstract).
Rosowsky, A., "PT523 and other aminopterin analogs with a hemiphthaloyi-L-ornithine side chain: exceptionally tight-binding inhibitors of dihydrofolate reductase which are transported by the reduced folate carrier but cannot form polyglutamates", Curr. Med. Chem., Apr. 1999, 6(4), 329-352.
Ross, J.F., et al., "Differential regulation of folate receptor isoforms in normal and malignant tissues in vivo and in established cell lines", Cancer, May 1, 1994, 73(9), 2432-2443.
Ross, J.S. et al., "Antibody-based therapeutics in oncology", Exp. Rev. Anticancer Ther., Feb. 2003, 3(1), 107-121.
Rudikoff et al, "Single amino acid substitution altering antigen-binding specificity", PNAS, USA, Mar. 1982, 79(6), 1979-1983.
Rudnick and Adams, "Affinity and Avidity in Antibody-Based Tumor Targeting", Cancer Biother Radiopharm, 24(2), Apr. 2009, 155-162.
Sadasivan, E., et al., "Purification, properties, and immunological characterization of folate-binding proteins from human leukemia cells", Biochim. et Biophys. Acta, Jul. 16, 1987, 925(1), 36-47.
Sambrook, et al., Molecular Cloning: A Laboratory Manual, 2na Ed., Cold Spring Harbor Laboratory Press, Plainview, New York, 1989.
Scholl et al., "Folic Acid: Influence on the Outcome of Pregnancy", Am. J. Clin. Nutr., May 2000, 71(5 Supplement), 1295S-1303S.
Scholler, N., et al., "Soluble member(s) of the mesothelin/megakaryocyte potentiating factor family are detectable in sera from patients with ovarian carcinoma", Proc. Natl. Acad. Sci. USA, Sep. 28, 1999, 96(20), 11531-11536.
Scott, A. M. et al., "Immunological effects of chimeric anti-GD3 monoclonal antibody KM871 in patients with metastatic melanoma", Cancer Immun., Feb. 22, 2005, 5(3), 1-12.
Shen, F. et al., "Expression levels of functional folate receptors alpha and Beta are related to the number of N-glycosylated sites", Biochem J. Nov. 1, 1997, 327(Pt. 3), 759-764.
Shewach, D. S. et al., "Radiosensitization of human tumor cells by gemcitabine in vitro", Semin. Oneal., Aug. 1995, 22(2 Suppl11), 68-71.
Shields, R.L., et al., "Anti-IgE monoclonal antibodies that inhibit allergen-specific histamine release", Int. Arch. Allergy Immunol., May-Jun. 1995, 107(1-3), 412-413.
Shields, R.L., et al., "High resolution mapping of the binding site on human IgG1 for FcgammaRI, FcgammaRII, FcgammaRIII, and FeRn and design of IgG1 variants with improved binding to the FcgammaR", J. of Biological Chem., Mar. 2, 200, Epub: Nov. 28, 2000, 276(9), 6591-6604.
Shih, C., et al., "LY231514, a pyrrolo[2,3-d]pyrimidine-based antifolate that inhibits multiple folate-requiring enzymes", Cancer Res., Mar. 15, 1997, 57(6), 1116-1123.
Shinkawa, T., et al., "The absence of fucose but not the presence of galactose or bisecting N-acetylglucosamine of human IgG1 complex-type oligosaccharides shows the critical role of enhancing antibody-dependent cellular cytotoxicity", J. Biological Chem., Jan. 31, 2003, Epub: Nov. 8, 2002, 278(5), 3466-3473.
Skerra, A., et al., "Assembly of a functional immunoglobulin Fv fragment in *Escherichia coli*", Science, May 20, 1988, 240(4855), 1038-1041.
Smith-Jones et al., "Preclinical radioimmunotargeting of folate receptor alpha using the monoclonal antibody conjugate DOTA-MORAb-003", Nucl Med Bioi, Apr. 2008, 35(3), 343-351.
Spannuth et al., "Farletuzumba in Epithelial Ovarian Carcinoma", Expert Opinion on Biological Therapy, Mar. 2010, 10(3), 431-437.
Spannuth WA et al., "Therapeutic Eficacy of Folate Receptor a blockade with MORAb-0003 in Ovarian Cancer", Gynecologic Oncology, 2008, Abstracts, 108(3S), S135.
Strome et al., "A Mechanistic Perspective of Monoclonal Antibodies in Cancer Therapy Beyond Target-Related Effects", Oncologist, Sep. 2007, 12(9), 1084-1095.
Sudimack, J., et al., "Targeted drug delivery via the folate receptor", Adv. Drug Deliv. Rev., Mar. 30, 2000, 41(2), 147-162.
Talmadge et al., 'Murine models to evaluate novel and conventional therapeutic strategies for cancer', The American Journal of Pathology, Mar. 2007, 170(3), 793-804.
Taylor, E.C., et al., "A dideazatetrahydrofolate analogue lacking a chiral center at C-6, N-[4[2-(2-amino-3,4-dihydro-4-ox-7H-pyrrolo[2,3-d]pyrimidin-5-yl)ethyl]benzoyi]-glutamic Acid, is an inhibitor of thymidylate synthase", J. Med. Chem., Nov. 13, 1992, 35(23), 4450-4454.
Tempest, P.R., et al., "Reshaping a human monoclonal antibody to inhibit human respiratory syncytial virus infection in vivo", Biotechnology, Mar. 1991, 9(3), 266-271.
Thurber et al., "Antibody tumor penetration: transport opposed by systemic and antigen-mediated clearance", Adv Drug Deliv Revs, 60(12), Sep. 2008, 1421-1434.
Tibben et al., 'Pharmacokinetics, biodistribution and biological effects of intravenously administered bispecific monoclonal antibody OC/TR F(ab')2 in ovarian carcinoma patients', Int. J. Cancer, May 16, 1996, 66(4):477-486, Abstract Only.
Toffoli et al, "Resistance to Methotrexate in SKOV-3 Cell Lines After Chronic Exposure to Carbamazepine is Associated with a Decreased Expression of Folate Receptor", Int J Cancer, 85(5), Mar. 1, 2000, 683-690.
Toffoli et al., "Overexpression of folate binding protein in ovarian cancers", Int J Cancer, 1997, 74(2), 193-198.
Tomassetti, A., et al., "Isolation and biochemical characterization of the soluble and membrane forms of folate binding protein expressed in the ovarian carcinoma cell line IGOV1", FEBS Letts., Feb. 8, 1993, 317(1-2), 143-146.
Van Zanten Przbysz, 1., et al., "cellular and humoral responses after multiple injections of unconjugated chimeric monoclonal antibody MOv18 in ovarian cancer patients: a pilot study", J. Cancer Res. Clin. Oneal., Sep. 2002, Epub: Aug. 23, 2002, 128(9), 484-492.
VanZanten-Przybysz, I., et al., "Influence of the route of administration on targeting of ovarian cancer with the chimeric monoclonal antibody MOV18: I.V. vs. I.P.", Int. J. of Cancer, Apr. 1, 2001, 92(1), 106-114.
Veggian, R., et al., "Immunohistochemical reactivity of a monoclonal antibody prepared against human ovarian carcinoma on normal and pathological female genital tissues", Tumori, Oct. 31, 1989, 75(5), 510-513.
Velders, M.P., et al., "The impact of antigen density and antibody affinity on antibody-dependent cellular cytotoxicity: relevance for immunotherapy of carcinomas", B. J. Cancer, Aug. 1998, 78(4), 478-483.
Verhoeyen, M., et al., "Reshaping human antibodies: grafting an antilysozyme activity", Science, Mar. 25, 1988, 239(4847), 1534-1536.
Voskoglou-nomikos et al., 'Clinical predictive value of the in vitro cell line, human xenograft, and mouse allograft preclinical cancer models', Clinical Cancer Research, Sep. 15, 2003, 9(11), 4227-4239.
Wallace, "Second Conference on Industrial Immunology", "Humanized Antibodies Specific for Human Cancers", IchemeIndustrialImmunology, a two-day symposium organized by the

(56) References Cited

OTHER PUBLICATIONS

Instituition of Chemical Engineers on behalf of the British Coordinating Committee for Biotechnology, and held in Brighton, UK, Jul. 4-5, 1994, 6 pages.

Ward, E.S., et al., "Binding activities of a repertoire of single immunoglobulin variable domains secreted from *Escherichia coli*", Nature, Oct. 12, 1989, 341(2642), 544-546.

Webber, S., et al., "AG337, a novel lipophilic thymidylate synthase inhibitor: in vitro and in vivo preclinical studies", Cancer Chemother. Pharmacal., 1996, 37(6), 509-517.

Weitman, S.D., et al., "Distribution of the folate receptor GP38 in normal and malignant cell lines and tissues", Cancer Res., Jun. 15, 1992, 52(12), 3396-3401.

Wolff, E.A., et al., "Monoclonal antibody homodimers: enhanced antitumor activity in nude mice", Cancer Res., Jun. 1, 1993, 53(11), 2560-2565.

Yamaguchi, N., et al., "A novel cytokine exhibiting megakaryocyte potentiating activity from a human pancreatic tumor cell line HPC-Y5", J. Biol. Chem., Jan. 14, 1994, 269(2), 805-808.

Yang, X.-D., et al., "Eradication of established tumors by a fully human monoclonal antibody to the epidermal growth factor receptor without concomitant chemotherapy", Cancer Research, Mar. 15, 1999, 59(6), 1236-1243.

Zafiropoulos, A., et al., "Induction of antigen-specific isotype switching by in vitro immunization of human naïve B lymphocytes", J. of Immunological Methods, Jan. 15, 1997, 200(1-2), 181-190.

Zhang et al, "ErbB Receptors: From Oncogenes to Targeted Cancer Therapies" The Journal of Clinical Investigation, Aug. 2007, 117(8), 2051-2058.

Zola, Monoclonal Antibodies: Preparation and Use of Monoclonal Antibodies and Engineered Antibody Derivatives (Basics: From Background to Bench), Springer-Verlag Ltd., New York, 2000.

Canadian Patent Application No. 2,556,027: Office Action dated Jan. 21, 2014, 4 pages.

Gould et al.; "Comparison of IgE and IgG antibody-dependent cytotoxicity in vitro and in a SCID mouse xenograft model of ovarian carcinoma"; Eur. J. Immunol.; 1999; 29; p. 3527-3537.

Andersson et al.; "The Curative and Palliative Potential of the Monoclonal Antibody MOv18 Labelled with At in Nude Mice with Intraperitoneally growing Ovarian Cancer Xenografts"; Acta Oncologica; vol. 39 No. 6; 2000; p. 741-745.

Almagro and Fransson, "Humanization of Antibodies", Frontiers in Bioscience, Jan. 1, 2008, 13, 1619-1633.

De Genst et al, "Antibody Repertoire Development in Camelids", Development & Comparative Immunology, Feb. 2006, 30(1-2), 187-198.

Canevari et al., "Ovarian Carcinoma Therapy with Monoclonal Antibodies", Hybridoma, 1993, 12(5), 501-507.

Lin et al., "The antitumor activity of the human FOLR1-specific monoclonal antibody, farletuzumab, in an ovarian cancer mouse model is mediated by antibody-dependent cellular cytotoxicity", Cancer Biology & Therapy, Nov. 2013, 14:11, 1032-1038.

White et al., "Efficacy and safety of farletuzumab, a humanized monoclonal antibody to folate receptor alpha, in platinum-sensitive relapsed ovarian cancer subjects: Final data from a multicenter phase II study", J. Clin. Oncol., 2010, 28(15S), Abstract 5001.

* cited by examiner

Fig. 5A

Amino acid alignment
```
LK26-LC-FL:1  MGWSCIILFLVATATGVHSDIQLTQSPSSLSASVGDRVTITCSVSSSISSNNLHWYQQKP 60
              MGWSCIILFLVATATGVHSDIQLTQSPSSLSASVGDRVTITCSVSSSISSNNLHWYQQKP
LK26-LC-sv:1  MGWSCIILFLVATATGVHSDIQLTQSPSSLSASVGDRVTITCSVSSSISSNNLHWYQQKP 60
```

Fig. 5B

CLUSTAL W (1.82) multiple sequence alignment

```
LK26-LC-full-length      ATGGGATGGAGCTGTATCATCCTCTTCTTGGTAGCAACAGCTACAGGTGT 50
LK26-LC-splice-variant   ATGGGATGGAGCTGTATCATCCTCTTCTTGGTAGCAACAGCTACAGGTGT 50
                         **************************************************

LK26-LC-full-length      CCACTCCGACATCCAGCTGACCCAGAGCCCAAGCAGCCTGAGCGCCAGCG 100
LK26-LC-splice-variant   CCACTCCGACATCCAGCTGACCCAGAGCCCAAGCAGCCTGAGCGCCAGCG 100
                         **************************************************

LK26-LC-full-length      TGGGTGACAGAGTGACCATCACCTGTAGTGTCAGCTCAAGTATAAGTTCC 150
LK26-LC-splice-variant   TGGGTGACAGAGTGACCATCACCTGTAGTGTCAGCTCAAGTATAAGTTCC 150
                         **************************************************

LK26-LC-full-length      AACAACTTGCACTGGTACCAGCAGAAGCCAGGTAAGGCTCCAAAGCCATG 200
LK26-LC-splice-variant   AACAACTTGCACTGGTACCAGCAGAAGCCCG------------------ 181
                         *****************************

LK26-LC-full-length      GATCTACGGCACATCCAACCTGGCTTCTGGTGTGCCAAGCAGATTCAGCG 250
LK26-LC-splice-variant   --------------------------------------------------

LK26-LC-full-length      GTAGCGGTAGCGGTACCGACTACACCTTCACCATCAGCAGCCTCCAGCCA 300
LK26-LC-splice-variant   ----------------------------------------CAGCCTCCAGCCA 194
                                                                 *************

LK26-LC-full-length      GAGGACATCGCCACCTACTACTGCCAACAGTGGAGTAGTTACCCGTACAT 350
LK26-LC-splice-variant   GAGGACATCGCCACCTACTACTGCCAACAGTGGAGTAGTTACCCGTACAT 244
                         **************************************************

LK26-LC-full-length      GTACACGTTCGGCCAAGGGACCAAGGTGGAAATCAAACGAACTGTGGCTG 400
LK26-LC-splice-variant   GTACACGTTCGGCCAAGGGACCAAGGTGGAAATCAAACGAACTGTGGCTG 294
                         **************************************************

LK26-LC-full-length      CACCATCTGTCTTCATCTTCCCGCCATCTGATGAGCAGTTGAAATCTGGA 450
LK26-LC-splice-variant   CACCATCTGTCTTCATCTTCCCGCCATCTGATGAGCAGTTGAAATCTGGA 344
                         **************************************************

LK26-LC-full-length      ACTGCCTCTGTTGTGTGCCTGCTGAATAACTTCTATCCCAGAGAGGCCAA 500
LK26-LC-splice-variant   ACTGCCTCTGTTGTGTGCCTGCTGAATAACTTCTATCCCAGAGAGGCCAA 394
                         **************************************************

LK26-LC-full-length      AGTACAGTGGAAGGTGGATAACGCCCTCCAATCGGGTAACTCCCAGGAGA 550
LK26-LC-splice-variant   AGTACAGTGGAAGGTGGATAACGCCCTCCAATCGGGTAACTCCCAGGAGA 444
                         **************************************************

LK26-LC-full-length      GTGTCACAGAGCAGGACAGCAAGGACAGCACCTACAGCCTCAGCAGCACC 600
LK26-LC-splice-variant   GTGTCACAGAGCAGGACAGCAAGGACAGCACCTACAGCCTCAGCAGCACC 494
                         **************************************************

LK26-LC-full-length      CTGACGCTGAGCAAAGCAGACTACGAGAAACACAAAGTCTACGCCTGCGA 650
LK26-LC-splice-variant   CTGACGCTGAGCAAAGCAGACTACGAGAAACACAAAGTCTACGCCTGCGA 544
                         **************************************************

LK26-LC-full-length      AGTCACCCATCAGGGCCTGAGCTCGCCCGTCACAAAGAGCTTCAACAGGG 700
LK26-LC-splice-variant   AGTCACCCATCAGGGCCTGAGCTCGCCCGTCACAAAGAGCTTCAACAGGG 594
                         **************************************************

LK26-LC-full-length      GAGAGTGTTAA 711
LK26-LC-splice-variant   GAGAGTGTTAA 605
                         ***********
```

MONOCLONAL ANTIBODIES THAT SPECIFICALLY BLOCK BIOLOGICAL ACTIVITY OF A TUMOR ANTIGEN

CROSS-REFERENCE TO RELATED APPLICATION

This application is a continuation of U.S. application Ser. No. 12/500,144, filed Jul. 9, 2009, which is a continuation of U.S. application Ser. No. 11/056,776, filed Feb. 11, 2005, which claims benefit of U.S. Appl. No. 60/544,364, filed Feb. 12, 2004. The content of each of these applications is incorporated herein by reference in its entirety.

FIELD OF THE INVENTION

This invention relates to purified novel monoclonal antibodies that specifically bind to the alpha-folate receptor ("FR-α") and compositions thereof. In some embodiments, the antibodies of the invention block the biological activity of FR-α. The antibodies and compositions of the invention are useful in the treatment of certain cancers, particularly cancers that have increased cell surface expression of the alpha-folate receptor, such as ovarian, breast, renal, colorectal, lung, endometrial, or brain cancer. The invention also relates to hybridoma cells expressing the monoclonal antibodies, antibody derivatives, such as chimeric and humanized monoclonal antibodies, antibody fragments, mammalian cells expressing the monoclonal antibodies, derivatives and fragments, compositions of purified antibodies of the invention, and methods of detecting and treating cancer using the antibodies, derivatives, fragments, and compositions of the invention.

BACKGROUND OF THE INVENTION

There are three major isoforms of the human membrane folate binding protein, α, β, and γ. The α and β isoforms have about 70% amino acid sequence homology, and differ dramatically in their stereospecificity for some folates. Both isoforms are expressed in fetal and adult tissue, although normal tissue generally expresses low to moderate amounts of FR-β. FR-α, however, is expressed in normal epithelial cells, and is frequently strikingly elevated in a variety of carcinomas (Ross et al. (1994) *Cancer* 73(9):2432-2443; Rettig et al. (1988) *Proc. Natl. Acad. Sci. USA* 85:3110-3114; Campbell et al. (1991) *Cancer Res.* 51:5329-5338; Coney et al. (1991) *Cancer Res.* 51:6125-6132; Weitman et al. (1992) *Cancer Res.* 52:3396-3401; Garin-Chesa et al. (1993) *Am. J. Pathol.* 142:557-567; Holm et al. (1994) *APMIS* 102:413-419; Franklin et al. (1994) *Int. J. Cancer* 8 (Suppl.):89-95; Miotti et al. (1987) *Int. J. Cancer* 39:297-303; and Vegglan et al. (1989) *Tumori* 75:510-513). FR-α is overexpressed in greater than 90% of ovarian carcinomas (Sudimack and Lee (2000) *Adv. Drug Deliv. Rev.* 41(2):147-62). FR-α generally attaches to the cell surface membrane via a GPI anchor. GPI anchors contain oligosaccharides and inositol phospholipids.

In 1987, Miotti et al. described three new monoclonal antibodies that recognized antigens on human ovarian carcinoma cells (Miotti et al. (1987) *Int. J. Cancer* 39(3):297-303). One of these was designated MOv18, which recognizes a 38 kDa protein on the surface of choriocarcinoma cells. MOv18 is a murine, IgG1, kappa antibody and mediates specific cell lysis of the ovarian carcinoma cell line, IGROV1. Alberti et al. ((1990) *Biochem. Biophys. Res. Commun.* 171(3):1051-1055) showed that the antigen recognized by MOv18 was a GPI-linked protein. This was subsequently identified as the human folate binding protein (Coney et al. (1991) *Cancer Res.* 51(22):6125-6132). Tomassetti et al. showed that MOv18 recognizes a soluble form and a GPI-anchored form of the folate binding protein in IGROV1 cells (Tomassetti et al. (1993) *FEBS Lett.* 317(1-2):143-146). Subsequent work combined the variable regions of the mouse MOv18 with human IgG1 (kappa) constant region to create a chimerized MOv18 antibody. The chimerized antibody mediated higher and more specific lysis of IGROV 1 cells at 10-100-fold lower antibody concentrations (Coney et al. (1994) *Cancer Res.* 54(9):2448-2455). The 38 kDa antigen appears to be the monomeric form of FR-α.

U.S. Pat. No. 5,952,484 describes a humanized antibody that binds to a 38 kDa protein (FR-α). The antibody was named LK26. The original mouse monoclonal antibody was described by Rettig in European Patent Application No. 86104170.5 (published as EP0197435 and issued in the U.S. as U.S. Pat. No. 4,851,332).

Ovarian cancer is a major cause of death due to gynecological malignancy. Although chemotherapy is the recommended treatment and has enjoyed some success, the 5-year survival rate is still less than 40%.

A difficult problem in antibody therapy in cancer is that often the target of the antibody is expressed by normal tissues as well as cancerous tissues. Thus, the antibodies that are used to kill cancer cells also have a deleterious effect on normal cells. Finding unique targets or targets that are preferentially expressed in cancer tissues has proven difficult in many cancers. Identification of preferentially expressed targets and the ability to block the biological activity of such targets may be an effective treatment for cancer. As such, more effective antibody therapies for ovarian and other FR-α-bearing cancers that avoids or minimizes reactivity with normal tissues are needed.

SUMMARY OF THE INVENTION

In some embodiments, the invention provides antibodies that specifically bind to FR-α. The antibodies of the invention preferably block a biological activity of FR-α. In some embodiments, the invention provides antibody-producing cells and compositions of antibodies that specifically bind to FR-α wherein the cells and compositions are substantially free of FR-α binding competitors. In some embodiments, antibody-producing cells that produce antibodies comprising substantially only antibody of the invention are provided. In preferred embodiments, the antibodies of the invention bind FR-α with a binding affinity of at least about $1\times10^{-7}$ M, at least about $1\times10^{-8}$ M, at least about $1\times10^{-9}$ M, and most preferably at least about $1\times10^{-10}$ M.

It has been discovered that tumors that overexpress FR-α tend to favor the formation of multimeric forms of FR-α, for example tetramers. Without wishing to be bound by any particular theory, it is believed that the formation of the multimeric form of FR-α is driven by a mass effect due to the accumulation of larger amounts of FR-α on the surface of tumor cells. Previously, other researchers only found higher molecular weight species of FR-α in gel filtration assays which represented FR-α inserted into Triton X-100 micelles via their hydrophobic tails (Holm et al. (1997) *Biosci. Reports* 17(4):415-427). In some embodiments, the invention provides antibodies that specifically bind to the multimeric form of FR-α and not the monomeric form.

In some embodiments, the antibodies of the invention (a) bind to an epitope of FR-α other than the epitope bound by antibody LK26; (b) bind FR-α with greater affinity than antibody LK26; (c) out-compete antibody LK26 for binding to the multimeric form of FR-α and thereby block the biological activity of FR-α; and/or (d) are purified relative to LK26.

In some embodiments, the antibodies of the invention recognize a disulfide-dependent epitope.

Some embodiments of the invention relate to antibodies comprising a heavy chain comprising an amino acid sequence of SEQ ID NO:5. In some embodiments, the heavy chain comprises an amino acid sequence of SEQ ID NO:6.

In some embodiments, the antibodies of the invention comprise a light chain comprising the amino acid sequence of SEQ ID NO:2. In some embodiments of the invention, the antibodies comprise a light chain comprising the amino acid sequence of SEQ ID NO:3.

The invention further provides antibodies comprising a heavy chain comprising an amino acid of SEQ ID NO:5 or SEQ ID NO:6 and a light chain comprising an amino acid sequence of SEQ ID NO:2 or SEQ ID NO:3. The antibodies of the invention preferably comprise a heavy chain comprising an amino acid sequence of SEQ ID NO:5 and a light chain comprising an amino acid sequence of SEQ ID NO:2 and more preferably comprise a heavy chain comprising an amino acid sequence of SEQ ID NO:6 and a light chain comprising an amino acid sequence of SEQ ID NO:3. In some embodiments of the invention, the heavy chain of the antibody is encoded by a nucleic acid comprising the nucleotide sequence of SEQ ID NO:7. In some embodiments of the invention, the light chain of the antibody is encoded by a nucleic acid comprising the nucleotide sequence of SEQ ID NO:8.

The antibodies of the invention may be chimeric antibodies, including, but not limited to human-mouse chimeric antibodies. The antibodies of the invention may also be humanized antibodies. The invention also provides: cells, including hybridoma cells, that express the antibodies of the invention; polynucleotides that encode the antibodies of the invention; vectors comprising the polynucleotides that encode the antibodies of the invention; and expression cells comprising the vectors of the invention.

The invention also provides methods of producing an antibody that specifically binds to FR-α. In some embodiments, the method comprises the step of culturing the antibody-producing cells of the invention. The cells of the invention may be insect cells or animal cells, preferably, mammalian cells.

The invention further provides methods of inhibiting the growth of dysplastic cells associated with increased expression of FR-α comprising administering to a patient with such dysplastic cells a composition comprising an antibody of the invention. The antibody preferably blocks a biological activity of FR-α. The methods may be used for various dysplastic conditions, such as, but not limited to ovarian, breast, renal, colorectal, lung, endometrial, or brain cancer. In preferred embodiments, the patients are human patients. In some embodiments, the antibodies are conjugated to cytotoxic agents such as, but not limited to radionuclides, toxins, and chemotherapeutic agents. In some embodiments, the antibodies are co-administered with an antifolate agent. The antifolate agent and antibody of the invention may be administered at the same time or simultaneously (that is, together), or in any order.

The invention also provides methods for decreasing the growth of cancer cells using monoclonal antibodies that specifically bind to FR-α, preferably mammalian FR-α. The methods of the invention may be used to modulate the growth of cancer cells and the progression of cancer in mammals, including humans. The cancer cells that may be inhibited include all cancer cells that have an increased expression of FR-α in relation to normal human tissues, such as but not limited to ovarian, breast, renal, colorectal, lung, endometrial, or brain cancer cells.

Also provided by the invention are compositions of antibodies of the invention. In preferred embodiments, the compositions are substantially pure. Substantially pure compositions of antibodies of the invention preferably comprise at least about 90%, more preferably at least about 95%, even more preferably at least about 99%, and most preferably about 100% by weight of antibodies of the invention.

BRIEF DESCRIPTION OF THE DRAWINGS

FIG. 5A illustrates a sequence alignment of light chain of an anti-FR-α antibody of the invention having an amino acid sequence of SEQ ID NO:3 and the light chain of an aberrant translation product having an amino acid sequence of SEQ ID NO: 24. FIG. 5B illustrates a sequence alignment of the nucleic acid sequence of a light chain of an anti-FR-α antibody of the invention having a sequence of SEQ ID NO:8 and a nucleic acid sequence encoding the aberrant translation product having a sequence of SEQ ID NO:25.

DETAILED DESCRIPTION OF ILLUSTRATIVE EMBODIMENTS

Figure 1:
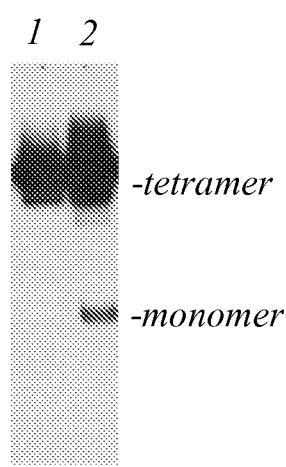
FIG. 1 shows a western blot of tumor cells showing the tetrameric and monomeric forms of FR-α.

The reference works, patents, patent applications, and scientific literature, including accession numbers to GenBank database sequences that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology known to those of skill in the art include Ausubel et al. CURRENT PROTOCOLS IN MOLECULAR BIOLOGY, John Wiley & Sons, New York (1998); Sambrook et al. MOLECULAR CLONING: A LABORATORY MANUAL, 2D ED., Cold Spring Harbor Laboratory Press, Plainview, N.Y. (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991).

As used herein, the term "epitope" refers to the portion of an antigen to which a monoclonal antibody specifically binds.

As used herein, the term "conformational epitope" refers to a discontinuous epitope formed by a spatial relationship between amino acids of an antigen other than an unbroken series of amino acids.

As used herein, the term "multimeric" refers to a grouping of two or more identical or nearly identical units. As used herein, the term "tetrameric" refers to a grouping of four, identical or nearly identical units.

As used herein, the term "monomeric" refers to a single unit of a mature protein that assembles in groups with other units.

As used herein, the term "inhibition of growth of dysplastic cells in vitro" means a decrease in the number of tumor cells, in culture, by at least about 5%, preferably about 10%, more preferably about 20%, more preferably about 30%, more preferably about 40%, more preferably about 50%, more preferably about 60%, more preferably about 70%, more preferably about 80%, more preferably about 90%, more preferably about 95%, more preferably about 99%, and most preferably 100%. In vitro inhibition of tumor cell growth may be measured by assays known in the art, such as the GEO cell soft agar assay.

As used herein, the term "inhibition of growth of dysplastic cells in vivo" means a decrease in the number of tumor cells, in an animal, by at least about 5%, preferably about 10%, more preferably about 20%, more preferably about 30%, more preferably about 40%, more preferably about 50%, more preferably about 60%, more preferably about 70%, more preferably about 80%, more preferably about 90%, more preferably about 95%, more preferably about 99%, and most preferably 100%. In vivo modulation of tumor cell growth may be measured by assays known in the art, for example but not limited to using the Response Evaluation Criteria in Solid Tumors (RECIST) parameters (available online through the National Cancer Institute Cancer Therapy Evaluation Program).

As used herein, "dysplastic cells" refer to cells that exhibit abnormal growth properties, such as but not limited to growth in soft agar, lack of contact inhibition, failure to undergo cell cycle arrest in the absence of serum, and formation of tumors when injected into immune-compromised mice. Dysplastic cells include, but are not limited to tumors, hyperplasia, and the like.

The term "preventing" refers to decreasing the probability that an organism contracts or develops an abnormal condition.

The term "treating" refers to having a therapeutic effect and at least partially alleviating or abrogating an abnormal condition in the organism. Treating includes inhibition of tumor growth, maintenance of inhibited tumor growth, and induction of remission.

The term "therapeutic effect" refers to the inhibition of an abnormal condition. A therapeutic effect relieves to some extent one or more of the symptoms of the abnormal condition. In reference to the treatment of abnormal conditions, a therapeutic effect can refer to one or more of the following: (a) an increase or decrease in the proliferation, growth, and/or differentiation of cells; (b) inhibition (i.e., slowing or stopping) of growth of tumor cells in vivo (c) promotion of cell death; (d) inhibition of degeneration; (e) relieving to some extent one or more of the symptoms associated with the abnormal condition; and (f) enhancing the function of a population of cells. The monoclonal antibodies and derivatives thereof described herein effectuate the therapeutic effect alone or in combination with conjugates or additional components of the compositions of the invention.

As used herein, the term "inhibits the progression of cancer" refers to an activity of a treatment that slows the modulation of neoplastic disease toward end-stage cancer in relation to the modulation toward end-stage disease of untreated cancer cells.

As used herein "blocks a biological activity of FR-α" refers to the ability of the antibodies (or fragments thereof) of the invention to prevent folate binding to FR-α, to prevent the uptake of folate by cells, or to inhibit signal transduction in the cell triggered by folate.

As used herein, the term "about" refers to an approximation of a stated value within an acceptable range. Preferably the range is +/−5% of the stated value.

As used herein, the term "neoplastic disease" refers to a condition marked by abnormal proliferation of cells of a tissue.

As used herein, the term "wild-type" refers to a native sequence, for example, a native nucleic acid sequence encoding or amino acid sequence of a heavy or light chain of the antibodies of the invention. Examples of wild-type sequences of the invention include the sequences of SEQ ID NOs:1-8.

As used herein, the term "FR-α binding competitors" refers to aberrant transcripts of the nucleic acids encoding antibodies of the invention and aberrant translation products of the antibodies of the invention that do not have the biological properties of the anti-FR-α antibodies of the invention (e.g., antigen binding affinity, ability to block a biological activity of FR-α). For example, an aberrant transcript may contain a deletion, a frameshift, a nonsense mutation, or a missense mutation. An example of an aberrant translation product is an alternative splice variant. An example of a FR-α binding competitor is an antibody comprising a light chain having an amino acid sequence of SEQ ID NO:24:

```
MGWSCIILFLVATATGVHSDIQLTQSPSSLSASVGDRVTIT

CSVSSSISSNNLHWYQQKPAASSQRTSPPTTANSGVVTRTC

TRSAKGPRWKSNELWLHHLSSSSRHLMSS.
```

The light chain of such an FR-α binding competitor may be encoded by a nucleic acid having a nucleic acid sequence of SEQ ID NO:25:

```
ATGGGATGGAGCTGTATCATCCTCTTCTTGGTAGCAACAGCTACA

GGTGTCCACTCCGACATCCAGCTGACCCAGAGCCCAAGCAGCCTG

AGCGCCAGCGTGGGTGACAGAGTGACCATCACCTGTAGTGTCAGC

TCAAGTATAAGTTCCAACAACTTGCACTGGTACCAGCAGAAGCCC

GCAGCCTCCAGCCAGAGGACATCGCCACCTACTACTGCCAACAGT

GGAGTAGTTACCCGTACATGTACACGTTCGGCCAAGGGACCAAGG

TGGAAATCAAACGAACTGTGGCTGCACCATCTGTCTTCATCTTCC

CGCCATCTGATGAGCAGTTGAAATCTGGAACTGCCTCTGTTGTGT

GCCTGCTGAATAACTTCTATCCCAGAGAGGCCAAAGTACAGTGGA

AGGTGGATAACGCCCTCCAATCGGGTAACTCCCAGGAGAGTGTCA

CAGAGCAGGACAGCAAGGACAGCACCTACAGCCTCAGCAGCACCC

TGACGCTGAGCAAAGCAGACTACGAGAAACACAAAGTCTACGCCT

GCGAAGTCACCCATCAGGGCCTGAGCTCGCCCGTCACAAAGAGCT

TCAACAGGGGAGAGTGTTAA.
```

As used herein, the term "purified" means a condition of being sufficiently separated from other proteins or nucleic acids with which it would naturally be associated, so as to exist in "substantially pure" form. "Purified" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations. A "purified" antibody preferably means an antibody substantially free of FR-α binding competitors. The term "substantially pure" means comprising at least about 50-60% by weight of a given material (e.g., nucleic acid, protein, etc.). More preferably, the preparation comprises at least about 75% by weight, and most preferably about 90-95% by weight of the given compound. Purity is measured by methods appropriate for the given material (e.g., chromatographic methods, agarose or polyacrylamide gel electrophoresis, HPLC analysis, and the like).

As used herein, the phrase "substantially free of FR-α binding competitors" refers to a condition of having less than about 50%, more preferably less than about 40%, more preferably less than about 30%, more preferably less than about 20%, more preferably less than about 10%, more preferably less than about 5%, more preferably less than about 1%, more preferably less than about 0.5%, and most preferably about 0% by weight of FR-α binding competitors.

Antibodies

The antibodies of the invention specifically bind folate receptor-alpha (FR-α). In some embodiments, the antibodies of the invention specifically bind a monomeric form of FR-α. In some embodiments, the antibodies of the invention specifically bind a multimeric form of FR-α (e.g., a tetrameric form) and not the monomeric form of FR-α. Preferred antibodies of the invention block a biological activity of FR-α. In preferred embodiments, the antibodies block a biological activity of FR-α on FR-α-bearing cells. Antibodies of the invention preferably induce antibody-dependent cellular cytotoxicity (ADCC) of FR-α-bearing cells. Examples of FR-α-bearing cells include but are not limited to ovarian, lung, breast, brain, renal, colorectal, and endometrial cancer cells.

Preferred antibodies, and antibodies suitable for use in the method of the invention, include, for example, fully human antibodies, human antibody homologs, humanized antibody homologs, chimeric antibody homologs, Fab, Fab', F(ab')$_2$ and F(v) antibody fragments, single chain antibodies, and monomers or dimers of antibody heavy or light chains or mixtures thereof. Antibodies of the invention are preferably monoclonal antibodies.

The antibodies of the invention may include intact immunoglobulins of any isotype including types IgA, IgG, IgE, IgD, IgM (as well as subtypes thereof). The antibodies preferably include intact IgG and more preferably IgG1. The light chains of the immunoglobulin may be kappa or lambda. The light chains are preferably kappa.

The antibodies of the invention include portions of intact antibodies that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like. Thus, antigen binding fragments, as well as full-length dimeric or trimeric polypeptides derived from the above-described antibodies are themselves useful.

A "chimeric antibody" is an antibody produced by recombinant DNA technology in which all or part of the hinge and constant regions of an immunoglobulin light chain, heavy chain, or both, have been substituted for the corresponding regions from another animal's immunoglobulin light chain or heavy chain. In this way, the antigen-binding portion of the parent monoclonal antibody is grafted onto the backbone of another species' antibody. One approach, described in EP 0239400 to Winter et al. describes the substitution of one species' complementarity determining regions (CDRs) for those of another species, such as substituting the CDRs from human heavy and light chain immunoglobulin variable region domains with CDRs from mouse variable region domains. These altered antibodies may subsequently be combined with human immunoglobulin constant regions to form antibodies that are human except for the substituted murine CDRs which are specific for the antigen. Methods for grafting CDR regions of antibodies may be found, for example in Riechmann et al. (1988) Nature 332:323-327 and Verhoeyen et al. (1988) Science 239:1534-1536.

The direct use of rodent monoclonal antibodies (MAbs) as human therapeutic agents led to human anti-rodent antibody ("HARA") (for example, human anti-mouse antibody ("HAMA")) responses which occurred in a significant number of patients treated with the rodent-derived antibody (Khazaeli, et al., (1994) Immunother. 15:42-52). Chimeric antibodies containing fewer murine amino acid sequences are believed to circumvent the problem of eliciting an immune response in humans.

Refinement of antibodies to avoid the problem of HARA responses led to the development of "humanized antibodies." Humanized antibodies are produced by recombinant DNA technology, in which at least one of the amino acids of a human immunoglobulin light or heavy chain that is not required for antigen binding has been substituted for the corresponding amino acid from a nonhuman mammalian immunoglobulin light or heavy chain. For example, if the immunoglobulin is a mouse monoclonal antibody, at least one amino acid that is not required for antigen binding is substituted using the amino acid that is present on a corresponding human antibody in that position. Without wishing to be bound by any particular theory of operation, it is believed that the "humanization" of the monoclonal antibody inhibits human immunological reactivity against the foreign immunoglobulin molecule.

As a non-limiting example, a method of performing complementarity determining region (CDR) grafting may be performed by sequencing the mouse heavy and light chains of the antibody of interest that binds to the target antigen (e.g., FR-α) and genetically engineering the CDR DNA sequences and imposing these amino acid sequences to corresponding human V regions by site directed mutagenesis. Human constant region gene segments of the desired isotype are added, and the "humanized" heavy and light chain genes are co-expressed in mammalian cells to produce soluble humanized antibody. A typical expression cell is a Chinese Hamster Ovary (CHO) cell. Suitable methods for creating the chimeric antibodies may be found, for example, in Jones et al. (1986) Nature 321:522-525; Riechmann (1988) Nature 332:323-327; Queen et al. (1989) Proc. Nat. Acad. Sci. USA 86:10029; and Orlandi et al. (1989) Proc. Natl. Acad. Sci. USA 86:3833.

Queen et al. (1989) Proc. Nat. Acad. Sci. USA 86:10029-10033 and WO 90/07861 describe the preparation of a humanized antibody. Human and mouse variable framework regions were chosen for optimal protein sequence homology. The tertiary structure of the murine variable region was computer-modeled and superimposed on the homologous human framework to show optimal interaction of amino acid residues with the mouse CDRs. This led to the development of antibodies with improved binding affinity for antigen (which is typically decreased upon making CDR-grafted chimeric antibodies). Alternative approaches to making humanized antibodies are known in the art and are described, for example, in Tempest (1991) *Biotechnology* 9:266-271.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) *Science* 242:423-442; Huston et al. (1988) *Proc. Natl. Acad. Sci. USA* 85:5879-5883; Ward et al. (1989) *Nature* 334: 54454; Skerra et al. (1988) *Science* 242:1038-1041.

The antibodies of the invention may be used alone or as immunoconjugates with a cytotoxic agent. In some embodiments, the agent is a chemotherapeutic agent. In some embodiments, the agent is a radioisotope, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the agent is a toxin or cytotoxic drug, including but not limited to ricin, modified *Pseudomonas* enterotoxin A, calicheamicin, adriamycin, 5-fluorouracil, and the like. Methods of conjugation of antibodies and antibody fragments to such agents are known in the literature.

The antibodies of the invention include derivatives that are modified, e.g., by the covalent attachment of any type of molecule to the antibody such that covalent attachment does not prevent the antibody from binding to its epitope. Examples of suitable derivatives include, but are not limited to fucosylated antibodies and fragments, glycosylated antibodies and fragments, acetylated antibodies and fragments, pegylated antibodies and fragments, phosphorylated antibodies and fragments, and amidated antibodies and fragments. The antibodies and derivatives thereof of the invention may themselves by derivatized by known protecting/blocking groups, proteolytic cleavage, linkage to a cellular ligand or other proteins, and the like. In some embodiments of the invention, at least one heavy chain of the antibody is fucosylated. In some embodiments, the fucosylation is N-linked. In some preferred embodiments, at least one heavy chain of the antibody comprises a fucosylated, N-linked oligosaccharide.

The antibodies of the invention include variants having single or multiple amino acid substitutions, deletions, additions, or replacements that retain the biological properties (e.g., block a biological activity of FR-α, binding affinity) of the antibodies of the invention. The skilled person can produce variants having single or multiple amino acid substitutions, deletions, additions or replacements. These variants may include, inter alia: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In another embodiment, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art. Antibodies of the invention also include antibody fragments. A "fragment" refers to polypeptide sequences which are preferably at least about 40, more preferably at least to about 50, more preferably at least about 60, more preferably at least about 70, more preferably at least about 80, more preferably at least about 90, and more preferably at least about 100 amino acids in length, and which retain some biological activity or immunological activity of the full-length sequence, for example, the ability to block a biological activity of FR-α and/or FR-α binding affinity.

The invention also encompasses fully human antibodies such as those derived from peripheral blood mononuclear cells of ovarian, breast, renal, colorectal, lung, endometrial, or brain cancer patients. Such cells may be fused with myeloma cells, for example, to form hybridoma cells producing fully human antibodies against FR-α.

In preferred embodiments of the invention, the antibody comprises a light chain comprising an amino acid sequence of SEQ ID NO:1:

```
DIQLTQSPSSLSASVGDRVTITCSVSSSISSNNLHWYQQKPGKAP
KPWIYGTSNLASGVPSRFSGSGSGTDYTFTISSLQPEDIATYYCQ
QWSSYPYMYTFGQGTKVEIK.
```

In some preferred embodiments, the antibody of the invention comprises a light chain comprising an amino acid sequence of SEQ ID NO:2:

```
DIQLTQSPSSLSASVGDRVTITCSVSSSISSNNLHWYQQKPGKAP
KPWIYGTSNLASGVPSRFSGSGSGTDYTFTISSLQPEDIATYYCQ
QWSSYPYMYTFGQGTKVEIKRTVAAPSVFIFPPSDEQLKSGTASV
VCLLNNFYPREAKVQWKVDNALQSGNSQESVTEQDSKDSTYSLSS
TLTLSKADYEKHKVYACEVTHQGLSSPVTKSFNRGEC.
```

In some preferred embodiments, the antibody of the invention comprises a light chain comprising an amino acid sequence of SEQ ID NO:3:

```
MGWSCIILFLVATATGVHSDIQLTQSPSSLSASVGDRVTITCSVSS
SISSNNLHWYQQKPGKAPKPWIYGTSNLASGVPSRFSGSGSGTDYT
FTISSLQPEDIATYYCQQWSSYPYMYTFGQGTKVEIKRTVAAPSVF
IFPPSDEQLKSGTASVVCLLNNFYPREAKVQWKVDNALQSGNSQES
VTEQDSKDSTYSLSSTLTLSKADYEKHKVYACEVTHQGLSSPVTKS
FNRGEC
```

(leader sequence underlined).

Also within the scope of the invention are antibodies comprising a heavy chain comprising an amino acid sequence of SEQ ID NO:4:

```
EVQLVESGGGVVQPGRSLRLSCSASGFTFSGYGLSWVRQAPGKGLE

WVAMISSGGSYTYYADSVKGRFAISRDNAKNTLFLQMDSLRPEDTG

VYFCARHGDDPAWFAYWGQGTPVTVSS.
```

In some preferred embodiments of the invention, the antibodies of the invention comprise a heavy chain comprising an amino acid sequence of SEQ ID NO:5:

```
EVQLVESGGGVVQPGRSLRLSCSASGFTFSGYGLSWVRQAPGKGLE

WVAMISSGGSYTYYADSVKGRFAISRDNAKNTLFLQMDSLRPEDTG

VYFCARHGDDPAWFAYWGQGTPVTVSSASTKGPSVFPLAPSSKSTS

GGTAALGCLVKDYFPEPVTVSWNSGALTSGVHTFPAVLQSSGLYSL

SSVVTVPSSSLGTQTYICNVNHKPSNTKVDKKVEPKSCDKTHTCPP

CPAPELLGGPSVFLFPPKPKDTLMISRTPEVTCVVVDVSHEDPEVK

FNWYVDGVEVHNAKTKPREEQYNSTYRVVSVLTVLHQDWLNGKEYK

CKVSNKALPAPIEKTISKAKGQPREPQVYTLPPSRDELTKNQVSLT

CLVKGFYPSDIAVEWESNGQPENNYKTTPPVLDSDGSFFLYSKLTV

DKSRWQQGNVFSCSVMHEALHNHYTQKSLSLSPGK.
```

In some preferred embodiments of the invention, the heavy chain of the antibody comprises an amino acid sequence of SEQ ID NO:6:

```
MGWSCIILFLVATATGVHSEVQLVESGGGVVQPGRSLRLSCSASGFT

FSGYGLSWVRQAPGKGLEWVAMISSGGSYTYYADSVKGRFAISRDNA

KNTLFLQMDSLRPEDTGVYFCARHGDDPAWFAYWGQGTPVTVSSAST

KGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTV

LHQDWLNGKEYKCKVSNKALPAPIEKTISKAKGQPREPQVYTLPPSR

DELTKNQVSLTCLVKGFYPSDIAVEWESNGQPENNYKTTPPVLDSDG

SFFLYSKLTVDKSRWQQGNVFSCSVMHEALHNHYTQKSLSLSPGK
```

(leader sequence underlined).

In some embodiments of the invention, the antibody comprises a heavy chain comprising an amino acid sequence of SEQ ID NO:4, 5, or 6 and a light chain comprising an amino acid sequence of SEQ ID NO:1, 2, or 3. In more preferred embodiments, the antibody comprises a heavy chain comprising an amino acid sequence of SEQ ID NO:5 and a light chain comprising an amino acid sequence of SEQ ID NO:2. In some embodiments of the invention, the antibody comprises a heavy chain comprising an amino acid sequence SEQ ID NO:6 and a light chain comprising an amino acid sequence of SEQ ID NO:3.

The antibodies of the invention are preferably nontoxic as demonstrated, for example, in vivo toxicology studies.

The antibodies and derivatives thereof of the invention have binding affinities that include a dissociation constant ($K_d$) of less than $1\times10^{-2}$. In some embodiments, the $K_d$ is less than $1\times10^{-3}$. In other embodiments, the $K_d$ is less than $1\times10^{-4}$. In some embodiments the $K_d$ is less than $1\times10^{-5}$. In still other embodiments, the $K_d$ is less than $1\times10^{-6}$. In other embodiments, the $K_d$ is less than $1\times10^{-7}$. In other embodiments, the $K_d$ is less than $1\times10^{-8}$. In other embodiments, the $K_d$ is less than $1\times10^{-9}$. In other embodiments, the $K_d$ is less than $1\times10^{-10}$. In still other embodiments, the $K_d$ is less than $1\times10^{-11}$. In some embodiments, the $K_d$ is less than $1\times10^{-12}$. In other embodiments, the $K_d$ is less than $1\times10^{-13}$. In other embodiments, the $K_d$ is less than $1\times10^{-14}$. In still other embodiments, the $K_d$ is less than $1\times10^{-15}$.

Without wishing to be bound by any particular theory, it is believed that the antibodies of some embodiments of the invention are particularly useful in binding the multimeric form of FR-α due to an increased avidity of the antibody as both "arms" of the antibody (Fab fragments) bind to separate FR-α molecules that make up the multimer. This leads to a decrease in the dissociation ($K_d$) of the antibody and an overall increase in the observed affinity ($K_D$).

Nucleic Acids

The invention also includes nucleic acids encoding the heavy chain and/or light chain of the anti-FR-α antibodies of the invention. "Nucleic acid" or a "nucleic acid molecule" as used herein refers to any DNA or RNA molecule, either single- or double-stranded and, if single-stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. In some embodiments of the invention, nucleic acids are "isolated." This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

Nucleic acids of the invention include nucleic acids having at least 80%, more preferably at least about 90%, more preferably at least about 95%, and most preferably at least about 98% homology to nucleic acids of the invention. The terms "percent similarity", "percent identity" and "percent homology" when referring to a particular sequence are used as set forth in the University of Wisconsin GCG software program. Nucleic acids of the invention also include complementary nucleic acids. In some instances, the sequences will be fully complementary (no mismatches) when aligned. In other instances, there may be up to about a 20% mismatch in the sequences.

Nucleic acids of the invention also include fragments of the nucleic acids of the invention. A "fragment" refers to a nucleic acid sequence that is preferably at least about 10 nucleic acids in length, more preferably about 40 nucleic acids, and most preferably about 100 nucleic acids in length. A "fragment" can also mean a stretch of at least about 100 consecutive nucleotides that contains one or more deletions, insertions, or substitutions. A "fragment" can also mean the whole coding sequence of a gene and may include 5' and 3' untranslated regions.

The encoded antibody light chain preferably comprises an amino acid sequence of SEQ ID NO:1, 2, or 3. The encoded antibody heavy chain preferably comprises an amino acid sequence of SEQ ID NO:4, 5, or 6. In some embodiments of the invention, the heavy chain of the antibody is encoded by a nucleic acid comprising the nucleotide sequence of SEQ ID NO:7:

```
ATGGGATGGAGCTGTATCATCCTCTTCTTGGTAGCAACAGCTAC

AGGTGTCCACTCCGAGGTCCAACTGGTGGAGAGCGGTGGAGGTG

TTGTGCAACCTGGCCGGTCCCTGCGCCTGTCCTGCTCCGCATCT

GGCTTCACCTTCAGCGGCTATGGGTTGTCTTGGGTGAGACAGGC

ACCTGGAAAAGGTCTTGAGTGGGTTGCAATGATTAGTAGTGGTG

GTAGTTATACCTACTATGCAGACAGTGTGAAGGGTAGATTTGCA

ATATCGCGAGACAACGCCAAGAACACATTGTTCCTGCAAATGGA

CAGCCTGAGACCCGAAGCACCGGGGTCTATTTTTGTGCAAGAC

ATGGGGACGATCCCGCCTGGTTCGCTTATTGGGGCCAAGGGACC

CCGGTCACCGTCTCCTCAGCCTCCACCAAGGGCCCATCGGTCTT

CCCCCTGGCACCCTCCTCCAAGAGCACCTCTGGGGGCACAGCGG

CCCTGGGCTGCCTGGTCAAGGACTACTTCCCCGAACCGGTGACG

GTGTCGTGGAACTCAGGCGCCCTGACCAGCGGCGTGCACACCTT

CCCGGCTGTCCTACAGTCCTCAGGACTCTACTCCCTCAGCAGCG

TGGTGACCGTGCCCTCCAGCAGCTTGGGCACCCAGACCTACATC

TGCAACGTGAATCACAAGCCCAGCAACACCAAGGTGGACAAGAA

AGTTGAGCCCAAATCTTGTGACAAAACTCACACATGCCCACCGT

GCCCAGCACCTGAACTCCTGGGGGGACCGTCAGTCTTCCTCTTC

CCCCCAAAACCCAAGGACACCCTCATGATCTCCCGGACCCCTGA

GGTCACATGCGTGGTGGTGGACGTGAGCCACGAAGACCCTGAGG

TCAAGTTCAACTGGTACGTGGACGGCGTGGAGGTGCATAATGCC

AAGACAAAGCCGCGGGAGGAGCAGTACAACAGCACGTACCGTGT

GGTCAGCGTCCTCACCGTCCTGCACCAGGACTGGCTGAATGGCA

AGGAGTACAAGTGCAAGGTCTCCAACAAAGCCCTCCCAGCCCCC

ATCGAGAAAACCATCTCCAAAGCCAAAGGGCAGCCCCGAGAACC

ACAGGTGTACACCCTGCCCCCATCCCGGGATGAGCTGACCAAGA

ACCAGGTCAGCCTGACCTGCCTGGTCAAAGGCTTCTATCCCAGC

GACATCGCCGTGGAGTGGGAGAGCAATGGGCAGCCGGAGAACAA

CTACAAGACCACGCCTCCCGTGCTGGACTCCGACGGCTCCTTCT

TCCTCTACAGCAAGCTCACCGTGGACAAGAGCAGGTGGCAGCAG

GGGAACGTCTTCTCATGCTCCGTGATGCATGAGGCTCTGCACAA

CCACTACACGCAGAAGAGCCTCTCCCTGTCTCCCGGGAAATGA.
```

In some embodiments of the invention, the light chain of the anti-folate receptor-α antibody is encoded by a nucleic acid sequence of SEQ ID NO:8:

```
ATGGGATGGAGCTGTATCATCCTCTTCTTGGTAGCAACAGCTA

CAGGTGTCCACTCCGACATCCAGCTGACCCAGAGCCCAAGCAG

CCTGAGCGCCAGCGTGGGTGACAGAGTGACCATCACCTGTAGT

GTCAGCTCAAGTATAAGTTCCAACAACTTGCACTGGTACCAGC

AGAAGCCAGGTAAGGCTCCAAAGCCATGGATCTACGGCACATC

CAACCTGGCTTCTGGTGTGCCAAGCAGATTCAGCGGTAGCGGT

AGCGGTACCGACTACACCTTCACCATCAGCAGCCTCCAGCCAG

AGGACATCGCCACCTACTACTGCCAACAGTGGAGTAGTTACCC

GTACATGTACACGTTCGGCCAAGGGACCAAGGTGGAAATCAAA

CGAACTGTGGCTGCACCATCTGTCTTCATCTTCCCGCCATCTG

ATGAGCAGTTGAAATCTGGAACTGCCTCTGTTGTGTGCCTGCT

GAATAACTTCTATCCCAGAGAGGCCAAAGTACAGTGGAAGGTG

GATAACGCCCTCCAATCGGGTAACTCCCAGGAGAGTGTCACAG

AGCAGGACAGCAAGGACAGCACCTACAGCCTCAGCAGCACCCT

GACGCTGAGCAAAGCAGACTACGAGAAACACAAAGTCTACGCC

TGCGAAGTCACCCATCAGGGCCTGAGCTCGCCCGTCACAAAGA

GCTTCAACAGGGGAGAGTGTTAA.
```

In some embodiments of the invention are provided nucleic acids encoding both a heavy chain and a light chain of an antibody of the invention. For example, a nucleic acid of the invention may comprise a nucleic acid sequence encoding an amino acid sequence of SEQ ID NO:1, 2, or 3 and a nucleic acid sequence encoding an amino acid sequence of SEQ ID NO:4, 5, or 6.

Nucleic acids of the invention can be cloned into a vector. A "vector" is a replicon, such as a plasmid, cosmid, bacmid, phage, artificial chromosome (BAC, YAC) or virus, into which another genetic sequence or element (either DNA or RNA) may be inserted so as to bring about the replication of the attached sequence or element. A "replicon" is any genetic element, for example, a plasmid, cosmid, bacmid, phage, artificial chromosome (BAC, YAC) or virus, that is capable of replication largely under its own control. A replicon may be either RNA or DNA and may be single or double stranded. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. Expression vectors of the invention may further comprise regulatory sequences, for example, an internal ribosomal entry site. The expression vector can be introduced into a cell by transfection, for example.

Methods of Producing Antibodies to FR-α

The invention also provides methods of producing monoclonal antibodies that specifically bind FR-α. Antibodies of the invention may be produced in vivo or in vitro. One strategy for generating antibodies against FR-α involves immunizing animals with FR-α. In some embodiments, animals are immunized with the monomeric or multimeric form of FR-α. Animals so immunized will produce antibodies against the protein. Standard methods are known for creating monoclonal antibodies including, but are not limited to, the hybridoma technique (see Kohler & Milstein, (1975) *Nature* 256:495-497); the trioma technique; the human B-cell hybridoma technique (see Kozbor et al. (1983) *Immunol. Today* 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

FR-α may be purified from cells or from recombinant systems using a variety of well-known techniques for isolating and purifying proteins. For example, but not by way of limitation, FR-α may be isolated based on the apparent molecular weight of the protein by running the protein on an SDS-PAGE gel and blotting the proteins onto a membrane. Thereafter, the appropriate size band corresponding to FR-α may be cut from the membrane and used as an immunogen in animals directly, or by first extracting or eluting the protein from the membrane. As an alternative example, the protein may be isolated by size-exclusion chromatography alone or in combination with other means of isolation and purification.

The invention also provides methods of producing monoclonal antibodies that specifically bind to the multimeric form of FR-α. Multimeric, for example tetrameric, FR-α may be purified from cells or from recombinant systems using a variety of well-known techniques for isolating and purifying proteins. For example, but not by way of limitation, multimeric FR-α may be isolated based on the apparent molecular weight of the protein by running the protein on an SDS-PAGE gel and blotting the proteins onto a membrane. Thereafter, the appropriate size band corresponding to the multimeric form of FR-α may be cut from the membrane and used as an immunogen in animals directly, or by first extracting or eluting the protein from the membrane. As an alternative example, the protein may be isolated by size-exclusion chromatography alone or in combination with other means of isolation and purification.

Other means of purification are available in such standard reference texts as Zola, MONOCLONAL ANTIBODIES: PREPARATION AND USE OF MONOCLONAL ANTIBODIES AND ENGINEERED ANTIBODY DERIVATIVES (BASICS: FROM BACKGROUND TO BENCH) Springer-Verlag Ltd., New York, 2000; BASIC METHODS IN ANTIBODY PRODUCTION AND CHARACTERIZATION, Chapter 11, "Antibody Purification Methods," Howard and Bethell, Eds., CRC Press, 2000; ANTIBODY ENGINEERING (SPRINGER LAB MANUAL.), Kontermann and Dubel, Eds., Springer-Verlag, 2001.

For in vivo antibody production, animals are generally immunized with FR-α or an immunogenic portion of FR-α. The antigen is generally combined with an adjuvant to promote immunogenicity. Adjuvants vary according to the species used for immunization. Examples of adjuvants include, but are not limited to: Freund's complete adjuvant ("FCA"), Freund's incomplete adjuvant ("FIA"), mineral gels (e.g., aluminum hydroxide), surface active substances (e.g., lysolecithin, pluronic polyols, polyanions), peptides, oil emulsions, keyhole limpet hemocyanin ("KLH"), dinitrophenol ("DNP"), and potentially useful human adjuvants such as Bacille Calmette-Guerin ("BCG") and *corynebacterium parvum*. Such adjuvants are also well known in the art.

Immunization may be accomplished using well-known procedures. The dose and immunization regimen will depend on the species of mammal immunized, its immune status, body weight, and/or calculated surface area, etc. Typically, blood serum is sampled from the immunized mammals and assayed for anti-FR-α antibodies using appropriate screening assays as described below, for example.

A common method for producing humanized antibodies is to graft CDR sequences from a MAb (produced by immunizing a rodent host) onto a human Ig backbone, and transfection of the chimeric genes into Chinese Hamster Ovary (CHO) cells which in turn produce a functional Ab that is secreted by the CHO cells (Shields, R. L., et al. (1995) Anti-IgE monoclonal antibodies that inhibit allergen-specific histamine release. *Int Arch. Allergy Immunol.* 107:412-413). The methods described within this application are also useful for generating genetic alterations within Ig genes or chimeric Igs transfected within host cells such as rodent cell lines, plants, yeast and prokaryotes (Frigerio L, et al. (2000) Assembly, secretion, and vacuolar delivery of a hybrid immunoglobulin in plants. *Plant Physiol.* 123:1483-1494).

Splenocytes from immunized animals may be immortalized by fusing the splenocytes (containing the antibody-producing B cells) with an immortal cell line such as a myeloma line. Typically, myeloma cell line is from the same species as the splenocyte donor. In one embodiment, the immortal cell line is sensitive to culture medium containing hypoxanthine, aminopterin and thymidine ("HAT medium"). In some embodiments, the myeloma cells are negative for Epstein-Barr virus (EBV) infection. In preferred embodiments, the myeloma cells are HAT-sensitive, EBV negative and Ig expression negative. Any suitable myeloma may be used. Murine hybridomas may be generated using mouse myeloma cell lines (e.g., the P3-NS1/1-Ag4-1, P3-x63-Ag8.653 or Sp2/O-Ag14 myeloma lines). These murine myeloma lines are available from the ATCC. These myeloma cells are fused to the donor splenocytes polyethylene glycol ("PEG"), preferably 1500 molecular weight polyethylene glycol ("PEG 1500"). Hybridoma cells resulting from the fusion are selected in HAT medium which kills unfused and unproductively fused myeloma cells. Unfused splenocytes die over a short period of time in culture. In some embodiments, the myeloma cells do not express immunoglobulin genes.

Hybridomas producing a desired antibody which are detected by screening assays such as those described below may be used to produce antibodies in culture or in animals. For example, the hybridoma cells may be cultured in a nutrient medium under conditions and for a time sufficient to allow the hybridoma cells to secrete the monoclonal antibodies into the culture medium. These techniques and culture media are well known by those skilled in the art. Alternatively, the hybridoma cells may be injected into the peritoneum of an unimmunized animal. The cells proliferate in the peritoneal cavity and secrete the antibody, which accumulates as ascites fluid. The ascites fluid may be withdrawn from the peritoneal cavity with a syringe as a rich source of the monoclonal antibody.

Another non-limiting method for producing human antibodies is described in U.S. Pat. No. 5,789,650 which describes transgenic mammals that produce antibodies of another species (e.g., humans) with their own endogenous immunoglobulin genes being inactivated. The genes for the heterologous antibodies are encoded by human immunoglobulin genes. The transgenes containing the unrearranged immunoglobulin encoding regions are introduced into a non-human animal. The resulting transgenic animals are capable of functionally rearranging the transgenic immunoglobulin sequences and producing a repertoire of antibodies of various isotypes encoded by human immunoglobulin genes. The B-cells from the transgenic animals are subsequently immortalized by any of a variety of methods, including fusion with an immortalizing cell line (e.g., a myeloma cell).

Antibodies against FR-α may also be prepared in vitro using a variety of techniques known in the art. For example, but not by way of limitation, fully human monoclonal antibodies against FR-α may be prepared by using in vitro-primed human splenocytes (Boerner et al. (1991) *J. Immunol.* 147:86-95).

Alternatively, for example, the antibodies of the invention may be prepared by "repertoire cloning" (Persson et al. (1991) *Proc. Nat. Acad. Sci. USA* 88:2432-2436; and Huang and Stollar (1991) *J. Immunol. Methods* 141:227-236). Further, U.S. Pat. No. 5,798,230 describes preparation of human monoclonal antibodies from human B antibody-producing B cells that are immortalized by infection with an Epstein-Barr virus that expresses Epstein-Barr virus nuclear antigen 2 (EBNA2). EBNA2, required for immortalization, is then inactivated resulting in increased antibody titers.

In another embodiment, antibodies against FR-α are formed by in vitro immunization of peripheral blood mononuclear cells ("PBMCs"). This may be accomplished by any means known in the art, such as, for example, using methods described in the literature (Zafiropoulos et al. (1997) *J. Immunological Methods* 200:181-190).

Methods for producing antibody-producing cells of the invention also include methods for developing hypermutable antibody-producing cells by taking advantage of the conserved mismatch repair (MMR) process of host cells. Dominant negative alleles of such genes, when introduced into cells or transgenic animals, increase the rate of spontaneous mutations by reducing the effectiveness of DNA repair and thereby render the cells or animals hypermutable. Blocking MMR in antibody-producing cells such as but not limited to: hybridomas; mammalian cells transfected with genes encoding for Ig light and heavy chains; mammalian cells transfected with genes encoding for single chain antibodies; eukaryotic cells transfected with Ig genes, can enhance the rate of mutation within these cells leading to clones that have enhanced antibody production, cells containing genetically altered antibodies with enhanced biochemical properties such as increased antigen binding, cells that produce antibodies comprising substantially only the antibody of the invention, and/or cells that are substantially free of FR-α binding competitors. The process of MMR, also called mismatch proofreading, is carried out by protein complexes in cells ranging from bacteria to mammalian cells. A MMR gene is a gene that encodes for one of the proteins of such a mismatch repair complex. Although not wanting to be bound by any particular theory of mechanism of action, a MMR complex is believed to detect distortions of the DNA helix resulting from non-complementary pairing of nucleotide bases. The non-complementary base on the newer DNA strand is excised, and the excised base is replaced with the appropriate base, which is complementary to the older DNA strand. In this way, cells eliminate many mutations that occur as a result of mistakes in DNA replication.

Dominant negative alleles cause a MMR defective phenotype even in the presence of a wild-type allele in the same cell. An example of a dominant negative allele of a MMR gene is the human gene hPMS2-134, which carries a truncating mutation at codon 134. The mutation causes the product of this gene to abnormally terminate at the position of the 134th amino acid, resulting in a shortened polypeptide containing the N-terminal 133 amino acids. Such a mutation causes an increase in the rate of mutations, which accumulate in cells after DNA replication. Expression of a dominant negative allele of a mismatch repair gene results in impairment of mismatch repair activity, even in the presence of the wild-type allele. Any allele which produces such effect can be used in this invention. Dominant negative alleles of a MMR gene can be obtained from the cells of humans, animals, yeast, bacteria, or other organisms. Such alleles can be identified by screening cells for defective MMR activity. Cells from animals or humans with cancer can be screened for defective mismatch repair. Cells from colon cancer patients may be particularly useful. Genomic DNA, cDNA, or mRNA from any cell encoding a MMR protein can be analyzed for variations from the wild type sequence. Dominant negative alleles of a MMR gene can also be created artificially, for example, by producing variants of the hPMS2-134 allele or other MMR genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele. Examples of mismatch repair proteins and nucleic acid sequences include mouse PMS2 (SEQ ID NOs:9 and 10), human PMS2 (SEQ ID NOs:11 and 12), human PMS1 (SEQ ID NOs:13 and 14), human MSH2 (SEQ ID NOs: 15 and 16), human MLH1 (SEQ ID NOs:17 and 18), and human PMS2-134 (SEQ ID NOs:19 and 20).

A cell into which a dominant negative allele of a mismatch repair gene has been introduced will become hypermutable. This means that the spontaneous mutation rate of such cells or animals is elevated compared to cells or animals without such alleles. The degree of elevation of the spontaneous mutation rate can be at least 2-fold, 5-fold, 10-fold, 20-fold, 50-fold, 100-fold, 200-fold, 500-fold, or 1000-fold that of the normal cell or animal. The use of chemical mutagens such as but limited to methane sulfonate, dimethyl sulfonate, 06-methyl benzadine, MNU, ENU, etc. can be used in MMR defective cells to increase the rates an additional 10 to 100 fold that of the MMR deficiency itself.

According to one aspect of the invention, a polynucleotide encoding a dominant negative form of a MMR protein is introduced into a cell. Preferably the cell produces anti-FR-α antibodies. In some embodiments, the cells produce an antibody comprising a heavy chain comprising an amino acid sequence of SEQ ID NO:4, 5, or 6 and a light chain comprising an amino acid sequence of SEQ ID NO:1, 2, or 3. In some preferred embodiments, the cells comprise a nucleic acid comprising a nucleotide sequence of SEQ ID NO:7 and/or a nucleotide sequence of SEQ ID NO:8. The dominant negative MMR gene can be any dominant negative allele encoding a protein which is part of a MMR complex, for example, PMS2, PMS1, MLH1, or MSH2. The dominant negative allele can be naturally occurring or made in the laboratory. The polynucleotide can be in the form of genomic DNA, cDNA, RNA, or a chemically synthesized polynucleotide.

The polynucleotide can be cloned into an expression vector containing a constitutively active promoter segment (such as but not limited to CMV, SV40, Elongation Factor or LTR sequences) or an inducible promoter sequence such as the steroid inducible pIND vector (Invitrogen), where the expression of the dominant negative MMR gene can be regulated. The polynucleotide can be introduced into the cell by transfection.

According to another aspect of the invention, an immunoglobulin (Ig) gene, a set of Ig genes or a chimeric gene containing whole or parts of an Ig gene can be transfected into MMR-deficient cell hosts, the cell is grown and screened for clones with new phenotypes and/or genotypes. MMR-defective cells may be of human, primates, mammals, rodent, plant, yeast or of the prokaryotic kingdom. The gene encoding the Ig of the cell with the new phenotype or genotype may be isolated from the respective clone and introduced into genetically stable cells (i.e., cells with normal MMR) to provide clones that consistently produce the Ig. The method of isolating the Ig gene may be any method known in the art. Introduction of the isolated polynucleotide encoding the Ig may also be performed using any method known in the art, including, but not limited to transfection of an expression vector containing the polynucleotide encoding the Ig. As an alternative to transfecting an Ig gene, a set of Ig genes or a chimeric gene containing whole or parts of an Ig gene into an MMR-deficient host cell, such Ig genes may be transfected simultaneously with a gene encoding a dominant negative mismatch repair gene into a genetically stable cell to render the cell hypermutable.

Transfection is any process whereby a polynucleotide is introduced into a cell. The process of transfection can be carried out in a living animal, e.g., using a vector for gene therapy, or it can be carried out in vitro, e.g., using a suspension of one or more isolated cells in culture. The cell can be any type of eukaryotic cell, including, for example, cells isolated from humans or other primates, mammals or other vertebrates, invertebrates, and single celled organisms such as protozoa, yeast, or bacteria.

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known. Available techniques for introducing polynucleotides include but are not limited to electroporation, transduction, cell fusion, the use of calcium chloride, and packaging of the polynucleotide together with lipid for fusion with the cells of interest. Once a cell has been transfected with the MMR gene, the cell can be grown and reproduced in culture. If the transfection is stable, such that the gene is expressed at a consistent level for many cell generations, then a cell line results.

Upon identification of the desired phenotype or trait the organism can then be genetically stabilized. Cells expressing the dominant negative alleles can be "cured" in that the dominant negative allele can be turned off, if inducible, eliminated from the cell, and the like such that the cells become genetically stable and no longer accumulate mutations at the abnormally high rate.

Figure 4:
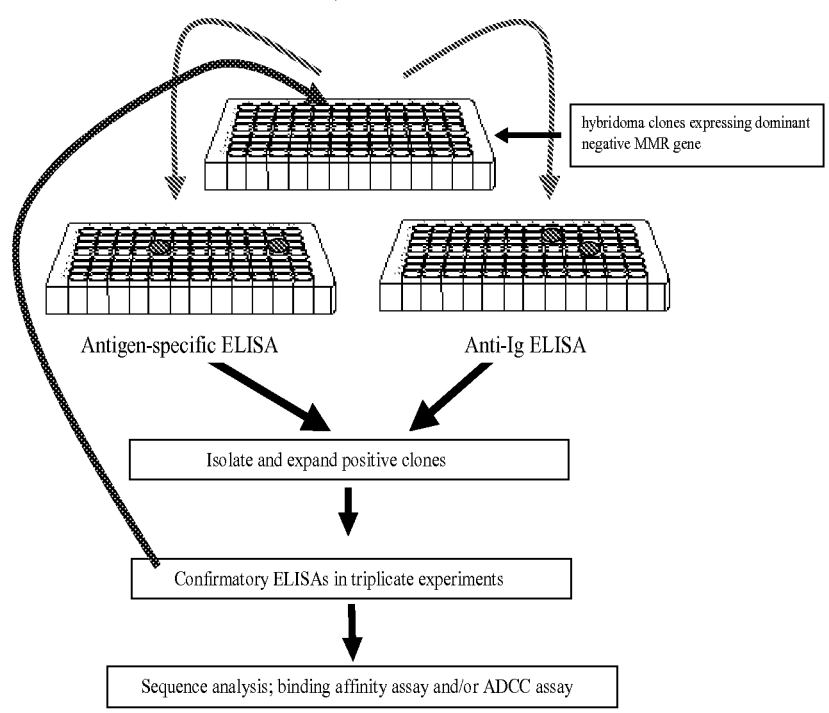
FIG. 4 illustrates a screening method for identifying antibody-producing cells of the invention.

Cells that produce substantially only anti-FR-α antibodies of the invention or cells that are substantially free of FR-α binding competitors are selected for cloning and expansion according to the methods for determining antibody specificity described herein. An example of such a method is illustrated in FIG. 4.

Nucleic acids encoding antibodies of the invention may be recombinantly expressed. The expression cells of the invention include any insect expression cell line known, such as for example, *Spodoptera frugiperda* cells. The expression cell lines may also be yeast cell lines, such as, for example, *Saccharomyces cerevisiae* and *Schizosaccharomyces pombe* cells. The expression cells may also be mammalian cells such as, for example, hybridoma cells (e.g., NS0 cells), Chinese hamster ovary cells, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK31 cells, mouse sertoli cells, human cervical carcinoma cells, buffalo rat liver cells, human lung cells, human liver cells, mouse mammary tumor cells, TRI cells, MRC 5 cells, and FS4 cells. Nucleic acids of the invention may be introduced into cell by transfection, for example. Recombinantly expressed antibodies may be recovered from the growth medium of the cells, for example.

In one embodiment of the invention, the procedure for in vitro immunization is supplemented with directed evolution of the hybridoma cells in which a dominant negative allele of a mismatch repair gene such as PMS1, PMS2, PMS2-134, PMSR2, PMSR3, MLH1, MLH2, MLH3, MLH4, MLH5, MLH6, PMSL9, MSH1, and MSH2 is introduced into the hybridoma cells after fusion of the splenocytes, or to the myeloma cells before fusion. Cells containing the dominant negative mutant will become hypermutable and accumulate mutations at a higher rate than untransfected control cells. A pool of the mutating cells may be screened, for example, for clones that are substantially free of FR-α binding competitors, clones that produce higher affinity antibodies, clones that produce higher titers of antibodies, or clones that simply grow faster or better under certain conditions. The technique for generating hypermutable cells using dominant negative alleles of mismatch repair genes is described, for example, in U.S. Pat. No. 6,808,894. Alternatively, mismatch repair may be inhibited using the chemical inhibitors of mismatch repair described by Nicolaides et al. in WO 02/054856 "Chemical Inhibitors of Mismatch Repair" published Jul. 18, 2002. The technique for enhancing antibodies using the dominant negative alleles of mismatch repair genes or chemical inhibitors of mismatch repair may be applied to mammalian expression cells expressing cloned immunoglobulin genes as well. Cells expressing the dominant negative alleles can be "cured" in that the dominant negative allele can be turned off if inducible, inactivated, eliminated from the cell, and the like, such that the cells become genetically stable once more and no longer accumulate mutations at the abnormally high rate.

Screening for Antibody Specificity

Screening for antibodies that specifically bind to FR-α may be accomplished using an enzyme-linked immunosorbent assay (ELISA) in which microtiter plates are coated with FR-α. In some embodiments, antibodies that bind FR-α from positively reacting clones can be further screened for reactivity in an ELISA-based assay to other folate receptor isoforms, for example, FR-β and/or FR-γ, using microtiter plates coated with the other folate receptor isoform(s). Clones that produce antibodies that are reactive to another isoform of folate receptor are eliminated, and clones that produce antibodies that are reactive to FR-α only may be selected for further expansion and development. Confirmation of reactivity of the antibodies to FR-α may be accomplished, for example, using a Western Blot assay in which protein from ovarian, breast, renal, colorectal, lung, endometrial, or brain cancer cells and purified FR-α and other folate receptor isoforms are run on an SDS-PAGE gel, and subsequently are blotted onto a membrane. The membrane may then be probed with the putative anti-FR-α antibodies. Reactivity with FR-α and not another folate receptor isoform confirms specificity of reactivity for FR-α.

In some embodiments, the binding affinity of anti-FR-α antibodies is determined Antibodies of the invention preferably have a binding affinity to FR-α of at least about $1 \times 10^{-7}$ M, more preferably at least about $1 \times 10^{-8}$ M, more preferably at least about $1 \times 10^{-9}$ M, and most preferably at least about $1 \times 10^{-10}$ M. Preferred antibody-producing cells of the invention produce substantially only antibodies having a binding affinity to FR-α of at least about $1\times10^{-7}$ M, more preferably at least about $1\times10^{-8}$ M, more preferably at least about $1\times10^{-9}$ M, and most preferably at least about $1\times10^{-10}$ M. Preferred compositions of the invention comprise substantially only antibodies having a binding affinity to FR-α of at least about $1\times10^{-7}$ M, more preferably at least about $1\times10^{-8}$ M, more preferably at least about $1\times10^{-9}$ M, and most preferably at least about $1\times10^{-10}$ M.

In some embodiments, antibodies that bind the multimeric form of FR-α from positively reacting clones can be further screened for reactivity in an ELISA-based assay to the monomeric form of FR-α using microtiter plates coated with the monomeric form of FR-α. Clones that produce antibodies that are reactive to the monomeric form of FR-α are eliminated, and clones that produce antibodies that are reactive to the multimeric form only may be selected for further expansion and development. Confirmation of reactivity of the antibodies to the multimeric form of FR-α may be accomplished, for example, using a Western Blot assay in which protein from ovarian, breast, renal, colorectal, lung, endometrial, or brain cancer cells and purified multimeric and monomeric FR-α are run on an SDS-PAGE gel under reducing and non-reducing conditions, and subsequently are blotted onto a membrane. The membrane may then be probed with the putative anti-multimeric FR-α antibodies. Reactivity with the appropriately sized multimeric form of FR-α under non-reducing conditions and not the 38 kDa form of FR-α (under reducing or non-reducing conditions) confirms specificity of reactivity for the multimeric form of FR-α.

The antibodies of the invention preferably induce antibody-dependent cellular cytotoxicity (ADCC) in FR-α bearing cells. ADCC assays are known in the art. The method of the invention enabled successful production of an optimized, humanized anti-FR-α antibody with acceptable antigen binding activity (low nanomolar dissociation constant) and production rates (>10 pg/cell/day). ADCC assays using human ovarian cancer cells as target and peripheral blood mononuclear cells (PBMCs) as effector cells showed that 200 ng/ml of antibody of the invention produced in CHO cells mediated the lysis of 32% of target cells whereas lysis mediated by control $IgG_1/\kappa$ antibody was only 6% (paired T test=0.0008).

Anti-FR-α Antibody-Producing Cells

Antibody-producing cells of the invention include any insect expression cell line known, such as for example, *Spodoptera frugiperda* cells. The expression cell lines may also be yeast cell lines, such as, for example, *Saccharomyces cerevisiae* and *Schizosaccharomyces pombe* cells. The expression cells may also be mammalian cells such as, for example, hybridoma cells (e.g., NS0 cells), Chinese hamster ovary cells, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK31 cells, mouse sertoli cells, human cervical carcinoma cells, buffalo rat liver cells, human lung cells, human liver cells, mouse mammary tumor cells, TRI cells, MRC 5 cells, and FS4 cells.

In some preferred embodiments, the antibody-producing cells of the invention produce antibodies that specifically bind to FR-α. The cells preferably are substantially free of FR-α binding competitors. In preferred embodiments, the antibody-producing cells comprise less than about 10%, preferably less than about 5%, more preferably less than about 1%, more preferably less than about 0.5%, more preferably less than about 0.1%, and most preferably 0% by weight FR-α binding competitors. In some preferred embodiments, the antibodies produced by the antibody-producing cells are substantially free of FR-α binding competitors. In preferred embodiments, antibodies produced by the antibody-producing cells comprise less than about 10%, preferably less than about 5%, more preferably less than about 1%, more preferably less than about 0.5%, more preferably less than about 0.1%, and most preferably 0% by weight FR-α binding competitors. Preferred antibody-producing cells of the invention produce substantially only antibodies having a binding affinity to FR-α of at least about $1\times10^{-7}$ M, more preferably at least about $1\times10^{-8}$M, more preferably at least about $1\times10^{-9}$ M, and most preferably at least about $1\times10^{-10}$ M.

Antibody Purification

Methods of antibody purification are known in the art. In some embodiments of the invention, methods for antibody purification include filtration, affinity column chromatography, cation exchange chromatography, anion exchange chromatography, and concentration. The filtration step preferably comprises ultrafiltration, and more preferably ultrafiltration and diafiltration. Filtration is preferably performed at least about 5-50 times, more preferably 10 to 30 times, and most preferably 14 to 27 times. Affinity column chromatography, may be performed using, for example, PROSEP Affinity Chromatography (Millipore, Billerica, Massachusetts). In a preferred embodiment, the affinity chromatography step comprises PROSEP-VA column chromatography. Eluate may be washed in a solvent detergent. Cation exchange chromatography may include, for example, SP-Sepharose Cation Exchange Chromatography. Anion exchange chromatography may include, for example but not limited to, Q-Sepharose Fast Flow Anion Exchange. The anion exchange step is preferably non-binding, thereby allowing removal of contaminants including DNA and BSA. The antibody product is preferably nanofiltered, for example, using a Pall DV 20 Nanofilter. The antibody product may be concentrated, for example, using ultrafiltration and diafiltration. The method may further comprise a step of size exclusion chromatography to remove aggregates.

Pharmaceutical Compositions of Antibodies

Another aspect of the invention features a pharmaceutical composition of anti-FR-α antibodies of the invention. The pharmaceutical compositions may be used to inhibit or reduce growth of tumor cells in a patient. The compositions of antibodies preferably are substantially free of FR-α binding competitors. In certain embodiments, the pharmaceutical composition is formulated for administration by injection or infusion.

Pharmaceutical compositions of the invention may further comprise a chemotherapeutic or cytotoxic agent. In some embodiments, the antibody is conjugated to the chemotherapeutic or cytotoxic agent. Suitable chemotherapeutic or cytotoxic agents include but are not limited to a radioisotope, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the agent is a toxin or cytotoxic drug, including but not limited to ricin, modified *Pseudomonas* enterotoxin A, calicheamicin, adriamycin, 5-fluorouracil, and the like. Pharmaceutical compositions of the invention may comprise an antifolate compound including but not limited to 5-fluoro-2'-deoxyuridine-5'-monophosphate (FdUMP), 5-fluorouracil, leucovorin, ZD1649, MTA, GW1843U89, ZD9331, AG337, and PT523.

Pharmaceutical compositions of the invention may be formulated with a pharmaceutically acceptable carrier or medium. Suitable pharmaceutically acceptable carriers include water, PBS, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences (17$^{th}$ Ed., Mack Pub. Co., Easton, Pa.).

Kits

According to yet another aspect of the invention, a kit is provided for inhibiting or reducing growth of tumor cells in a patient. Also provided are kits for identifying the presence of dysplastic cells in vitro or in vivo.

The kits of the invention comprise antibody or an antibody composition of the invention and instructions for using the kit in a method for inhibiting or reducing growth of tumor cells in the patient or in a method for identifying the presence of dysplastic cells, for example, in a biological sample. The kit may comprise at least one chemotherapeutic or cytotoxic reagent. The kit may comprise an antifolate compound. The kit may comprise at least one diagnostic reagent. An example of a diagnostic reagent is a detectable label, for example but not limited to a radioactive, fluorescent, or chromophoric agent (e.g., $^{111}$In-DOTA). The detectable label may comprise an enzyme. The kit may comprise instructions and/or means for administering the antibody or antibody composition, for example, by injection.

Methods of Detecting a Dysplastic Cell

The methods of the invention include methods of detecting dysplastic or cancer cells presenting FR-α on the surface, including but not limited to ovarian, breast, lung, endometrial, renal, colorectal, or brain carcinoma cells. The method may be performed in vitro on a biological sample or in vivo. Methods of detecting dysplastic cells according to the invention comprise contacting anti-FR-α antibody of the invention with a biological sample or administering anti-FR-α antibody of the invention to a patient, wherein the antibody is labeled with a detectable label, for example but not limited to a radioactive, fluorescent, or chromophoric agent (e.g., $^{111}$In-DOTA), and determining binding of the antibody to cells. The detectable label may be an enzyme.

Methods of Reducing the Growth of Tumor Cells

The methods of the invention are suitable for use in humans and non-human animals identified as having a neoplastic condition associated with an increased expression of FR-α. Non-human animals which benefit from the invention include pets, exotic (e.g., zoo animals), and domestic livestock. Preferably the non-human animals are mammals.

The invention is suitable for use in a human or animal patient that is identified as having a dysplastic disorder that is marked by increased expression of FR-α in the neoplasm in relation to normal tissues. Once such a patient is identified as in need of treatment for such a condition, the method of the invention may be applied to effect treatment of the condition. Tumors that may be treated include, but are not limited to ovarian, breast, renal, colorectal, lung, endometrial, brain, fallopian tube, or uterine tumors, and certain leukemia cells. In some embodiments, the tumor is cisplatin-resistant.

The antibodies and derivatives thereof for use in the invention may be administered orally in any acceptable dosage form such as capsules, tablets, aqueous suspensions, solutions or the like. The antibodies and derivatives thereof may also be administered parenterally including but not limited to: subcutaneous, intravenous, intramuscular, intra-articular, intra-synovial, intrasternal, intranasal, topically, intrathecal, intrahepatic, intralesional, and intracranial injection or infusion techniques. Generally, the antibodies will be intravenously or intraperitoneally, for example, by injection.

The antibodies and derivatives of the invention may be administered alone or with a pharmaceutically acceptable carrier, including acceptable adjuvants, vehicles and excipients, for example, phosphate buffered saline.

The antibodies and derivatives of the invention may also be administered with one or more antifolate compounds that are used to treat cancer. The antifolate compounds include, but are not limited to 5-fluoro-2'-deoxy-uridine-5'-monophosphate (FdUMP); 5-fluorouracil (5-FU); L-5-formyltetrahydrofolate ("leucovorin"); N-[5-(N-(3,4-dihydro-2-methyl-4-oxoquinazolin-6-yl-methyl)-amino)-2-thenyl)]-L-glutamic acid ("ZD1649"; also known as "Tomudex") (Jackman et al. (1991) Cancer Res. 51:5579-5586); N-(4-(2-(2-amino-4,7-dihydro-4-oxo-3H-pyrrolo[2,3-D]pyrimidin-5-yl)-ethyl)-benzoyl]-L-glutamic acid ("multi-targeted antifolate" (MTA) also known as "LY231514," "ALIMTA," and "Pemetrexed")(Taylor et al. (1992) J. Med. Chem. 35:4450-4454; Shih et al. (1997) Cancer Res. 57:1116-1123); (S)-2-(5)-(((1,2-dihydro-3-methyl-1-oxobenzo(f)quinazolin-9-yl)-methyl)-amino)-oxo-2-isoindolinyl)-glutaric acid ("GW1843U89") (Hanlon and Ferone (1996) Cancer Res. 56:3301-3306); (2S)-2-{O-fluoro-p-[N-(2,7-dimethyl-4-oxo-3,4-dihydro-quinazolin-6-yl-methyl)-N-prop-2-ynyl)amino]benzamido}-4-(tetrazol-5-yl)-butyric acid ("ZD9331") (Jackman et al. (1997) Clin. Cancer Res. 3:911-921); 3,4-dihydro-amino-6-methyl-4-oxo-5-(4-pyridylthio)-quinazoline ("AG337" also known as "Thymitaq") (Webber et al. (1996) Cancer Chemother. Pharmacol. 37:509-517; Rafi et al. (1998) J. Clin. Oncol. 16:1331-1341), and N$^{α}$-(4-amino-4-deoxypteroyl)-N$^{δ}$-(hemiphthaloyl-L-ornithine) ("PT523") (Rhee et al. (1994) Mol. Pharmacol. 45:783-791; Rowowsky (1999) Curr. Med. Chem. 6:329-352). The antifolate compounds may be administered before, after, or simultaneously with the anti-FR-α antibodies of the invention. The amounts of antifolate compounds to be administered may be the dosages currently used, or may be increased or decreased, as can readily be determined by a physician based on achieving decreased tumor growth or tumor elimination without causing any untoward effects on the patient.

The effective dosage will depend on a variety of factors. It is well within the purview of a skilled physician to adjust the dosage for a given patient according to various parameters such as body weight, the goal of treatment, the highest tolerated dose, the specific formulation used, the route of administration and the like. Generally, dosage levels of between about 5.88 mg/m$^2$ and about 294.12 mg/m$^2$ (i.e., 10 to 500 mg antibody) per day of the antibody or derivative thereof are suitable. In some embodiments, the dose will be about 29.41 mg/m$^2$ to about 176.47 mg/m$^2$ (i.e., 50 to 300 mg antibody) per day of the antibody or derivative thereof. In other embodiments, the dose will be about 58.82 mg/m$^2$ to about 147.06 mg/m$^2$ (i.e., 100 to 250 mg antibody) per day. In still other embodiments, the dose will be about 88.24 mg/m² to about 117.65 mg/m² (i.e., 150 to 200 mg antibody) per day. Dosing may be as a bolus or an infusion. Dosages may be given once a day or multiple times in a day. Further, dosages may be given multiple times of a period of time. In some embodiments, the doses are given every 1-14 days. In some embodiments, the antibodies or derivatives thereof are given as a dose of about 10 to 500 mg i.p. In other embodiments, the antibodies of derivatives thereof are provided at about 50 to 300 mg i.v. In still other embodiments, the antibodies or derivatives thereof are provided such that a plasma level of at least about 1 ug/ml is maintained.

Effective treatment may be assessed in a variety of ways. In one embodiment, effective treatment is determined by a slowed progression of tumor growth. In other embodiments, effective treatment is marked by shrinkage of the tumor (i.e., decrease in the size of the tumor determined, for example, using Response Evaluation Criteria in Solid Tumors (RE-CIST) available online through the National Cancer Institute Cancer Therapy Evaluation Program). In other embodiments, effective treatment is marked by inhibition of metastasis of the tumor. In still other embodiments, effective therapy is measured by increased well-being of the patient including such signs as weight gain, regained strength, decreased pain, thriving, and subjective indications from the patient of better health.

The following Examples are provided to illustrate the present invention, and should not be construed as limiting thereof.

EXAMPLES

Example 1

Generation of Anti-FR-α Antibody-Producing Cells

Murine antibody LK26 was raised against choriocarcinoma cell line Lu-75(c). LK26 was humanized by CDR grafting, yielding an IgG (IgG1/κ subtype) expressed in NS0 cell lines, according to the method of U.S. Pat. No. 6,124, 106. The NS0 cell line was transfected with a hPMS2-134 expression plasmid. The MMR gene was cloned into the pEF expression vector, which contains the elongation factor promoter upstream of the cloning site followed by a mammalian polyadenylation signal. This vector also contains the NEOr gene that allows for selection of cells retaining this plasmid. Briefly, cells were transfected with 1 μg of each vector using polyliposomes following the manufacturer's protocol (Life Technologies). Cells were then selected in 0.5 mg/ml of G418 for 10 days and G418 resistant cells were pooled together to analyze for gene expression. The pEF construct contains an intron that separates the exon 1 of the EF gene from exon 2, which is juxtaposed to the 5' end of the polylinker cloning site. This allows for a rapid reverse transcriptase polymerase chain reaction (RT-PCR) screen for cells expressing the spliced products. Cells were isolated and their RNA extracted using the trizol method as previously described (Nicolaides N. C., Kinzler, K. W., and Vogelstein, 8. (1995) Analysis of the 5' region of PMS2 reveals heterogeneous transcripts and a novel overlapping gene. *Genomics* 29:329-334).

Heavy chain RNA was reverse transcribed using a forward primer (5'-GATCGGATCCACCATGGGATG-GAGCTGTATCATCC-3' (SEQ ID NO:21)) and reverse primer (5'-CTGATCTAGATCATTTCCCGGGAGACA-GGGAGAGGCTCTTCTGCGTGTA-3' (SEQ ID NO:22)). Light chain RNA was reverse transcribed using a forward primer of SEQ ID NO:21 and a reverse primer (5'-CT-GATCTAGATTAACACTCTCCCCTGTTGAAGCTCTT-3' (SEQ ID NO:23)). PCR reactions were carried out with high fidelity HERCULASE DNA polymerase (STRATAGENE, La Jolla, Calif.). PCR products were digested with BamHI and XbaI and cloned into the same restriction sites of the eukaryotic expression vectors pEF4 (light chain) and pEF6 (heavy chain). Vector pEF4 (INVITROGEN) is a 5.8 kb vector carrying the zeocin resistance gene for selection of stable transfectants in eukaryotic cells. The cDNA insert is cloned downstream of hEF-intron 1, and its transcription is controlled by the human EF1alpha promoter. Downstream of the cDNA insert is the BGH polyadenylation signal allowing for efficient polyadenylation of the transcript. Vector pEF6 (INVITROGEN) is similar to pEF4 but carries the blasticidin resistance gene instead of the zeocin resistance gene. The sequence of both strands of the cDNA inserts was verified.

The resulting cDNAs coding for the full-length humanized anti-FR-α antibody heavy and light chains were transfected into CHO-K1 (ATCC CCL-61) cells. CHO-K1 cells were transfected with 0.5 micrograms of each plasmid using FUGENE transfection reagent (Roche) according to the manufacturer's instructions. Cells were maintained in RPMI1640/10% FBS/2 mM L-glutamine. Stable cell lines were selected with Zeocin (200 micrograms/milliliter) and Blasticidin (5 micrograms/ milliliter). Expression of antibody was verified by anti-human IgG ELISA. Stably transfected pools of cells were single cell cloned by limited dilution and high expressor cell lines were selected. High titers were verified in secondary and tertiary screens. The cell line was adapted to serum-free medium (CHO-S-SFMII followed by EX-CELL 302). Antibody production was verified by ELISA. The cell line also was adapted to protein-free CHO media (CD94111; Irvine Scientific) plus 8 mM L-glutamine with a soy hydrolysate pulse at day 2. Cells were stored for use in liquid nitrogen. The cells were stable for at least 13 passages in the absence of selection media as determined by FACS analysis. Cell secretion was stable for at least 20 passages as determined by ELISA. Large scale antibody production is possible. For example, antibody was produced in a bioreactor on a scale of 15 L, 70 L, and 340 L.

Example 2

Screening Strategy to Identify Antibody-Producing Clones and Characterization of Anti-FR-α Antibody An application of the methods presented within this document is the use of MMR-deficient immunoglobulin-producing cells to create a cell that is substantially free of FR-α binding competitors or a cell that produces substantially only the target immunoglobulin, for example, a FR-α antibody of the invention, including but not limited to an antibody comprising a light chain comprising an amino acid sequence of SEQ ID NO:2 or 3 and a heavy chain comprising an amino acid sequence of SEQ ID NO:5 or 6. FIG. 4 outlines the screening procedure to identify clones that produce high affinity MAbs. The assay employs the use of a plate Enzyme Linked Immunosorbant Assay (ELISA) to screen for clones that produce high-affinity MAbs. 96-well plates containing single immunoglobulin-producing cells are grown in growth medium plus 0.5 mg/ml G418 to ensure clones retain the expression vector. Plates are screened using an hIgG plate ELISA, whereby a 96 well plate is coated with FR-α. Alternatively, the plate is coated with a specific antibody against the anti-FR-α antibody. As another alternative in cases in which the immunoglobulin-producing cell is non-human, the plate may be coated with anti-human IgG1 antibody. Plates are washed 3 times in calcium and magnesium free phosphate buffered saline solution (PBS−/−) and blocked in 100 μls of PBS−/− with 5% dry milk for 1 hour at room temperature. Wells are rinsed and incubated with 100 μls of a PBS solution containing a 1:5 dilution of conditioned medium from each cell clone for 2 hours. Plates are then washed 3 times with PBS$^{-/-}$ and incubated for 1 hour at room temperature with 50 μls of a PBS$^{-/-}$ solution containing 1:3000 dilution of a sheep anti-mouse horse radish peroxidase (HRP) conjugated secondary antibody such as anti-human IgG antibody. Plates are then washed 3 times with PBS$^{-/-}$ and incubated with 50 μls of TMB-HRP substrate (BioRad) for 15 minutes at room temperature to detect amount of antibody produced by each clone. Reactions are stopped by adding 50 μls of 500 mM sodium bicarbonate and analyzed by OD at 415 nm using a BioRad plate reader. Clones exhibiting an enhanced signal over background cells (control cells with vector alone; control cells not containing the dominant negative mismatch repair allele) are then isolated and expanded into 10 ml cultures for additional characterization and confirmation of ELISA data in triplicate experiments. ELISAs are also performed on conditioned (CM) from the same clones to measure total Ig production within the conditioned medium of each well. Clones that produce an increased ELISA signal and have increased antibody levels are then further analyzed for variants that are substantially free of FR-α binding competitors. Clones that produce higher OD values as determined by ELISA are further analyzed at the genetic level to confirm the absence of FR-α binding competitors hence yielding a stronger ELISA signal. Briefly, 100,000 cells are harvested and extracted for RNA using the Triazol method as described above. RNAs are reverse transcribed using Superscript II as suggested by the manufacturer (Life Technology) and PCR amplified for the antigen binding sites contained within the variable light and heavy chains.

PCR reactions using degenerate oligonucleotides are carried out at 94° C. for 30 sec, 52° C. for 1 mm, and 72° C. for 1 min for 35 cycles. Products are analyzed on agarose gels. Products of the expected molecular weights are purified from the gels by Gene Clean (Bio 101), cloned into T-tailed vectors, and sequenced to identify the sequence of the variable light and heavy chains. Once the wild type sequence has been determined, nondegenerate primers are made for RT-PCR amplification of positive clones. Both the light and heavy chains are amplified, gel purified and sequenced using the corresponding sense and antisense primers. The sequencing of RT-PCR products gives representative sequence data of the endogenous immunoglobulin gene and not due to PCR-induced mutations. Sequences from clones are then compared to the wild type sequence.

The methods of the invention yielded an anti-FR-α antibody comprising a heavy chain comprising an amino acid sequence of SEQ ID NO:5 and a light chain comprising an amino acid sequence of SEQ ID NO:2. The molar extinction coefficient (ε) of the antibody was determined to be 43,320 by measurement of the asorbance at 280 nm of 7.41 mg.ml solution of antibody in 20 mM potassium phosphate, 150 mM NaCl at pH 7.2.

A single major band of Mr~135 kD was observed upon separation of the antibody in SDS-PAGE under nonreducing conditions. Two bands of Mr~55 kD and Mr~25 kD were observed upon reduction. Purity was ascertained by densitometric analysis of colloidal Coomassie blue-stained gels and found to be greater than about 99.5% under reducing conditions and greater than about 99% under nonreducing conditions.

Western blot analysis demonstrated that, when used to probe polypeptides separated on a nonreducing gel, the antibody was able to detect a single polypeptide of Mr~35 kD in lysates prepared from a cell line known to express FR-α but not in lysates of a cell line that does not express the antigen (1205 Lu). The antibody also was able to detect soluble FR-α secreted from KB cells, even after treatment of the antigen with PNGase F to remove N-linked oligosaccharides.

Kinetic and steady-state binding constants between the antibody of the invention and purified FR-α were determined by surface plasmon resonance spectroscopy. On-rate ($k_a$) was determined to be $(2.25\pm0.02)$ $M^{-1}s^{-1}$, and off-rate ($k_d$) was determined to be $(5.02\pm0.08)$ $s^{-1}$. A steady state dissociation constant ($K_D$) of 2.23 nM was calculated.

Example 3

Binding of Antibody to Multimeric FR-α

Binding of a monoclonal antibody to the tetrameric form of FR-α was shown by Western blot. Briefly, SK-Ov-3 and IGROV tumor cells were grown in nude mice and excised. Tumor tissues were lysed in RIPA buffer with 15-20 strokes in a 2 ml Dounce tissue homogenizer. Insoluble material was removed by centrifugation and the total protein of the supernate was determined using a BioRad protein Assay. In different experiments, either 5 ug or 20 ug of protein was run on a 4-12% Bis-Tris gel (MES) under non-reducing conditions. The electrophoresed protein was transferred to a PVDF membrane. The membrane was blocked in Blotto (5% milk, 0.05% TBS-T). A 1:100 dilution of culture supernate from LK26 hybridoma cells and total concentration of 0.1% NaN$_3$ was added directly to the Blotto blocking solution as the primary antibody, and the membrane was incubated overnight. The membrane was washed in 0.05% TBS-T and the secondary antibody (horseradish peroxidase labeled goat α-mouse IgG (heavy and light chains)) in Blotto blocking solution was added. The membrane was developed using Super Signal West Pico ECL reagent. The results are shown in FIG. 1 (lane 1, SK-Ov-3; lane 2, IGROV). The results indicate that certain tumors that over-express FR-α favor the production of multimeric FR-α over monomeric FR-α. This finding can be exploited by monoclonal antibodies that specifically recognize the tetrameric form of FR-α for the destruction of tumor tissue, while leaving normal tissue (which generally expresses the monomeric form of FR-α) unscathed.

Example 4

Expression of FR-α in *Escherichia coli*

Figure 2:
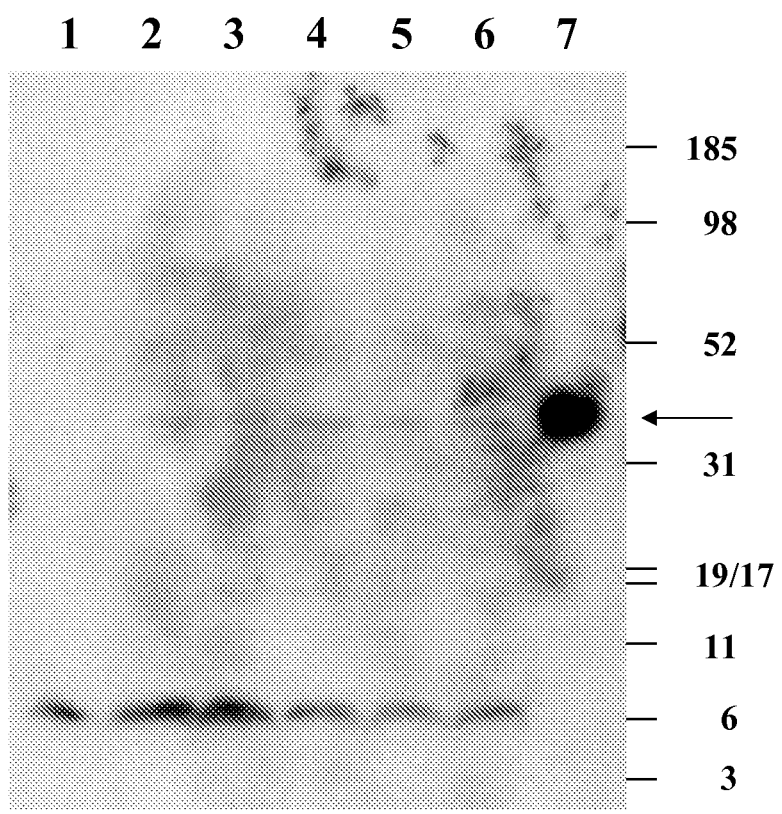
FIG. 2 shows a western blot of *Escherichia coli*-expressed FR-α.

Expression of FR-α was also assessed in *Escherichia coli*. Briefly, a plasmid containing the coding sequence for FR-α with a histidine tag (pBAD-His-hFR-α) was transfected into *E. coli* cells. A culture of *E. coli* containing plasmid pBAD-His-h FR-α was grown to OD$_{600}$=1.0. Thereafter, arabinose was added to a final concentration of 0.2%, and samples were taken at the time points indicated in FIG. 2. *E. coli* lysates were prepared by adding 25 ml of 4× LDS sample buffer to 65 ml culture. JAR cells were propagated in RPMI1640 medium containing 10% FBS, L-glutamine, sodium pyruvate, non-essential amino acids and penicillin/ streptomycin. The medium was removed from the cells and RIPA buffer was added directly to the culture plates to lyse the cells for JAR cell extract controls. Samples were separated on a 4-12% NuPAGE gel (MES) and transferred to a PVDF membrane. After overnight blocking in TBST+5% milk, the membrane was probed with 1:1000 dilution of mAb LK26 for 1 hr followed by a 1:10000 dilution of secondary antibody (goat α-mouse Ig conjugated to horseradish peroxidase) for 1 hr. Detection of the antibody was performed with Pierce Super Signal femto after an exposure of 5 minutes. The results are shown in FIG. 2 (lane 1, *E. coli*+pBAD-His-hFRa, induced 180 min.; lane 2, *E. coli*+pBAD-His-hFRa, induced 90 min.; lane 3, *E. coli*+pBAD-His-hFRa, induced 60 min.; lane 4, *E. coli*+pBAD-His-hFRa, induced 30 min.; lane 5, *E. coli*+pBAD-His-hFRa, induced 15 min.; lane 6, *E. coli*+pBAD-His-hFRa, uninduced; lane 7, JAR cell extract).

Example 5

Multimeric Form of FR-α not an Artifact of Sample Preparation

Figure 3:
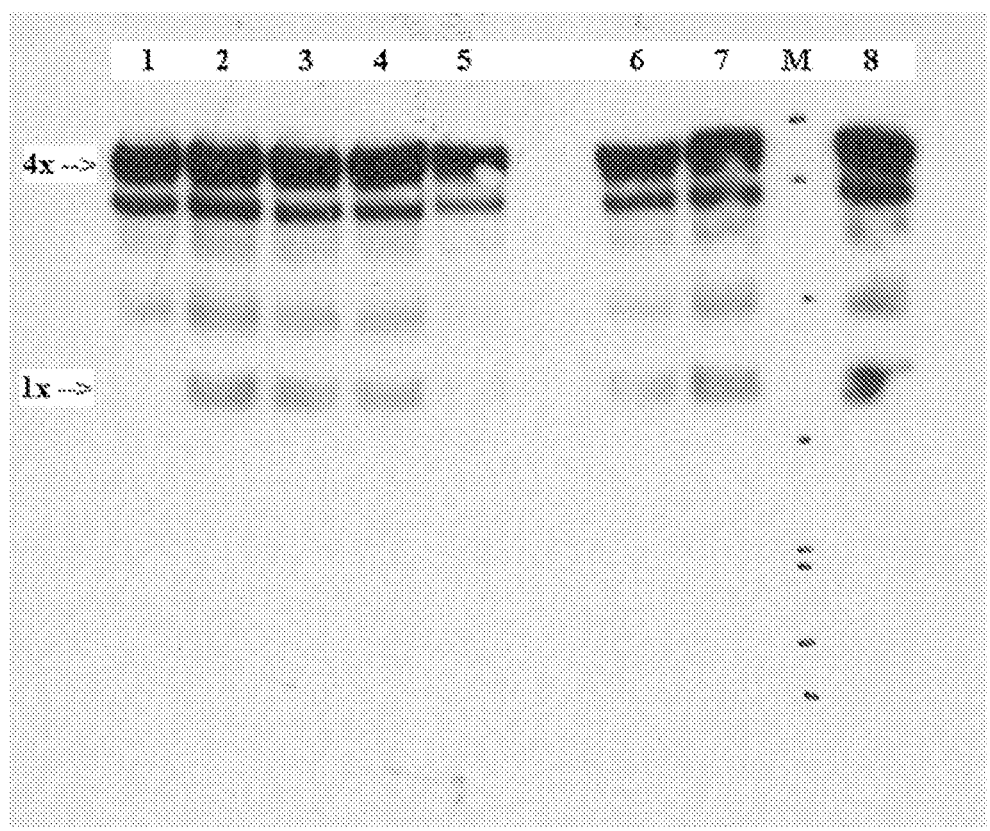
FIG. 3 shows a western blot of FR-α solubilized in the presence or absence of Triton X-100.

To demonstrate that the multimeric FR-α was not an artifact of aggregation in Triton X-100 micelles as described by Holm et al. (1997) *Biosci. Reports* 17(4):415-427, extracts of tumors were diluted in either 1× RIPA (1% Triton X-100, 0.1% SDS, 180 mM NaCl, 20 mM potassium phosphate, pH=7.2) or 1× PBS (150 mM NaCl, 20 mM potassium phosphate, pH=7.2). For all samples, 1 ug/ul of stock IGROV extract was used. After dilution, 4× LDS sample buffer was added to each sample to a final concentration of 1×. The samples were loaded on a 4-12% Bis-Tris gel in MES running buffer. Following electrophoresis, the protein was transferred to a PVDF membrane. The membrane containing the transferred protein was blocked for 48 hrs at room temperature in Blotto (5% skim milk, 1× TBS, 0.05% Tween-20). The membrane was developed by incubating the membrane with a primary antibody (1 ug/ml LK26 antibody) followed by washing, then incubation with a secondary antibody (HRP-conjugated goat α-mouse IgG in Blotto). Following another washing step, the membrane was developed using a Super Signal West Pico ECL reagent and exposed for 1 minute. The results are shown in FIG. 3 (lane 1, 1:100 dilution in PBS; lane 2, 1:50 dilution in PBS; lane 3, 1:25 dilution in PBS; lane 4, 1:10 dilution in PBS; lane 5, 1:100 dilution in RIPA; lane 6, 1:25 dilution in RIPA; lane 7, 1:10 dilution in RIPA; M, molecular weight markers, lane 8, 1:1 dilution in RIPA). Arrows indicate monomer (1×) and tetramer (4×). No treatment disrupted the tetrameric form of FR-α. The results indicate that certain tumors that overexpress FR-α express a multimeric form of FR-α that has only been shown previously as artifacts of gel filtration sample preparation.

Example 6

Screening Cells for ADCC Activity

The mAb-producing cells expressing the hPMS-134 will be subcloned by liming dilution and seeded in a flat-bottom 96-well plate. Seeding density will be determined empirically in order to obtain 40 single-cell colonies per plate to approximate monoclonality.

The clones will be allowed to grow for a number of days, which will be empirically determined, after which a sufficient amount of antibody, capable of mediating ADCC activity, is produced. At the end of the incubation period, 50 ul of conditioned medium from each clone/well will be used to assess concentration of antibodies by ELISA, while another 50 ul of conditioned medium from the same well/clone will be utilized in the ADCC assay. Briefly, for example, an anti-ovarian cancer mAb is used in conjunction with the target cells, SKOV3 (passage 1 to 20, obtained from ATCC), which are seeded the day before the assay in a flat-bottom 96-well microplate at a density of 30,000 cell/well in complete growth medium (RPMI-1640 containing 10% FBS, 2 mM L-glutamine). The following day, the complete medium is replaced with 100 ul of CHO-CD serum-free medium and 50 ul of antibody-containing conditioned medium will be added to target cells and incubated for 20 minutes at 37° C. Subsequently, 100 ul of serum-free medium containing $2\times10^5$ effector cells are added to each well and cells are incubated for 5-6 hours at 37° C., 5% $CO_2$. Plates are then briefly centrifuged and 100 ul of supernatant is collected from each well and transferred into ELISA plates (Nunc). One hundred ul of LDH substrate (Roche) is added to supernatants and incubated for 10 minutes at ambient temperature. LDH activity will be proportional to the extent of the LDH enzyme released from lysed target cells. Optical density at 490 um ($OD_{490}$) is obtained spectrophotometrically and percent of cytotoxicity is determined with the formula: (sample $OD_{490}$–spontaneous $OD_{490}$)/(max $OD_{490}$–spontaneous $OD_{490}$)×100%, where 'spontaneous'=target cells' lysis in absence of effector cells or antibody, and 'max'=target cells' lysis in the presence of 2% Triton. Cytotoxicity elicited by 100 ng/ml of a reference antibody (protein A purified, parental antibody) will be used as positive control. Non-specific cytotoxicity will be monitored using 100 mg/ml of normal human IgG1. The ratio obtained by dividing the % cytotoxicity by the concentration of the antibody for each well/clone (i.e., ratio=50(%)/100 (ng/ml)=0.5) will be set as the criterion for selecting lead clones. Lead clones will be expanded to 50 ml cultures and antibody will be purified from their conditioned media by protein-A affinity column as described. ADCC activities of the antibodies produced by the lead clones will be compared to the parental antibody using concentrations ranging from 10-1000 ng/ml.

In an alternative ADCC assay, the ability of antibody to produce ADCC was evaluated using SKOV-3, IGROV-1, and 1205 Lu (negative control) as target cells, and PBMCs from normal blood donors. Antibody was tested at a concentration of 10 micrograms/milliliter. Donor PBMCs used as effector cells were thawed and kept overnight in medium (IMDM supplemented with 10% FCS). The cells were resuspended in medium at a concentration of $10^7$ cells/milliliter. The tumor cells used as target cells were detached from the culture flask and $10^6$ cells in 100 microliters FCS were labeled with 100 uCi (3.7 MBq) $^{51}Cr$ (Amersham, Buckinghamshire, UK) for 2 hours at 37° C. Cells were washed thrice with 5 milliliters medium and resuspended in medium at a concentration of $10^5$ cells/milliliter. Fifty microliters of the tumor cells were seeded in V bottom 96-well plates. Cells were then incubated with 50 microliters medium containing the test antibody or control antibody. After 30 minutes incubation at 37° C., 50 microliters of the PBMCs were seeded in V bottom 96 well plates at various target-effector cell ratios (1:0, 1:25, 1:50, and 1:100) and the plates were further incubated for 18hours at 37° C. The release of $^{51}$Cr in the supernatant was determined in a LKB gamma-counter. Each measurement was carried out in triplicate. The percentage of release was defined as:

% release=[(release−spontaneous release)/(maximal release−spontaneous release)]×100.

The percentage of specific release was defined as:

% specific $^{51}$Cr release=% total $^{51}$Cr release with antibody−% total $^{51}$Cr release without antibody.

Results:

TABLE 1

SKOV-3 Percentage of $^{51}$Cr release

| T:E ratio | Patient 1 | | | Patient 2 | | |
|---|---|---|---|---|---|---|
| | Without Antibody | Control IgG | With Antibody | Without antibody | Control IgG | With Antibody |
| 1:0 | 1.3 ± 0.0 | 1.6 ± 0.0 | 2.0 ± 0.0 | −1.4 ± 0.0 | −0.7 ± 0.0 | −0.6 ± 0.0 |
| 1:25 | 5.3 ± 0.3 | 5.0 ± 0.1 | 36.1 ± 1.4 | 2.6 ± 0.0 | 3.3 ± 0.0 | 31.2 ± 1.0 |
| 1:50 | 6.8 ± 0.1 | 5.9 ± 0.1 | 46.2 ± 1.0 | 4.5 ± 0.1 | 6.7 ± 0.1 | 43.5 ± 1.3 |
| 1:100 | 8.0 ± 0.2 | 8.3 ± 0.3 | 61.7 ± 0.2 | 7.6 ± 0.5 | 6.3 ± 0.8 | 56.0 ± 1.0 |

TABLE 2

SKOV-3 Percentage of specific $^{51}$Cr release

| T:E ratio | Patient 1 | | Patient 2 | |
|---|---|---|---|---|
| | Control IgG | Antibody | Control IgG | Antibody |
| 1:0 | 0.3 ± 0.0 | 0.7 ± 0.0 | 0.7 ± 0.0 | 0.8 ± 0.0 |
| 1:25 | −0.3 ± 0.4 | 30.8 ± 1.7 | 0.7 ± 0.1 | 28.6 ± 1.0 |
| 1:50 | −0.9 ± 0.2 | 39.4 ± 1.1 | 2.2 ± 0.2 | 39.0 ± 1.4 |
| 1:100 | 0.3 ± 0.3 | 53.7 ± 0.3 | −1.3 ± 1.2 | 48.4 ± 1.5 |

TABLE 3

IGROV-1 Percentage of $^{51}$Cr release

| T:E ratio | Patient 1 | | | Patient 2 | | |
|---|---|---|---|---|---|---|
| | Without Antibody | Control IgG | With Antibody | Without antibody | Control IgG | With Antibody |
| 1:0 | −3.0 ± 0.1 | −4.9 ± 0.2 | −4.1 ± 0.1 | −13.3 ± 0.3 | −12.0 ± 0.5 | −10.9 ± 0.2 |
| 1:25 | 14.9 ± 3.3 | 20.0 ± 1.0 | 70.2 ± 1.3 | 15.6 ± 2.9 | 13.4 ± 1.6 | 46.0 ± 1.2 |
| 1:50 | 15.2 ± 2.2 | 29.4 ± 2.3 | 66.8 ± 7.1 | 23.0 ± 0.6 | 26.7 ± 0.5 | 64.7 ± 1.3 |
| 1:100 | 24.0 ± 4.1 | 33.8 ± 2.7 | 65.2 ± 1.2 | 36.8 ± 2.4 | 41.1 ± 1.6 | 67.8 ± 10.5 |

TABLE 4

IGROV-1 Percentage of specific $^{51}$Cr release

| T:E ratio | Patient 1 | | Patient 2 | |
|---|---|---|---|---|
| | Control IgG | Antibody | Control IgG | Antibody |
| 1:0 | −1.9 ± 0.3 | −1.1 ± 0.2 | 1.3 ± 0.7 | 2.4 ± 0.5 |
| 1:25 | 5.1 ± 4.3 | 55.3 ± 4.4 | −2.2 ± 4.4 | 30.4 ± 4.1 |
| 1:50 | 14.2 ± 4.5 | 51.6 ± 9.3 | 3.7 ± 1.1 | 41.7 ± 1.9 |
| 1:100 | 9.8 ± 6.8 | 41.2 ± 5.3 | 4.3 ± 4.0 | 31.0 ± 12.9 |

ADCC assays using human ovarian cancer cells as target and peripheral blood mononuclear cells (PBMCs) as effector cells showed that anti-FR-α antibody mediated killing of tumor cell line SKOV-3. IGROV-1 aggregated very quickly and tended to form cell clumps. The cell line was sensitive to killing by PBMCs alone. Control antibody also mediated some killing. Antibody mediated killing of IGROV-1.

Example 7

Immunohistochemistry Assay Using Anti-FR-α Antibody

Tissue preparation. Human tissue samples were obtained at autopsy or biopsy. Tissues tested included adrenal, blood cells (granulocytes, lymphocytes, monocytes, platelets), blood vessels (endothelium), bone marrow, brain (cerebrum (cortex), cerebellum), breast (mammary gland), eye, gastrointestinal tract (colon (large intestine), esophagus, small intestine, stomach), heart, kidney (glomerulus, tubule), liver, lung, lymph node, ovary and fallopian tube (oviduct), pancreas, parathyroid, peripheral nerve, pituitary, placenta, prostate, salivary gland, skin, spinal cord, spleen, striated (skeletal) muscle, testis, thymus, thyroid, tonsil, ureter, urinary bladder, uterus (body (endometrium), cervix), ovarian carcinoma (carcinoma cells), ovarian carcinoma (stromal fibroblasts). Fresh unfixed tissue samples were placed in molds and frozen on dry ice in TISSUE-TEK O.C.T. embedding medium. Tissue samples were sectioned and fixed for 10 minutes in room temperature acetone. Tissues were stored below −70° C. until staining. Just prior to staining, the slides were fixed in 10% neutral buffered formalin.

Antibody preparation. Antibody was applied to tissue samples at two concentrations: 1 microgram/milliliter and 25 micrograms/milliliter.

Assays lacking primary antibody were used as an assay control. Mouse anti-fluorescein was used as secondary antibody. Goat anti-mouse IgG (GAMIgG)-peroxidase polymer was used as tertiary antibody. 3,3'-diaminobenzidinen (DAB) was used as substrate chromogen.

Immunohistochemistry analysis. An indirect immunoperoxidase procedure was performed. Acetone/formalin-fixed cryosections were rinsed twice in phosphate buffered saline (PBS [0.3M NaCl, pH 7.2]). Endogenous peroxidase was blocked by incubating the slides with peroxidase solution of Dako EnVision Kit for 5 minutes followed by two rinses in phosphate buffered saline. Slides were then treated with a protein block (phosphate buffered saline, 0.5% casein, 5% human gamma globulins, and 1 mg/ml heat aggregated HuIgG (prepared by heating a 5 mg/ml solution to 63° C. for 20 minutes and then cooling to room temperature)) designed to reduce nonspecific binding for 20 minutes. Following the protein block, primary antibody (anti-FR-α antibody, negative control antibody (HuIgG1 or MsIgG1), or none) was applied at room temperature for one hour. Unconjugated secondary antibody (mouse anti-fluorescein) was applied for 30 minutes. Slides were twice rinsed with PBS, treated with peroxidase-labeled goat anti-mouse IgG polymer (Dako EnVision kit) for 30 minutes, rinsed twice with PBS, and treated with substrate-chromogen (DAB; Dako EnVision) for 8 minutes. Slides were rinsed in water, counterstained with hematoxylin, dehydrated, and coverslipped.

Results. The anti-FR-α antibody specifically and intensely stained human ovarian carcinoma cells (HT162) at both antibody concentrations as a positive control. Anti-FR-α antibody did not react with ovarian carcinoma (stromal fibroblasts) (negative control). Negative control antibodies HuIgG1 and MsIgG1 did not specifically react with the positive or negative control cells. No reactivity was observed with any tissues when primary antibody was omitted from the staining reaction. See Table 1.

Tissue cross-reactivity of anti-FR-α antibody.

TABLE 5

Cancer-specific expression of target antigen

| Tumor tissue origin | Expression by IHC | % positive samples of total tested | Total number of samples tested (n) |
|---|---|---|---|
| Normal adult | – | 0 | 62 |
| Ovarian carcinoma cells | +++++ | 91 | 136 |
| Breast | ++++ | 21 | 53 |
| Renal | ++++ | 50 | 18 |
| Colorectal | +++ | 22 | 27 |
| Lung | +++ | 33 | 18 |
| Endometrial | +++ | 91 | 11 |
| Brain | +++ | 80 | 5 |
| Melanoma | – | 0 | 8 |
| lymphoma | – | 0 | 32 |

+/– indicates level of expression as detected by immunohistochemistry

The antibodies of the invention do not react with stromal fibroblasts of ovarian carcinoma tissue (data not shown). Similar results for immunohistochemical and tissue distribution analyses were obtained with the antibodies of the invention in cynomolgus monkey and human (data not shown). Positive binding is seen in the cynomolgus monkey kidney cortex (proximal tubules and collecting ducts) and epithelium, tubular (membrane, cytoplasm/cytoplasmic granules), and uctules (membrane, cytoplasm) (data not shown).

In normal human tissues, anti-FR-α antibody specific staining was observed in tubular epithelium (kidney), bronchiolar epithelium (lung); pneumocytes (lung); epithelium of fallopian tube; and duct and ductile epithelium of the pancreas at both antibody concentrations.

In neoplastic human tissues, anti-FR-α antibody specific staining was observed in ovarian carcinoma tissue, endometrial carcinoma tissue, and renal carcinoma tissue. Staining of ovarian and renal carcinoma cells occurred at the membrane and cytoplasm (data not shown).

These results are consistent with distribution of FR-α reported in literature (Weitman, et al., *Cancer Res.*, 61:3869-3876 (2001)).

In summary, FR-α is a glycoprotein whose expression is highly restricted in normal tissues and highly expressed in a large portion of ovarian tumors. Anti-FR-α antibodies of the invention are capable of inducing ADCC, thus making the antibodies of the invention excellent drug candidates for the treatment of a variety of cancers, including ovarian cancer.

Example 8

Receptor Binding Activity

One of the major modes of action of unconjugated therapeutic monoclonal antibodies directed against tumor antigens is through recruitment of immune effector populations to the tumor cells (Clynes R, Takechi Y, Moroi Y, Houghton A, Ravetch J V. *Proc. Natl. Acad. Sci. U.S.A.* 1998 Jan. 20; 95(2):652-6; Clynes R A, Towers T L, Presta L G, Ravetch J V. *Nat. Med.* 2000 April; 6(4):443-6). It is presumed that the efficiency with which a given antibody can recruit immune effector cells to a tumor cell is influenced by the affinity of the antibody for its cognate antigen on the tumor cell surface, such that a high affinity antibody will display more efficient recruitment of immune effectors to the tumor cell than a lower affinity counterpart recognizing the same antigen. Limited reports have attempted to demonstrate this relation in vitro (Alsmadi, 0. and Tilley, S A. *J. Virol.* 1998 January; 72(1):286-293; McCall, A M., Shahied, L., Amoroso, A R., Horak, E M., Simmons, R H., Nielson, U., Adams, G P., Schier, R., Marks, J D., Weiner, L M. *J. Immunol.* 2001 May 15; 166(10):6112-7, as well as in vivo (Velders, M P, van Rhijn, C M., Oskam, G J., Warnaar, S O. and Litvinov, S V. *J. Cancer* 1998; 78(4):476-483). In order to determine if such a correlation exists, in vitro ADCC activity of anti-FR-α antibodies and the affinity of these antibodies may be compared for their relevant antigen by surface plasmon resonance spectroscopy.

Surface plasmon resonance spectroscopy relies on the short range (~150 nm) interaction of the electrical field (evanescent wave) generated by photons under conditions of total internal reflection (TIR) with electrons (surface plasmons) in a conductive film at the boundary between two media of differing refractive indices, whereby one of the media is a thin gold layer (conductive film) coated with an alkane linker coupled to CM-dextran. The CM-dextran surface, which forms an extended hydrogel in solution, projecting roughly 100-150 nm into the flowcell, may be derivatized further with a ligand of choice by covalent immobilization to the carboxyl groups present on the CM-dextran layer. The angle necessary to allow the evanescent wave to interact with the gold layer will depend on the angle necessary to observe TIR, which in turn depends on the thickness or mass at the surface of the chip. The instrument thus allows for observation of the change in mass at the surface of the chip over time, as would be observed when an analyte which interacts with the immobilized ligand is injected into the flowcell. If injection of analyte is followed by injection of buffer, one can follow both the association (during injection of the analyte) and dissociation phases (during buffer injection) of the binding. Kinetic on-rates ($k_a$) and off-rates ($k_d$), as well as steady-state equilibrium constants ($K_a$ and $K_d$) can thus be extrapolated.

The soluble, secreted form of the antigen will be purified from the serum-free culture supernatant of target cells by chromatography through Phenyl Sepharose (high sub), followed by ion exchange on S Sepharose Fast Flow. Briefly, culture supernatant containing secreted antigen will be loaded onto the Phenyl Sepharose (high sub) column in the absence of additional salts. Unbound proteins will be removed by extensive washing in HIC A (20 mM K phosphate pH 7.2), followed by elution of bound antigen using a linear gradient of 0-20 mM CHAPS in HIC buffer. Peak anti-FR-α antibody-containing fractions will be pooled, acidified (pH 5.5) with 1 M citrate, then applied to a S Sepharose cation exchange column. After washing with IEX buffer (20 mM K phosphate, pH 5.5), bound antigen will be eluted using a linear gradient of 0-1 M NaCl in IEX buffer. Peak fractions will be pooled, concentrated using a Centricon centrifugal concentration device (Millipore), and dialyzed against PBS. Based on the purity of the antigen preparation, an additional affinity chromatography step on covalently coupled folate Sepharose resin may be necessary (Sadasivan, E., da Costa, M., Rothenberg, S P. and Brink, L. *Biochim. Biophys. Acta* 1987; (925):36-47).

The antibody to be assayed will be purified in one step by affinity chromatography on recombinant protein A Sepharose resin (RPA-Sepharose, Amersham Biosciences) Immunoglobulin (Ig) containing tissue culture supernatants will be loaded onto RPA-Sepharose columns by gravity, at an Ig/ml resin value of 10 mg/mL of resin. Unbound proteins will be removed by extensive washing with PBS, followed by elution using 0.1 M glycine-HCl pH 2.6. Fractions will be neutralized with 1 M Tris. Peak fractions will be pooled, and dialyzed against 1000 volumes of PBS. Ig concentration will be determined by BCA protein assay (Pierce Chemical Co.) and Ig-specific ELISA.

Purified antigen will be diluted into coupling buffer (10 mM NaOAc pH 5.0), and immobilized onto the flowcell of a CM5 sensor chip (Biacore) by amine coupling, using a mixture of N-hydroxysuccinimide (NHS) and 1-ethyl-3-[dimethylaminopropyl]carbodiimide hydrochloride (EDC) to activate carboxyl groups in the CM-Dextran hydrogel attached to the surface of the CM5 sensor chip. Activated, underivatized carboxyl groups will be quenched with 1 M ethanolamine A reference flowcell, consisting of the quenched CMDextran surface, activated in the absence of antigen, will be used to normalize all measurements. Crude, mAb-containing culture supernatants, or purified mAb preparations will be injected at flow rates of 30 ul/min for kinetic assays, and 5 ul/mm for steady-state affinity ranking experiments, using HBS-EP (20 mM HEPES-OH, 150 mM NaCl, 3 mM EDTA, 0.005% Surfactant P-20, pH 7.4) as running buffer. Purified mAb preparations will be dialyzed against HBS-EP, using 10K MWCO Slide-A-Lyzer dialysis cassettes (Pierce) prior to their use in Biacore analysis. For samples containing tissue culture supernatant, BSA and soluble CM-Dextran will be added to final concentrations of 1% and 1 mg/ml, respectively. Regeneration of the surface will be accomplished by 30 second injection of 50 mM NaOH, at a flow rate of 100 ul/min. Data analysis will be performed using Bia Evaluation software (Biacore). Kinetic data will be fitted to a simple 1:1 (Langmuir) binding model. For ranking experiments, rank will be determined by $K_D$ values obtained from plots of Req versus C at different concentrations of sample.

Example 9

Evaluation of Antibody in Human Tumor Xenograft Model

The SKOV-3 tumor cell line has been shown to express FR-α both on cells in culture and in tumor xenografts.
Antibody may be evaluated in vivo using the tumor xenograft model of SKOV-3 cells in mice. Paclitaxel may be used as a positive control. Negative controls may be isotype matched, nonspecific murine IgG and vehicle control. Inhibition of tumor growth by the antibody relative to the negative controls is an indication that the antibody is useful in the treatment of ovarian cancer. The antibody preferably demonstrates tumor growth inhibition of at least about 58%.

Example 10

Growth Inhibition Experiments

The sulforhodamine B (SRB) test (Shekan et al. (1990) *J. Nat. Cancer Inst.* 82:107-112, as modified by Keepers et al. (1991) *Eur. J. Cancer* 27:897-900) may be used to test the effect of antibody treatment on the susceptibility of cancer cells to treatment with antifolate compounds. Briefly (as described in Backus et al. (2000) *Int. J. Cancer* 87:771-778, cells are seeded in 100 ul medium (suitable for use with each particular cell line chosen for testing) in 96-well flat-bottom plates (in triplicate). Seeding density may vary according to the cell type used, but may be, for example, 8,000 cells/well for colon cancer cells,15,000 cells/well for squamous cell carcinoma cells of the head and neck. The cells are cultured in the presence of 1-100 ug/ml anti-folate receptor antibody. After 24 hours, 100 ul of drug containing medium is added and cells are cultured for an additional 72 hours. The concentration of drugs such as 5-fluoro-2'-deoxy-uridine-5'-monophosphate (FdUMP), leucovorin, ZD1649, MTA, GW1843U89, ZD9331, AG337, and PT523 ranges from $1 \times 10^{-5}$ to $1 \times 10^{-11}$ M. 5-FU is tested in a range of $1 \times 10^{-4}$ to $1 \times 10^{-10}$ M with or without 10 uM leucovorin. After 72 hrs of exposure to drug(s), the cells are fixed with trichloroacetic acid (TCA) and stained with SRB protein dye. Results are expressed as % of control growth based on the difference in optical density ($OD_{540}$) at the beginning and end of the drug exposure period according to the formula published by Peters et al. ((1993) *Int. J. Cancer* 54:450-455):

$$[(OD_{treated}/OD_{start\ of\ exposure})-1]/[(OD_{control}/OD_{start\ of\ exposure})-1] \times 100\%.$$

$IC_{50}$ values are calculated based on absorption values defined as drug concentration corresponding to a reduction of cellular growth by 50% when compared with values of untreated control cells.

Example 11

Combination of Antifolate Antibodies and Antifolate Compounds

For combination therapy, efficacy may be demonstrated in vitro using the assay described above for ovarian cancer cell lines and the monoclonal antibodies of the invention. One of skill in the art may extrapolate dosages from the in vitro efficacy assays to determine a range of efficacy in patients. Furthermore, dosages of antibodies accepted in the art for administration can be matched with dosages accepted for various folate inhibitors and adjusted to achieve maximum benefit with the minimum dosage. One of skill in the art is able to adjust these dosages to achieve the desired effect with routine experimentation particularly with the guidance on dosage for antibodies provided above and the assay described for determining an effect in vitro.

What is claimed:

1. A composition of comprising an antibody that specifically binds folate receptor-alpha, wherein said antibody comprises a heavy chain expressed from a cDNA comprising a nucleotide sequence encoding an amino acid sequence comprising SEQ ID NO: 4 and a light chain expressed from a cDNA comprising a nucleotide sequence encoding an amino acid sequence comprising SEQ ID NO: 1, and wherein said composition is free of a polypeptide consisting of amino acids 20 to 111 of SEQ ID NO: 24.

2. The composition of claim 1 wherein said heavy chain is expressed from a cDNA comprising a nucleotide sequence encoding an amino acid sequence comprising SEQ ID NO: 5.

3. The composition of claim 1 wherein said light chain is expressed from a cDNA comprising a nucleotide sequence encoding an amino acid sequence comprising SEQ ID NO: 2.

4. The composition of claim 1 wherein said heavy chain is expressed from a cDNA comprising a nucleotide sequence encoding an amino acid sequence comprising SEQ ID NO: 5 and said light chain is expressed from a cDNA comprising a nucleotide sequence encoding an amino acid sequence comprising SEQ ID NO: 2.

5. The composition of claim 1 wherein said heavy chain is expressed from a cDNA comprising the nucleotide sequence of SEQ ID NO: 7.

6. The composition of claim 1 wherein said light chain is expressed from a cDNA comprising the nucleotide sequence of SEQ ID NO: 8.

7. The composition of claim 1 comprising a homogeneous population of antibodies.

8. The composition of claim 1 wherein said antibody further comprises a constant region.

9. The composition of claim 1 further comprising a pharmaceutically acceptable carrier.

10. A composition comprising an antibody that specifically binds folate receptor-alpha, wherein said antibody comprises a heavy chain comprising the amino acid sequence of SEQ ID NO: 4 and a light chain comprising the amino acid sequence of SEQ ID NO: 1, and wherein said composition is free of a polypeptide consisting of amino acids 20 to 111 of SEQ ID NO: 24.

11. The composition of claim 10 wherein said heavy chain comprises the amino acid sequence of SEQ ID NO: 5.

12. The composition of claim 10 wherein said light chain comprises the amino acid sequence of SEQ ID NO: 2.

13. The composition of claim 10 wherein said heavy chain comprises the amino acid of SEQ ID NO: 5 and said light chain comprises the amino acid sequence of SEQ ID NO: 2.

14. The composition of claim 10 comprising a homogeneous population of antibodies.

15. The composition of claim 10 wherein said antibody further comprises a constant region.

16. The composition of claim 10 further comprising a pharmaceutically acceptable carrier.

* * * * *

SEQUENCE LISTING

<160> NUMBER OF SEQ ID NOS: 25

<210> SEQ ID NO 1
<211> LENGTH: 110
<212> TYPE: PRT
<213> ORGANISM: Artificial Sequence
<220> FEATURE:
<223> OTHER INFORMATION: Synthetic Construct

<400> SEQUENCE: 1

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 2
<211> LENGTH: 217
<212> TYPE: PRT
<213> ORGANISM: Artificial Sequence
<220> FEATURE:
<223> OTHER INFORMATION: Synthetic Construct

<400> SEQUENCE: 2

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 3
<211> LENGTH: 236
<212> TYPE: PRT
<213> ORGANISM: Artificial Sequence
<220> FEATURE:
<223> OTHER INFORMATION: Synthetic Construct

<400> SEQUENCE: 3

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
            20                  25                  30

Ser Val Gly Asp Arg Val Thr Ile Thr Cys Ser Val Ser Ser Ser Ile
        35                  40                  45

Ser Ser Asn Asn Leu His Trp Tyr Gln Gln Lys Pro Gly Lys Ala Pro
    50                  55                  60

Lys Pro Trp Ile Tyr Gly Thr Ser Asn Leu Ala Ser Gly Val Pro Ser
65                  70                  75                  80

Arg Phe Ser Gly Ser Gly Ser Gly Thr Asp Tyr Thr Phe Thr Ile Ser
                85                  90                  95

Ser Leu Gln Pro Glu Asp Ile Ala Thr Tyr Tyr Cys Gln Gln Trp Ser
            100                 105                 110

Ser Tyr Pro Tyr Met Tyr Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 4
<211> LENGTH: 119
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
            50                  55                  60

Lys Gly Arg Phe Ala Ile Ser Arg Asp Asn Ala Lys Asn Thr Leu Phe
 65                  70                  75                  80

Leu Gln Met Asp Ser Leu Arg Pro Glu Asp Thr Gly Val Tyr Phe Cys
                 85                  90                  95

Ala Arg His Gly Asp Asp Pro Ala Trp Phe Ala Tyr Trp Gly Gln Gly
                100                 105                 110

Thr Pro Val Thr Val Ser Ser
                115

<210> SEQ ID NO 5
<211> LENGTH: 449
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Val Val Gln Pro Gly Arg
 1               5                  10                  15

Ser Leu Arg Leu Ser Cys Ser Ala Ser Gly Phe Thr Phe Ser Gly Tyr
                 20                  25                  30

Gly Leu Ser Trp Val Arg Gln Ala Pro Gly Lys Gly Leu Glu Trp Val
             35                  40                  45

Ala Met Ile Ser Ser Gly Gly Ser Tyr Thr Tyr Tyr Ala Asp Ser Val
         50                  55                  60

Lys Gly Arg Phe Ala Ile Ser Arg Asp Asn Ala Lys Asn Thr Leu Phe
 65                  70                  75                  80

Leu Gln Met Asp Ser Leu Arg Pro Glu Asp Thr Gly Val Tyr Phe Cys
                 85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

-continued

```
Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 6
<211> LENGTH: 468
<212> TYPE: PRT
<213> ORGANISM: Artificial Sequence
<220> FEATURE:
<223> OTHER INFORMATION: Synthetic Construct

<400> SEQUENCE: 6

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Val Val Gln
            20                  25                  30

Pro Gly Arg Ser Leu Arg Leu Ser Cys Ser Ala Ser Gly Phe Thr Phe
        35                  40                  45

Ser Gly Tyr Gly Leu Ser Trp Val Arg Gln Ala Pro Gly Lys Gly Leu
    50                  55                  60

Glu Trp Val Ala Met Ile Ser Ser Gly Gly Ser Tyr Thr Tyr Tyr Ala
65                  70                  75                  80

Asp Ser Val Lys Gly Arg Phe Ala Ile Ser Arg Asp Asn Ala Lys Asn
                85                  90                  95

Thr Leu Phe Leu Gln Met Asp Ser Leu Arg Pro Glu Asp Thr Gly Val
            100                 105                 110

Tyr Phe Cys Ala Arg His Gly Asp Asp Pro Ala Trp Phe Ala Tyr Trp
        115                 120                 125

Gly Gln Gly Thr Pro Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190
```

```
Ala Val Leu Gln Ser Ser Gly Leu Tyr Ser Leu Ser Ser Val Val Thr
            195                 200                 205

Val Pro Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
    275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
    355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
    435                 440                 445

Met His Glu Ala Leu His Asn His Tyr Thr Gln Lys Ser Leu Ser Leu
        450                 455                 460

Ser Pro Gly Lys
465

<210> SEQ ID NO 7
<211> LENGTH: 1407
<212> TYPE: DNA
<213> ORGANISM: Artificial Sequence
<220> FEATURE:
<223> OTHER INFORMATION: Synthetic Construct

<400> SEQUENCE: 7
atgggatgga gctgtatcat cctcttcttg gtagcaacag ctacaggtgt ccactccgag      60
gtccaactgg tggagagcgg tggaggtgtt gtgcaacctg gccggtccct gcgcctgtcc     120
tgctccgcat ctggcttcac cttcagcggc tatgggttgt cttgggtgag acaggcacct     180
ggaaaaggtc ttgagtgggt tgcaatgatt agtagtggtg gtagttatac ctactatgca     240
gacagtgtga aggtagatt tgcaatatcg cgagacaacg ccaagaacac attgttcctg     300
caaatggaca gcctgagacc cgaagacacc ggggtctatt tttgtgcaag acatggggac     360
gatcccgcct ggttcgctta ttggggccaa gggaccccgg tcaccgtctc ctcagcctcc     420
accaagggcc catcggtctt ccccctggca ccctcctcca agagcacctc tgggggcaca     480
```

```
gcggccctgg gctgcctggt caaggactac ttccccgaac cggtgacggt gtcgtggaac       540
tcaggcgccc tgaccagcgg cgtgcacacc ttcccggctg tcctacagtc ctcaggactc       600
tactccctca gcagcgtggt gaccgtgccc tccagcagct gggcaccca gacctacatc        660 tgcaacgtga atcacaagcc cagcaacacc aaggtggaca gaaagttga cccaaatct         720 tgtgacaaaa ctcacacatg cccaccgtgc ccagcacctg aactcctggg gggaccgtca       780
gtcttcctct tccccccaaa acccaaggac accctcatga tctcccggac ccctgaggtc       840
acatgcgtgg tggtggacgt gagccacgaa gaccctgagg tcaagttcaa ctggtacgtg       900
gacggcgtgg aggtgcataa tgccaagaca aagccgcggg aggagcagta caacagcacg       960
taccgtgtgg tcagcgtcct caccgtcctg caccaggact ggctgaatgg caaggagtac      1020
aagtgcaagg tctccaacaa agccctccca gcccccatcg agaaaaccat ctccaaagcc      1080
aaagggcagc cccgagaacc acaggtgtac accctgcccc catcccggga tgagctgacc      1140
aagaaccagg tcagcctgac ctgcctggtc aaaggcttct atcccagcga catcgccgtg      1200
gagtgggaga gcaatgggca gccggagaac aactacaaga ccacgcctcc cgtgctggac      1260
tccgacggct ccttcttcct ctacagcaag ctcaccgtgg acaagagcag gtggcagcag      1320
gggaacgtct tctcatgctc cgtgatgcat gaggctctgc acaaccacta cacgcagaag      1380
agcctctccc tgtctcccgg gaaatga                                         1407

<210> SEQ ID NO 8
<211> LENGTH: 711
<212> TYPE: DNA
<213> ORGANISM: Artificial Sequence
<220> FEATURE:
<223> OTHER INFORMATION: Synthetic Construct

<400> SEQUENCE: 8
atgggatgga gctgtatcat cctcttcttg gtagcaacag ctacaggtgt ccactccgac        60
atccagctga cccagagccc aagcagcctg agcgccagcg tgggtgacag agtgaccatc       120
acctgtagtg tcagctcaag tataagttcc aacaacttgc actggtacca gcagaagcca       180
ggtaaggctc caaagccatg gatctacggc acatccaacc tggcttctgg tgtgccaagc       240
agattcagcg gtagcggtag cggtaccgac tacaccttca ccatcagcag cctccagcca       300
gaggacatcg ccacctacta ctgccaacag tggagtagtt acccgtacat gtacacgttc       360
ggccaaggga ccaaggtgga aatcaaacga actgtggctg caccatctgt cttcatcttc       420
ccgccatctg atgagcagtt gaaatctgga actgcctctg ttgtgtgcct gctgaataac       480
ttctatccca gagaggccaa agtacagtgg aaggtggata acgccctcca atcgggtaac       540
tcccaggaga gtgtcacaga gcaggacagc aaggacagca cctacagcct cagcagcacc       600
ctgacgctga gcaaagcaga ctacgagaaa cacaaagtct acgcctgcga agtcacccat       660
cagggcctga gctcgcccgt cacaaagagc ttcaacaggg gagagtgtta a               711

<210> SEQ ID NO 9
<211> LENGTH: 859
<212> TYPE: PRT
<213> ORGANISM: Mus musculus

<400> SEQUENCE: 9

Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
```

```
            20                  25                  30
Leu Ser Leu Ser Thr Ala Val Lys Glu Leu Ile Glu Asn Ser Val Asp
         35                  40                  45

Ala Gly Ala Thr Thr Ile Asp Leu Arg Leu Lys Asp Tyr Gly Val Asp
 50                  55                  60

Leu Ile Glu Val Ser Asp Asn Gly Cys Gly Val Glu Glu Asn Phe
 65                  70                  75                  80

Glu Gly Leu Ala Leu Lys His His Thr Ser Lys Ile Gln Glu Phe Ala
                 85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr Arg Leu Val Phe Asp His Asn Gly Lys Ile Thr
    130                 135                 140

Gln Lys Thr Pro Tyr Pro Arg Pro Lys Gly Thr Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
        195                 200                 205

Gly Lys Arg His Ala Val Val Cys Thr Ser Gly Thr Ser Gly Met Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255

Leu Ser Thr Ser Gly Arg His Lys Thr Phe Ser Thr Phe Arg Ala Ser
            260                 265                 270

Phe His Ser Ala Arg Thr Ala Pro Gly Gly Val Gln Gln Thr Gly Ser
        275                 280                 285

Phe Ser Ser Ser Ile Arg Gly Pro Val Thr Gln Gln Arg Ser Leu Ser
    290                 295                 300

Leu Ser Met Arg Phe Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Ala Asn
        355                 360                 365

Lys Leu Asn Val Asn Gln Gln Pro Leu Leu Asp Val Glu Gly Asn Leu
    370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
            420                 425                 430

Ile Lys Ser Arg Gly Pro Glu Thr Ala Glu Leu Thr Arg Ser Phe Pro
        435                 440                 445
```

```
Ser Glu Lys Arg Gly Val Leu Ser Ser Tyr Pro Ser Asp Val Ile Ser
    450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
                485                 490                 495

Leu Ser Ser Thr Ser Ala Gly Ser Glu Glu Glu Phe Ser Thr Pro Glu
            500                 505                 510

Val Ala Ser Ser Phe Ser Ser Asp Tyr Asn Val Ser Ser Leu Glu Asp
        515                 520                 525

Arg Pro Ser Gln Glu Thr Ile Asn Cys Gly Asp Leu Asp Cys Arg Pro
530                 535                 540

Pro Gly Thr Gly Gln Ser Leu Lys Pro Glu Asp His Gly Tyr Gln Cys
545                 550                 555                 560

Lys Ala Leu Pro Leu Ala Arg Leu Ser Pro Thr Asn Ala Lys Arg Phe
                565                 570                 575

Lys Thr Glu Glu Arg Pro Ser Asn Val Asn Ile Ser Gln Arg Leu Pro
            580                 585                 590

Gly Pro Gln Ser Thr Ser Ala Ala Glu Val Asp Val Ala Ile Lys Met
        595                 600                 605

Asn Lys Arg Ile Val Leu Leu Glu Phe Ser Leu Ser Ser Leu Ala Lys
610                 615                 620

Arg Met Lys Gln Leu Gln His Leu Lys Ala Gln Asn Lys His Glu Leu
625                 630                 635                 640

Ser Tyr Arg Lys Phe Arg Ala Lys Ile Cys Pro Gly Glu Asn Gln Ala
                645                 650                 655

Ala Glu Asp Glu Leu Arg Lys Gly Ile Ser Lys Ser Met Phe Ala Glu
            660                 665                 670

Met Glu Ile Leu Gly Gln Phe Asn Leu Gly Phe Ile Val Thr Lys Leu
        675                 680                 685

Lys Glu Asp Leu Phe Leu Val Asp Gln His Ala Ala Asp Glu Lys Tyr
690                 695                 700

Asn Phe Glu Met Leu Gln Gln His Thr Val Leu Gln Ala Gln Arg Leu
705                 710                 715                 720

Ile Thr Pro Gln Thr Leu Asn Leu Thr Ala Val Asn Glu Ala Val Leu
                725                 730                 735

Ile Glu Asn Leu Glu Ile Phe Arg Lys Asn Gly Phe Asp Phe Val Ile
            740                 745                 750

Asp Glu Asp Ala Pro Val Thr Glu Arg Ala Lys Leu Ile Ser Leu Pro
        755                 760                 765

Thr Ser Lys Asn Trp Thr Phe Gly Pro Gln Asp Ile Asp Glu Leu Ile
770                 775                 780

Phe Met Leu Ser Asp Ser Pro Gly Val Met Cys Arg Pro Ser Arg Val
785                 790                 795                 800

Arg Gln Met Phe Ala Ser Arg Ala Cys Arg Lys Ser Val Met Ile Gly
                805                 810                 815

Thr Ala Leu Asn Ala Ser Glu Met Lys Lys Leu Ile Thr His Met Gly
            820                 825                 830

Glu Met Asp His Pro Trp Asn Cys Pro His Gly Arg Pro Thr Met Arg
        835                 840                 845

His Val Ala Asn Leu Asp Val Ile Ser Gln Asn
850                 855
```

<210> SEQ ID NO 10
<211> LENGTH: 3056
<212> TYPE: DNA
<213> ORGANISM: Mus musculus

<400> SEQUENCE: 10

| | | | | | | |
|---|---|---|---|---|---|---|
| gaattccggt | gaaggtcctg | aagaatttcc | agattcctga | gtatcattgg | aggagacaga | 60 |
| taacctgtcg | tcaggtaacg | atggtgtata | tgcaacagaa | atgggtgttc | ctggagacgc | 120 |
| gtcttttccc | gagagcggca | ccgcaactct | cccgcggtga | ctgtgactgg | aggagtcctg | 180 |
| catccatgga | gcaaaccgaa | ggcgtgagta | cagaatgtgc | taaggccatc | aagcctattg | 240 |
| atgggaagtc | agtccatcaa | atttgttctg | ggcaggtgat | actcagttta | agcaccgctg | 300 |
| tgaaggagtt | gatagaaaat | agtgtagatg | ctggtgctac | tactattgat | ctaaggctta | 360 |
| aagactatgg | ggtggacctc | attgaagttt | cagacaatgg | atgtggggta | gaagaagaaa | 420 |
| actttgaagg | tctagctctg | aaacatcaca | catctaagat | tcaagagttt | gccgacctca | 480 |
| cgcaggttga | aactttcggc | tttcgggggg | aagctctgag | ctctctgtgt | gcactaagtg | 540 |
| atgtcactat | atctacctgc | cacgggtctg | caagcgttgg | gactcgactg | gtgtttgacc | 600 |
| ataatgggaa | aatcacccag | aaaactccct | accccgacc | taaaggaacc | acagtcagtg | 660 |
| tgcagcactt | attttataca | ctacccgtgc | gttacaaaga | gtttcagagg | aacattaaaa | 720 |
| aggagtattc | caaaatggtg | caggtcttac | aggcgtactg | tatcatctca | gcaggcgtcc | 780 |
| gtgtaagctg | cactaatcag | ctcggacagg | ggaagcggca | cgctgtggtg | tgcacaagcg | 840 |
| gcacgtctgg | catgaaggaa | aatatcgggt | ctgtgtttgg | ccagaagcag | ttgcaaagcc | 900 |
| tcattccttt | tgttcagctg | cccctagtg | acgctgtgtg | tgaagagtac | ggcctgagca | 960 |
| cttcaggacg | ccacaaaacc | ttttctacgt | ttcgggcttc | atttcacagt | gcacgcacgg | 1020 |
| cgccgggagg | agtgcaacag | acaggcagtt | tttcttcatc | aatcagaggc | cctgtgaccc | 1080 |
| agcaaaggtc | tctaagcttg | tcaatgaggt | tttatcacat | gtataaccgg | catcagtacc | 1140 |
| catttgtcgt | ccttaacgtt | tccgttgact | cagaatgtgt | ggatattaat | gtaactccag | 1200 |
| ataaaaggca | aattctacta | caagaagaga | agctattgct | ggccgtttta | aagacctcct | 1260 |
| tgataggaat | gtttgacagt | gatgcaaaca | agcttaatgt | caaccagcag | ccactgctag | 1320 |
| atgttgaagg | taacttagta | aagctgcata | ctgcagaact | agaaaagcct | gtgccaggaa | 1380 |
| agcaagataa | ctctccttca | ctgaagagca | cagcagacga | gaaagggta | gcatccatct | 1440 |
| ccaggctgag | agaggccttt | tctcttcatc | ctactaaaga | gatcaagtct | aggggtccag | 1500 |
| agactgctga | actgacacgg | agttttccaa | gtgagaaaag | gggcgtgtta | tcctcttatc | 1560 |
| cttcagacgt | catctcttac | agaggcctcc | gtggctcgca | ggacaaattg | gtgagtccca | 1620 |
| cggacagccc | tggtgactgt | atggacagag | agaaaataga | aaaagactca | gggctcagca | 1680 |
| gcacctcagc | tggctctgag | gaagagttca | gcacccaga | agtggccagt | agctttagca | 1740 |
| gtgactataa | cgtgagctcc | ctagaagaca | gaccttctca | ggaaaccata | aactgtggtg | 1800 |
| acctggactg | ccgtcctcca | ggtacaggac | agtccttgaa | gccagaagac | catggatatc | 1860 |
| aatgcaaagc | tctacctcta | gctcgtctgt | cacccacaaa | tgccaagcgc | ttcaagacag | 1920 |
| aggaaagacc | ctcaaatgtc | aacatttctc | aaagattgcc | tggtcctcag | agcacctcag | 1980 |
| cagctgaggt | cgatgtagcc | ataaaaatga | ataagagaat | cgtgctcctc | gagttctctc | 2040 |
| tgagttctct | agctaagcga | atgaagcagt | tacagcacct | aaaggcgcag | aacaaacatg | 2100 |
| aactgagtta | cagaaaattt | agggccaaga | tttgccctgg | agaaaaccaa | gcagcagaag | 2160 |

```
atgaactcag aaaagagatt agtaaatcga tgtttgcaga gatggagatc ttgggtcagt    2220
ttaacctggg atttatagta accaaactga aagaggacct cttcctggtg accagcatg    2280 ctgcggatga aagtacaac tttgagatgc tgcagcagca cacggtgctc caggcgcaga    2340
ggctcatcac accccagact ctgaacttaa ctgctgtcaa tgaagctgta ctgatagaaa    2400
atctggaaat attcagaaag aatggctttg actttgtcat tgatgaggat gctccagtca    2460
ctgaaagggc taaattgatt tccttaccaa ctagtaaaaa ctggaccttt ggaccccaag    2520
atatagatga actgatcttt atgttaagtg acagccctgg ggtcatgtgc cggccctcac    2580
gagtcagaca gatgtttgct tccagagcct gtcggaagtc agtgatgatt ggaacggcgc    2640
tcaatgcgag cgagatgaag aagctcatca cccacatggg tgagatggac caccctgga    2700 actgcccca cggcaggcca accatgaggc acgttgccaa tctggatgtc atctctcaga    2760
actgacacac cccttgtagc atagagttta ttacagattg ttcggtttgc aaagagaagg    2820 tttaagtaa tctgattatc gttgtacaaa aattagcatg ctgctttaat gtactggatc    2880
catttaaaag cagtgttaag gcaggcatga tggagtgttc ctctagctca gctacttggg    2940
tgatccggtg ggagctcatg tgagcccagg actttgagac cactccgagc cacattcatg    3000
agactcaatt caaggacaaa aaaaaaaaga tattttgaa gccttttaaa aaaaa    3056
```

<210> SEQ ID NO 11
<211> LENGTH: 862
<212> TYPE: PRT
<213> ORGANISM: Homo sapiens

<400> SEQUENCE: 11

```
Met Glu Arg Ala Glu Ser Ser Thr Glu Pro Ala Lys Ala Ile Lys
1               5                   10                  15

Pro Ile Asp Arg Lys Ser Val His Gln Ile Cys Ser Gly Gln Val
                20                  25                  30

Leu Ser Leu Ser Thr Ala Val Lys Glu Leu Val Glu Asn Ser Leu Asp
            35                  40                  45

Ala Gly Ala Thr Asn Ile Asp Leu Lys Leu Lys Asp Tyr Gly Val Asp
        50                  55                  60

Leu Ile Glu Val Ser Asp Asn Gly Cys Gly Val Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr Arg Leu Met Phe Asp His Asn Gly Lys Ile Ile
    130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Thr Gly Gly Ser Pro Ser Ile Lys
```

-continued

```
            210                 215                 220
Glu Asn Ile Gly Ser Val Phe Gly Gln Lys Gln Leu Gln Ser Leu Ile
225                 230                 235                 240

Pro Phe Val Gln Leu Pro Ser Asp Ser Val Cys Glu Glu Tyr Gly
                245                 250                 255

Leu Ser Cys Ser Asp Ala Leu His Asn Leu Phe Tyr Ile Ser Gly Phe
                260                 265                 270

Ile Ser Gln Cys Thr His Gly Val Gly Arg Ser Ser Thr Asp Arg Gln
                275                 280                 285

Phe Phe Phe Ile Asn Arg Arg Pro Cys Asp Pro Ala Lys Val Cys Arg
        290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Glu Lys Leu Leu Leu
                340                 345                 350

Ala Val Leu Lys Thr Ser Leu Ile Gly Met Phe Asp Ser Asp Val Asn
                355                 360                 365

Lys Leu Asn Val Ser Gln Gln Pro Leu Leu Asp Val Glu Gly Asn Leu
        370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Glu Lys Lys Asp Val Ser
                405                 410                 415

Ile Ser Arg Leu Arg Glu Ala Phe Ser Leu Arg His Thr Thr Glu Asn
                420                 425                 430

Lys Pro His Ser Pro Lys Thr Pro Glu Pro Arg Arg Ser Pro Leu Gly
                435                 440                 445

Gln Lys Arg Gly Met Leu Ser Ser Ser Thr Ser Gly Ala Ile Ser Asp
        450                 455                 460

Lys Gly Val Leu Arg Pro Gln Lys Glu Ala Val Ser Ser Ser His Gly
465                 470                 475                 480

Pro Ser Asp Pro Thr Asp Arg Ala Glu Val Glu Lys Asp Ser Gly His
                485                 490                 495

Gly Ser Thr Ser Val Asp Ser Glu Gly Phe Ser Ile Pro Asp Thr Gly
                500                 505                 510

Ser His Cys Ser Ser Glu Tyr Ala Ala Ser Ser Pro Gly Asp Arg Gly
                515                 520                 525

Ser Gln Glu His Val Asp Ser Gln Glu Lys Ala Pro Glu Thr Asp Asp
        530                 535                 540

Ser Phe Ser Asp Val Asp Cys His Ser Asn Gln Glu Asp Thr Gly Cys
545                 550                 555                 560

Lys Phe Arg Val Leu Pro Gln Pro Thr Asn Leu Ala Thr Pro Asn Thr
                565                 570                 575

Lys Arg Phe Lys Lys Glu Glu Ile Leu Ser Ser Ser Asp Ile Cys Gln
                580                 585                 590

Lys Leu Val Asn Thr Gln Asp Met Ser Ala Ser Gln Val Asp Val Ala
                595                 600                 605

Val Lys Ile Asn Lys Lys Val Val Pro Leu Asp Phe Ser Met Ser Ser
        610                 615                 620

Leu Ala Lys Arg Ile Lys Gln Leu His His Glu Ala Gln Gln Ser Glu
625                 630                 635                 640
```

Gly Glu Gln Asn Tyr Arg Lys Phe Arg Ala Lys Ile Cys Pro Gly Glu
                645                 650                 655

Asn Gln Ala Ala Glu Asp Glu Leu Arg Lys Glu Ile Ser Lys Thr Met
            660                 665                 670

Phe Ala Glu Met Glu Ile Ile Gly Gln Phe Asn Leu Gly Phe Ile Ile
        675                 680                 685

Thr Lys Leu Asn Glu Asp Ile Phe Ile Val Asp Gln His Ala Thr Asp
    690                 695                 700

Glu Lys Tyr Asn Phe Glu Met Leu Gln Gln His Thr Val Leu Gln Gly
705                 710                 715                 720

Gln Arg Leu Ile Ala Pro Gln Thr Leu Asn Leu Thr Ala Val Asn Glu
            725                 730                 735

Ala Val Leu Ile Glu Asn Leu Glu Ile Phe Arg Lys Asn Gly Phe Asp
        740                 745                 750

Phe Val Ile Asp Glu Asn Ala Pro Val Thr Glu Arg Ala Lys Leu Ile
    755                 760                 765

Ser Leu Pro Thr Ser Lys Asn Trp Thr Phe Gly Pro Gln Asp Val Asp
770                 775                 780

Glu Leu Ile Phe Met Leu Ser Asp Ser Pro Gly Val Met Cys Arg Pro
785                 790                 795                 800

Ser Arg Val Lys Gln Met Phe Ala Ser Arg Ala Cys Arg Lys Ser Val
            805                 810                 815

Met Ile Gly Thr Ala Leu Asn Thr Ser Glu Met Lys Lys Leu Ile Thr
        820                 825                 830

His Met Gly Glu Met Asp His Pro Trp Asn Cys Pro His Gly Arg Pro
    835                 840                 845

Thr Met Arg His Ile Ala Asn Leu Gly Val Ile Ser Gln Asn
    850                 855                 860

<210> SEQ ID NO 12
<211> LENGTH: 2771
<212> TYPE: DNA
<213> ORGANISM: Homo sapiens

<400> SEQUENCE: 12

```
cgaggcggat cgggtgttgc atccatggag cgagctgaga gctcgagtac agaacctgct    60
aaggccatca aacctattga tcggaagtca gtccatcaga tttgctctgg gcaggtggta   120
ctgagtctaa gcactgcggt aaaggagtta gtagaaaaca gtctggatgc tggtgccact   180
aatattgatc taaagcttaa ggactatgga gtggatctta ttgaagtttc agacaatgga   240
tgtggggtag aagaagaaaa cttcgaaggc ttaactctga acatcacac atctaagatt   300
caagagtttg ccgacctaac tcaggttgaa acttttggct tcgggggga agctctgagc   360
tcactttgtg cactgagcga tgtcaccatt tctacctgcc acgcatcggc gaaggttgga   420
actcgactga tgtttgatca aatgggaaa attatccaga aaaccccta cccccgcccc   480
agagggacca cagtcagcgt gcagcagtta ttttccacac tacctgtgcg ccataaggaa   540
tttcaaagga atattaagaa ggagtatgcc aaaatggtcc aggtcttaca tgcatactgt   600
atcatttcag caggcatccg tgtaagttgc accaatcagc ttggacaagg aaaacgacag   660
cctgtggtat gcacaggtgg aagccccagc ataaggaaa atatcggctc tgtgtttggg   720
cagaagcagt tgcaaagcct cattccttt gttcagctgc ccctagtga ctccgtgtgt   780
gaagagtacg gtttgagctg ttcggatgct ctgcataatc ttttttacat ctcaggtttc   840
```

```
atttcacaat gcacgcatgg agttggaagg agttcaacag acagacagtt tttctttatc    900
aaccggcggc cttgtgaccc agcaaaggtc tgcagactcg tgaatgaggt ctaccacatg    960
tataatcgac accagtatcc atttgttgtt cttaacattt ctgttgattc agaatgcgtt   1020
gatatcaatg ttactccaga taaaaggcaa attttgctac aagaggaaaa gcttttgttg   1080
gcagttttaa agacctcttt gataggaatg tttgatagtg atgtcaacaa gctaaatgtc   1140
agtcagcagc cactgctgga tgttgaaggt aacttaataa aaatgcatgc agcggatttg   1200
gaaaagccca tggtagaaaa gcaggatcaa tccccttcat taaggactgg agaagaaaaa   1260
aaagacgtgt ccatttccag actgcgagag gccttttctc ttcgtcacac aacagagaac   1320
aagcctcaca gcccaaagac tccagaacca agaaggagcc ctctaggaca gaaaaggggt   1380
atgctgtctt ctagcacttc aggtgccatc tctgacaaag gcgtcctgag acctcagaaa   1440
gaggcagtga gttccagtca cggacccagt gaccctacgg acagagcgga ggtggagaag   1500
gactcggggc acggcagcac ttccgtggat tctgaggggt tcagcatccc agacacgggc   1560
agtcactgca gcagcgagta tgcggccagc tccccagggg acaggggctc gcaggaacat   1620
gtggactctc aggagaaagc gcctgaaact gacgactctt tttcagatgt ggactgccat   1680
tcaaaccagg aagataccgg atgtaaattt cgagttttgc ctcagccaac taatctcgca   1740
accccaaaca caaagcgttt taaaaaagaa gaaattcttt ccagttctga catttgtcaa   1800
aagttagtaa atactcagga catgtcagcc tctcaggttg atgtagctgt gaaaattaat   1860
aagaaagttg tgcccctgga cttttctatg agttctttag ctaaacgaat aaagcagtta   1920
catcatgaag cacagcaaag tgaaggggaa cagaattaca ggaagtttag ggcaaagatt   1980
tgtcctggag aaaatcaagc agccgaagat gaactaagaa aagagataag taaaacgatg   2040
tttgcagaaa tggaaatcat tggtcagttt aacctgggat ttataataac caaactgaat   2100
gaggatatct tcatagtgga ccagcatgcc acggacgaga agtataactt cgagatgctg   2160
cagcagcaca ccgtgctcca ggggcagagg ctcatagcac ctcagactct caacttaact   2220
gctgttaatg aagctgttct gatagaaaat ctggaaatat ttagaaagaa tggctttgat   2280
tttgttatcg atgaaaatgc tccagtcact gaaagggcta aactgatttc cttgccaact   2340
agtaaaaact ggaccttcgg accccaggac gtcgatgaac tgatcttcat gctgagcgac   2400
agccctgggg tcatgtgccg gccttcccga gtcaagcaga tgtttgcctc cagagcctgc   2460
cggaagtcgg tgatgattgg gactgctctt aacacaagcg agatgaagaa actgatcacc   2520
cacatggggg agatggacca cccctggaac tgtccccatg gaaggccaac catgagacac   2580
atcgccaacc tgggtgtcat ttctcagaac tgaccgtagt cactgtatgg aataattggt   2640
tttatcgcag atttttatgt tttgaaagac agagtcttca ctaacctttt ttgttttaaa   2700
atgaaacctg ctacttaaaa aaaatacaca tcacacccat ttaaaagtga tcttgagaac   2760
cttttcaaac c                                                        2771
```

<210> SEQ ID NO 13
<211> LENGTH: 932
<212> TYPE: PRT
<213> ORGANISM: Homo sapiens

<400> SEQUENCE: 13

Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
            20                  25                  30

```
Leu Asp Ala Gly Ala Thr Ser Val Asp Val Lys Leu Glu Asn Tyr Gly
         35                  40                  45

Phe Asp Lys Ile Glu Val Arg Asp Asn Gly Glu Gly Ile Lys Ala Val
 50                  55                  60

Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
                 85                  90                  95

Leu Gly Ser Ile Cys Cys Ile Ala Glu Val Leu Ile Thr Thr Arg Thr
                100                 105                 110

Ala Ala Asp Asn Phe Ser Thr Gln Tyr Val Leu Asp Gly Ser Gly His
                115                 120                 125

Ile Leu Ser Gln Lys Pro Ser His Leu Gly Gln Gly Thr Thr Val Thr
                130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
                180                 185                 190

Asn Lys Ala Val Ile Trp Gln Lys Ser Arg Val Ser Asp His Lys Met
                195                 200                 205

Ala Leu Met Ser Val Leu Gly Thr Ala Val Met Asn Asn Met Glu Ser
                210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
                260                 265                 270

Leu Lys Leu Ile Arg His His Tyr Asn Leu Lys Cys Leu Lys Glu Ser
                275                 280                 285

Thr Arg Leu Tyr Pro Val Phe Phe Leu Lys Ile Asp Val Pro Thr Ala
                290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
                340                 345                 350

Val Ser Ala Ala Asp Ile Val Leu Ser Lys Thr Ala Glu Thr Asp Val
                355                 360                 365

Leu Phe Asn Lys Val Glu Ser Ser Gly Lys Asn Tyr Ser Asn Val Asp
                370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
                420                 425                 430

Lys Asn Ala Phe Gln Asp Ile Ser Met Ser Asn Val Ser Trp Glu Asn
                435                 440                 445
```

```
Ser Gln Thr Glu Tyr Ser Lys Thr Cys Phe Ile Ser Ser Val Lys His
    450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495

Glu Trp Ser Arg Gly Asn Ile Leu Lys Asn Ser Val Gly Glu Asn Ile
            500                 505                 510

Glu Pro Val Lys Ile Leu Val Pro Glu Lys Ser Leu Pro Cys Lys Val
            515                 520                 525

Ser Asn Asn Asn Tyr Pro Ile Pro Glu Gln Met Asn Leu Asn Glu Asp
530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Lys Pro Met Ser
                565                 570                 575

Ala Ser Ala Leu Phe Val Gln Asp His Arg Pro Gln Phe Leu Ile Glu
            580                 585                 590

Asn Pro Lys Thr Ser Leu Glu Asp Ala Thr Leu Gln Ile Glu Glu Leu
            595                 600                 605

Trp Lys Thr Leu Ser Glu Glu Lys Leu Lys Tyr Glu Glu Lys Ala
            610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Lys Ile Lys Pro
                645                 650                 655

Thr Ser Ala Trp Asn Leu Ala Gln Lys His Lys Leu Lys Thr Ser Leu
            660                 665                 670

Ser Asn Gln Pro Lys Leu Asp Glu Leu Leu Gln Ser Gln Ile Glu Lys
            675                 680                 685

Arg Arg Ser Gln Asn Ile Lys Met Val Gln Ile Pro Phe Ser Met Lys
            690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                725                 730                 735

Leu Met Thr Ser Lys Thr Glu Val Met Leu Leu Asn Pro Tyr Arg Val
            740                 745                 750

Glu Glu Ala Leu Leu Phe Lys Arg Leu Leu Glu Asn His Lys Leu Pro
            755                 760                 765

Ala Glu Pro Leu Glu Lys Pro Ile Met Leu Thr Glu Ser Leu Phe Asn
770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                805                 810                 815

Gly Phe Lys Ile Lys Leu Ile Pro Gly Val Ser Ile Thr Glu Asn Tyr
            820                 825                 830

Leu Glu Ile Glu Gly Met Ala Asn Cys Leu Pro Phe Tyr Gly Val Ala
            835                 840                 845

Asp Leu Lys Glu Ile Leu Asn Ala Ile Leu Asn Arg Asn Ala Lys Glu
850                 855                 860

Val Tyr Glu Cys Arg Pro Arg Lys Val Ile Ser Tyr Leu Glu Gly Glu
```

```
                865                 870                 875                 880
Ala Val Arg Leu Ser Arg Gln Leu Pro Met Tyr Leu Ser Lys Glu Asp
                    885                 890                 895

Ile Gln Asp Ile Ile Tyr Arg Met Lys His Gln Phe Gly Asn Glu Ile
                900                 905                 910

Lys Glu Cys Val His Gly Arg Pro Phe Phe His His Leu Thr Tyr Leu
        915                 920                 925

Pro Glu Thr Thr
    930

<210> SEQ ID NO 14
<211> LENGTH: 3063
<212> TYPE: DNA
<213> ORGANISM: Homo sapiens

<400> SEQUENCE: 14
ggcacgagtg gctgcttgcg gctagtggat ggtaattgcc tgcctcgcgc tagcagcaag      60
ctgctctgtt aaaagcgaaa atgaaacaat tgcctgcggc aacagttcga ctcctttcaa     120
gttctcagat catcacttcg gtggtcagtg ttgtaaaaga gcttattgaa aactccttgg     180
atgctggtgc cacaagcgta gatgttaaac tggagaacta tggatttgat aaaattgagg     240
tgcgagataa cggggagggt atcaaggctg ttgatgcacc tgtaatggca atgaagtact     300
acacctcaaa aataaatagt catgaagatc ttgaaaattt gacaacttac ggttttcgtg     360
gagaagcctt ggggtcaatt tgttgtatag ctgaggtttt aattacaaca agaacggctg     420
ctgataattt tagcacccag tatgttttag atggcagtgg ccacatactt tctcagaaac     480
cttcacatct tggtcaaggt acaactgtaa ctgctttaag attatttaag aatctacctg     540
taagaaagca gttttactca actgcaaaaa atgtaaaaga tgaaataaaa aagatccaag     600
atctcctcat gagctttggt atccttaaac ctgacttaag gattgtcttt gtacataaca     660
aggcagttat ttggcagaaa agcagagtat cagatcacaa gatggctctc atgtcagttc     720
tggggactgc tgttatgaac aatatggaat cctttcagta ccactctgaa gaatctcaga     780
tttatctcag tggatttctt ccaaagtgtg atgcagacca ctctttcact agtctttcaa     840
caccagaaag aagtttcatc ttcataaaca gtcgaccagt acatcaaaaa gatatcttaa     900
agttaatccg acatcattac aatctgaaat gcctaaagga atctactcgt ttgtatcctg     960
ttttctttct gaaaatcgat gttcctacag ctgatgttga tgtaaattta acaccagata    1020
aaagccaagt attattacaa aataaggaat ctgttttaat tgctcttgaa atctgatgac    1080
gacttgttac tggaccatta cctagtacaa attcttatga aaataataaa acagatgttt    1140
ccgcagctga catcgttctt agtaaaacag cagaaacaga tgtgcttttt aataaagtgg    1200
aatcatctgg aaagaattat tcaaatgttg atacttcagt cattccattc caaaatgata    1260
tgcataatga tgaatctgga aaaaacactg atgattgttt aaatcaccag ataagtattg    1320
gtgactttgg ttatggtcat tgtagtagtg aaatttctaa cattgataaa aacactaaga    1380
atgcatttca ggacatttca atgagtaatg tatcatggga gaactctcag acggaatata    1440
gtaaaacttg ttttataagt tccgttaagc acacccagtc agaaaatggc aataaagacc    1500
atatagatga gagtggggaa aatgaggaag aagcaggtct tgaaaactct tcggaaattt    1560
ctgcagatga gtggagcagg ggaaatatac ttaaaaattc agtgggagag aatattgaac    1620
ctgtgaaaat tttagtgcct gaaaaaagtt taccatgtaa agtaagtaat aataattatc    1680
caatccctga acaaatgaat cttaatgaag attcatgtaa caaaaaatca aatgtaatag    1740
```

```
ataataaatc tggaaaagtt acagcttatg atttacttag caatcgagta atcaagaaac    1800
ccatgtcagc aagtgctctt tttgttcaag atcatcgtcc tcagtttctc atagaaaatc    1860
ctaagactag tttagaggat gcaacactac aaattgaaga actgtggaag acattgagtg    1920
aagaggaaaa actgaaatat gaagagaagg ctactaaaga cttggaacga tacaatagtc    1980
aaatgaagag agccattgaa caggagtcac aaatgtcact aaaagatggc agaaaaaaga    2040
taaaacccac cagcgcatgg aatttggccc agaagcacaa gttaaaaacc tcattatcta    2100
atcaaccaaa acttgatgaa ctccttcagt cccaaattga aaaagaagg agtcaaaata    2160 ttaaaatggt acagatcccc ttttctatga aaaacttaaa aataaattt aagaaacaaa    2220 acaaagttga cttagaagag aaggatgaac cttgcttgat ccacaatctc aggtttcctg    2280
atgcatggct aatgacatcc aaaacagagg taatgttatt aaatccatat agagtagaag    2340
aagccctgct atttaaaaga cttcttgaga atcataaact tcctgcagag ccactggaaa    2400
agccaattat gttaacagag agtctttta atggatctca ttatttagac gttttatata    2460
aaatgacagc agatgaccaa agatacagtg gatcaactta cctgtctgat cctcgtctta    2520
cagcgaatgg tttcaagata aaattgatac caggagtttc aattactgaa aattacttgg    2580
aaatagaagg aatggctaat tgtctcccat tctatggagt agcagattta aaagaaattc    2640
ttaatgctat attaaacaga aatgcaaagg aagtttatga atgtagacct cgcaaagtga    2700
taagttattt agagggagaa gcagtgcgtc tatccagaca attacccatg tacttatcaa    2760
aagaggacat ccaagacatt atctacagaa tgaagcacca gtttggaaat gaaattaaag    2820
agtgtgttca tggtcgccca ttttttcatc atttaaccta tcttccagaa actacatgat    2880
taaatatgtt taagaagatt agttaccatt gaaattggtt ctgtcataaa acagcatgag    2940
tctggtttta aattatcttt gtattatgtg tcacatggtt attttttaaa tgaggattca    3000
ctgacttgtt tttatattga aaaagttcc acgtattgta gaaaacgtaa ataaactaat    3060
aac                                                                  3063
```

<210> SEQ ID NO 15
<211> LENGTH: 934
<212> TYPE: PRT
<213> ORGANISM: Homo sapiens

<400> SEQUENCE: 15

```
Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125
```

-continued

```
Ser Gln Phe Glu Asp Ile Leu Phe Gly Asn Asn Asp Met Ser Ala Ser
    130                 135                 140
Ile Gly Val Val Gly Val Lys Met Ser Ala Val Asp Gly Gln Arg Gln
145                 150                 155                 160
Val Gly Val Gly Tyr Val Asp Ser Ile Gln Arg Lys Leu Gly Leu Cys
                165                 170                 175
Glu Phe Pro Asp Asn Asp Gln Phe Ser Asn Leu Glu Ala Leu Leu Ile
            180                 185                 190
Gln Ile Gly Pro Lys Glu Cys Val Leu Pro Gly Gly Glu Thr Ala Gly
        195                 200                 205
Asp Met Gly Lys Leu Arg Gln Ile Ile Gln Arg Gly Gly Ile Leu Ile
    210                 215                 220
Thr Glu Arg Lys Lys Ala Asp Phe Ser Thr Lys Asp Ile Tyr Gln Asp
225                 230                 235                 240
Leu Asn Arg Leu Leu Lys Gly Lys Lys Gly Glu Gln Met Asn Ser Ala
                245                 250                 255
Val Leu Pro Glu Met Glu Asn Gln Val Ala Val Ser Ser Leu Ser Ala
            260                 265                 270
Val Ile Lys Phe Leu Glu Leu Leu Ser Asp Asp Ser Asn Phe Gly Gln
        275                 280                 285
Phe Glu Leu Thr Thr Phe Asp Phe Ser Gln Tyr Met Lys Leu Asp Ile
    290                 295                 300
Ala Ala Val Arg Ala Leu Asn Leu Phe Gln Gly Ser Val Glu Asp Thr
305                 310                 315                 320
Thr Gly Ser Gln Ser Leu Ala Ala Leu Leu Asn Lys Cys Lys Thr Pro
                325                 330                 335
Gln Gly Gln Arg Leu Val Asn Gln Trp Ile Lys Gln Pro Leu Met Asp
            340                 345                 350
Lys Asn Arg Ile Glu Glu Arg Leu Asn Leu Val Glu Ala Phe Val Glu
        355                 360                 365
Asp Ala Glu Leu Arg Gln Thr Leu Gln Glu Asp Leu Leu Arg Arg Phe
    370                 375                 380
Pro Asp Leu Asn Arg Leu Ala Lys Lys Phe Gln Arg Gln Ala Ala Asn
385                 390                 395                 400
Leu Gln Asp Cys Tyr Arg Leu Tyr Gln Gly Ile Asn Gln Leu Pro Asn
                405                 410                 415
Val Ile Gln Ala Leu Glu Lys His Glu Gly Lys His Gln Lys Leu Leu
            420                 425                 430
Leu Ala Val Phe Val Thr Pro Leu Thr Asp Leu Arg Ser Asp Phe Ser
        435                 440                 445
Lys Phe Gln Glu Met Ile Glu Thr Thr Leu Asp Met Asp Gln Val Glu
    450                 455                 460
Asn His Glu Phe Leu Val Lys Pro Ser Phe Asp Pro Asn Leu Ser Glu
465                 470                 475                 480
Leu Arg Glu Ile Met Asn Asp Leu Glu Lys Lys Met Gln Ser Thr Leu
                485                 490                 495
Ile Ser Ala Ala Arg Asp Leu Gly Leu Asp Pro Gly Lys Gln Ile Lys
            500                 505                 510
Leu Asp Ser Ser Ala Gln Phe Gly Tyr Tyr Phe Arg Val Thr Cys Lys
        515                 520                 525
Glu Glu Lys Val Leu Arg Asn Asn Lys Asn Phe Ser Thr Val Asp Ile
530                 535                 540
Gln Lys Asn Gly Val Lys Phe Thr Asn Ser Lys Leu Thr Ser Leu Asn
```

Glu Glu Tyr Thr Lys Asn Lys Thr Glu Tyr Glu Glu Ala Gln Asp Ala
545                 550                 555                 560
                565                 570                 575

Ile Val Lys Glu Ile Val Asn Ile Ser Ser Gly Tyr Val Glu Pro Met
                580                 585                 590

Gln Thr Leu Asn Asp Val Leu Ala Gln Leu Asp Ala Val Val Ser Phe
                595                 600                 605

Ala His Val Ser Asn Gly Ala Pro Val Pro Tyr Val Arg Pro Ala Ile
610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
                660                 665                 670

Gly Gly Lys Ser Thr Tyr Ile Arg Gln Thr Gly Val Ile Val Leu Met
                675                 680                 685

Ala Gln Ile Gly Cys Phe Val Pro Cys Glu Ser Ala Glu Val Ser Ile
690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
                740                 745                 750

Gly Thr Ser Thr Tyr Asp Gly Phe Gly Leu Ala Trp Ala Ile Ser Glu
                755                 760                 765

Tyr Ile Ala Thr Lys Ile Gly Ala Phe Cys Met Phe Ala Thr His Phe
                770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
                820                 825                 830

Leu Ala Asn Phe Pro Lys His Val Ile Glu Cys Ala Lys Gln Lys Ala
                835                 840                 845

Leu Glu Leu Glu Glu Phe Gln Tyr Ile Gly Glu Ser Gln Gly Tyr Asp
                850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
                900                 905                 910

Ala Glu Val Ile Ala Lys Asn Asn Ser Phe Val Asn Glu Ile Ile Ser
                915                 920                 925

Arg Ile Lys Val Thr Thr
        930

<210> SEQ ID NO 16
<211> LENGTH: 3145
<212> TYPE: DNA
<213> ORGANISM: Homo sapiens

<400> SEQUENCE: 16

```
ggcgggaaac agcttagtgg gtgtggggtc gcgcattttc ttcaaccagg aggtgaggag      60
gtttcgacat ggcggtgcag ccgaaggaga cgctgcagtt ggagagcgcg gccgaggtcg     120
gcttcgtgcg cttctttcag ggcatgccgg agaagccgac caccacagtg cgccttttcg     180
accgggcga cttctatacg gcgcacggcg aggacgcgct gctggccgcc cgggaggtgt      240
tcaagaccca gggggtgatc aagtacatgg ggccggcagg agcaaagaat ctgcagagtg     300
ttgtgcttag taaaatgaat tttgaatctt ttgtaaaaga tcttcttctg gttcgtcagt     360
atagagttga agtttataag aatagagctg aaataaggc atccaaggag aatgattggt      420
atttggcata taaggcttct cctggcaatc tctctcagtt tgaagacatt ctctttggta     480
acaatgatat gtcagcttcc attggtgttg tgggtgttaa aatgtccgca gttgatggcc     540
agagacaggt tggagttggg tatgtggatt ccatacagag gaaactagga ctgtgtgaat     600
tccctgataa tgatcagttc tccaatcttg aggctctcct catccagatt ggaccaaagg     660
aatgtgtttt acccggagga gagactgctg agacatggg gaaactgaga cagataattc      720
aaagaggagg aattctgatc acagaaagaa aaaaagctga cttttccaca aaagacattt     780
atcaggacct caaccggttg ttgaaaggca aaagggaga gcagatgaat agtgctgtat      840
tgccagaaat ggagaatcag gttgcagttt catcactgtc tgcggtaatc aagttttttag    900
aactcttatc agatgattcc aactttggac agtttgaact gactacttt gacttcagcc      960
agtatatgaa attggatatt gcagcagtca gagcccttaa ccttttttcag ggttctgttg   1020
aagataccac tggctctcag tctctggctg ccttgctgaa taagtgtaaa acccctcaag    1080
gacaaagact tgttaaccag tggattaagc agcctctcat ggataagaac agaatagagg    1140
agagattgaa tttagtggaa gcttttgtag aagatgcaga attgaggcag actttacaag    1200
aagatttact tcgtcgattc ccagatctta accgacttgc caagaagttt caaagacaag    1260
cagcaaactt acaagattgt taccgactct atcagggtat aaatcaacta cctaatgtta    1320
tacaggctct ggaaaaacat gaaggaaaac accagaaatt attgttggca gttttttgtga   1380
ctcctcttac tgatcttcgt tctgacttct ccaagtttca ggaaatgata gaaacaactt    1440
tagatatgga tcaggtggaa accatgaatt ccttgtaaa accttcattt gatcctaatc     1500
tcagtgaatt aagagaaata atgaatgact tggaaaagaa gatgcagtca acattaataa    1560
gtgcagccag agatcttggc ttggaccctg gcaaacagat taaactggat tccagtgcac    1620
agtttggata ttactttcgt gtaacctgta aggaagaaaa agtccttcgt aacaataaaa    1680
actttagtac tgtagatatc cagaagaatg gtgttaaatt taccaacagc aaattgactt    1740
ctttaaatga gagtatacc aaaaataaaa cagaatatga agaagcccag gatgccattg     1800
ttaaagaaat tgtcaatatt tcttcaggct atgtagaacc aatgcagaca ctcaatgatg    1860
tgttagctca gctagatgct gttgtcagct ttgctcacgt gtcaaatgga gcacctgttc    1920
catatgtacg accagccatt ttggagaaag gacaaggaag aattatatta aaagcatcca    1980
ggcatgcttg tgttgaagtt caagatgaaa ttgcatttat tcctaatgac gtatactttg   2040
aaaaagataa acagatgttc cacatcatta ctggccccaa tatgggaggt aaatcaacat    2100
atattcgaca aactggggtg atagtactca tggcccaaat tgggtgtttt gtgccatgtg    2160
agtcagcaga agtgtccatt gtggactgca tcttagcccg agtaggggct ggtgacagtc    2220
aattgaaagg agtctccacg ttcatggctg aaatgttgga aactgcttct atcctcaggt    2280
```

```
ctgcaaccaa agattcatta ataatcatag atgaattggg aagaggaact tctacctacg    2340
atggatttgg gttagcatgg gctatatcag aatacattgc aacaaagatt ggtgcttttt    2400
gcatgtttgc aacccatttt catgaactta ctgccttggc caatcagata ccaactgtta    2460
ataatctaca tgtcacagca ctcaccactg aagagacctt aactatgctt tatcaggtga    2520
agaaaggtgt ctgtgatcaa agttttggga ttcatgttgc agagcttgct aatttcccta    2580
agcatgtaat agagtgtgct aaacagaaag ccctggaact tgaggagttt cagtatattg    2640
gagaatcgca aggatatgat atcatggaac cagcagcaaa gaagtgctat ctggaaagag    2700
agcaaggtga aaaaattatt caggagttcc tgtccaaggt gaaacaaatg cccttactg     2760 aaatgtcaga agaaaacatc acaataaagt taaaacagct aaaagctgaa gtaatagcaa    2820
agaataatag ctttgtaaat gaatcattt cacgaataaa agttactacg tgaaaaatcc     2880
cagtaatgga atgaaggtaa tattgataag ctattgtctg taatagtttt atattgtttt    2940
atattaaccc ttttccata gtgttaactg tcagtgccca tgggctatca acttaataag    3000
atatttagta atattttact ttgaggacat tttcaaagat ttttattttg aaaaatgaga    3060
gctgtaactg aggactgttt gcaattgaca taggcaataa taagtgatgt gctgaatttt   3120
ataaataaaa tcatgtagtt tgtgg                                          3145
```

```
<210> SEQ ID NO 17
<211> LENGTH: 756
<212> TYPE: PRT
<213> ORGANISM: Homo sapiens

<400> SEQUENCE: 17
```

```
Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
            180                 185                 190

Ser Val Lys Lys Gln Gly Glu Thr Val Ala Asp Val Arg Thr Leu Pro
        195                 200                 205

Asn Ala Ser Thr Val Asp Asn Ile Arg Ser Ile Phe Gly Asn Ala Val
    210                 215                 220
```

```
Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
            245                 250                 255

Ile Phe Leu Leu Phe Ile Asn His Arg Leu Val Glu Ser Thr Ser Leu
                260                 265                 270

Arg Lys Ala Ile Glu Thr Val Tyr Ala Ala Tyr Leu Pro Lys Asn Thr
            275                 280                 285

His Pro Phe Leu Tyr Leu Ser Leu Glu Ile Ser Pro Gln Asn Val Asp
        290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
        355                 360                 365

Ser Ser Thr Ser Gly Ser Ser Asp Lys Val Tyr Ala His Gln Met Val
370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
        435                 440                 445

Gly Asp Thr Thr Lys Gly Thr Ser Glu Met Ser Glu Lys Arg Gly Pro
    450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
        515                 520                 525

Ser Phe Val Gly Cys Val Asn Pro Gln Trp Ala Leu Ala Gln His Gln
    530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
        595                 600                 605

Glu Tyr Ile Val Glu Phe Leu Lys Lys Lys Ala Glu Met Leu Ala Asp
    610                 615                 620

Tyr Phe Ser Leu Glu Ile Asp Glu Glu Gly Asn Leu Ile Gly Leu Pro
625                 630                 635                 640
```

```
Leu Leu Ile Asp Asn Tyr Val Pro Pro Leu Glu Gly Leu Pro Ile Phe
            645                 650                 655

Ile Leu Arg Leu Ala Thr Glu Val Asn Trp Asp Glu Lys Glu Cys
        660                 665                 670

Phe Glu Ser Leu Ser Lys Glu Cys Ala Met Phe Tyr Ser Ile Arg Lys
            675                 680                 685

Gln Tyr Ile Ser Glu Glu Ser Thr Leu Ser Gly Gln Gln Ser Glu Val
        690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
            740                 745                 750

Phe Glu Arg Cys
        755

<210> SEQ ID NO 18
<211> LENGTH: 2484
<212> TYPE: DNA
<213> ORGANISM: Homo sapiens

<400> SEQUENCE: 18
cttggctctt ctggcgccaa aatgtcgttc gtggcagggg ttattcggcg gctggacgag      60
acagtggtga accgcatcgc ggcggggaa gttatccagc ggccagctaa tgctatcaaa     120
gagatgattg agaactgttt agatgcaaaa tccacaagta ttcaagtgat tgttaaagag     180
ggaggcctga agttgattca gatccaagac aatggcaccg gatcaggaa agaagatctg     240 gatattgtat gtgaaaggtt cactactagt aaactgcagt cctttgagga tttagccagt     300
atttctacct atggctttcg aggtgaggct ttggccagca taagccatgt ggctcatgtt     360
actattacaa cgaaaacagc tgatggaaag tgtgcataca gagcaagtta ctcagatgga     420
aaactgaaag cccctcctaa accatgtgct ggcaatcaag ggacccagat cacggtggag     480
gacctttttt acaacatagc cacgaggaga aaagctttaa aaaatccaag tgaagaatat     540
gggaaaattt tggaagttgt tggcaggtat tcagtacaca atgcaggcat tagtttctca     600
gttaaaaaac aaggagagac agtagctgat gttaggacac tacccaatgc ctcaaccgtg     660
gacaatattc gctccatctt tggaaatgct gttagtcgag aactgataga aattggatgt     720
gaggataaaa ccctagcctt caaaatgaat ggttacatat ccaatgcaaa ctactcagtg     780
aagaagtgca tcttcttact cttcatcaac catcgtctgg tagaatcaac ttccttgaga     840
aaagccatag aaacagtgta tgcagcctat ttgcccaaaa acacacaccc attcctgtac     900
ctcagtttag aaatcagtcc ccagaatgtg gatgttaatg tgcaccccac aaagcatgaa     960
gttcacttcc tgcacgagga gagcatcctg agcgggtgc agcagcacat cgagagcaag    1020
ctcctgggct ccaattcctc caggatgtac ttcacccaga ctttgctacc aggacttgct    1080
ggcccctctg gggagatggt aaatccaca acaagtctga cctcgtcttc tacttctgga    1140
agtagtgata aggtctatgc ccaccagatg gttcgtacag attcccggga acagaagctt    1200
gatgcatttc tgcagcctct gagcaaaccc ctgtccagtc agcccaggc cattgtcaca    1260 gaggataaga cagatatttc tagtggcagg gctaggcagc aagatgagga gatgcttgaa    1320
ctcccagccc ctgctgaagt ggctgccaaa atcagagct ggaggggga tacaacaaag    1380 gggacttcag aaatgtcaga agagagga cctacttcca gcaaccccag aaagagacat    1440
```

```
cgggaagatt ctgatgtgga aatggtggaa gatgattccc gaaaggaaat gactgcagct   1500 tgtaccccc  ggagaaggat cattaacctc actagtgttt tgagtctcca ggaagaaatt   1560
aatgagcagg gacatgaggt tctccgggag atgttgcata accactcctt cgtgggctgt   1620
gtgaatcctc agtgggcctt ggcacagcat caaaccaagt tataccttct caacaccacc   1680
aagcttagtg aagaactgtt ctaccagata ctcatttatg attttgccaa ttttggtgtt   1740
ctcaggttat cggagccagc accgctcttt gaccttgcca tgcttgcctt agatagtcca   1800
gagagtggct ggacagagga agatggtccc aaagaaggac ttgctgaata cattgttgag   1860
tttctgaaga agaaggctga gatgcttgca gactatttct cttttggaaat tgatgaggaa   1920 gggaacctga ttggattacc ccttctgatt gacaactatg tgccccctttt ggagggactg   1980 cctatcttca ttcttcgact agccactgag gtgaattggg acgaagaaaa ggaatgtttt   2040
gaaagcctca gtaaagaatg cgctatgttc tattccatcc ggaagcagta catatctgag   2100
gagtcgaccc tctcaggcca gcagagtgaa gtgcctggct ccattccaaa ctcctggaag   2160
tggactgtgg aacacattgt ctataaagcc ttgcgctcac acattctgcc tcctaaacat   2220
ttcacagaag atggaaatat cctgcagctt gctaacctgc ctgatctata caaagtctttt   2280 gagaggtgtt aaatatggtt atttatgcac tgtgggatgt gttcttcttt ctctgtattc   2340
cgatacaaag tgttgtatca aagtgtgata tacaaagtgt accaacataa gtgttggtag   2400
cacttaagac ttatacttgc cttctgatag tattccttta tacacagtgg attgattata   2460
aataaataga tgtgtcttaa cata                                          2484
```

<210> SEQ ID NO 19
<211> LENGTH: 133
<212> TYPE: PRT
<213> ORGANISM: Homo sapiens

<400> SEQUENCE: 19

```
Met Glu Arg Ala Glu Ser Ser Thr Glu Pro Ala Lys Ala Ile Lys
1               5                   10                  15

Pro Ile Asp Arg Lys Ser Val His Gln Ile Cys Ser Gly Gln Val Val
                20                  25                  30

Leu Ser Leu Ser Thr Ala Val Lys Glu Leu Val Glu Asn Ser Leu Asp
            35                  40                  45

Ala Gly Ala Thr Asn Ile Asp Leu Lys Leu Lys Asp Tyr Gly Val Asp
        50                  55                  60

Leu Ile Glu Val Ser Asp Asn Gly Cys Gly Val Glu Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
                100                 105                 110

Ser Leu Cys Ala Leu Ser Asp Val Thr Ile Ser Thr Cys His Ala Ser
            115                 120                 125

Ala Lys Val Gly Thr
        130
```

<210> SEQ ID NO 20
<211> LENGTH: 426
<212> TYPE: DNA
<213> ORGANISM: Homo sapiens

<400> SEQUENCE: 20

```
cgaggcggat cgggtgttgc atccatggag cgagctgaga gctcgagtac agaacctgct    60
aaggccatca aacctattga tcggaagtca gtccatcaga tttgctctgg gcaggtggta   120
ctgagtctaa gcactgcggt aaaggagtta gtagaaaaca gtctggatgc tggtgccact   180
aatattgatc taaagcttaa ggactatgga gtggatctta ttgaagtttc agacaatgga   240
tgtggggtag aagaagaaaa cttcgaaggc ttaactctga acatcacac atctaagatt    300 caagagtttg ccgacctaac tcaggttgaa acttttggct tcggggggga agctctgagc   360
tcactttgtg cactgagcga tgtcaccatt tctacctgcc acgcatcggc gaaggttgga   420
acttga                                                              426
```

```
<210> SEQ ID NO 21
<211> LENGTH: 35
<212> TYPE: DNA
<213> ORGANISM: Artificial Sequence
<220> FEATURE:
<223> OTHER INFORMATION: Forward primer

<400> SEQUENCE: 21
gatcggatcc accatgggat ggagctgtat catcc                               35

<210> SEQ ID NO 22
<211> LENGTH: 49
<212> TYPE: DNA
<213> ORGANISM: Artificial Sequence
<220> FEATURE:
<223> OTHER INFORMATION: Reverse primer

<400> SEQUENCE: 22
ctgatctaga tcatttcccg ggagacaggg agaggctctt ctgcgtgta                49

<210> SEQ ID NO 23
<211> LENGTH: 37
<212> TYPE: DNA
<213> ORGANISM: Artificial Sequence
<220> FEATURE:
<223> OTHER INFORMATION: Reverse primer

<400> SEQUENCE: 23
ctgatctaga ttaacactct cccctgttga agctctt                             37

<210> SEQ ID NO 24
<211> LENGTH: 111
<212> TYPE: PRT
<213> ORGANISM: Artificial Sequence
<220> FEATURE:
<223> OTHER INFORMATION: Synthetic construct

<400> SEQUENCE: 24
```

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
            20                  25                  30

Ser Val Gly Asp Arg Val Thr Ile Thr Cys Ser Val Ser Ser Ser Ile
        35                  40                  45

Ser Ser Asn Asn Leu His Trp Tyr Gln Gln Lys Pro Ala Ala Ser Ser
    50                  55                  60

Gln Arg Thr Ser Pro Pro Thr Thr Ala Asn Ser Gly Val Val Thr Arg
65                  70                  75                  80

Thr Cys Thr Arg Ser Ala Lys Gly Pro Arg Trp Lys Ser Asn Glu Leu

```
                    85                  90                  95
Trp Leu His His Leu Ser Ser Ser Ser Arg His Leu Met Ser Ser
                100                 105                 110

<210> SEQ ID NO 25
<211> LENGTH: 605
<212> TYPE: DNA
<213> ORGANISM: Artificial Sequence
<220> FEATURE:
<223> OTHER INFORMATION: Oligonucleotide primer

<400> SEQUENCE: 25
atgggatgga gctgtatcat cctcttcttg gtagcaacag ctacaggtgt ccactccgac    60
atccagctga cccagagccc aagcagcctg agcgccagcg tgggtgacag agtgaccatc   120
acctgtagtg tcagctcaag tataagttcc aacaacttgc actggtacca gcagaagccc   180
gcagcctcca gccagaggac atcgccacct actactgcca acagtggagt agttacccgt   240
acatgtacac gttcggccaa gggaccaagg tggaaatcaa acgaactgtg gctgcaccat   300
ctgtcttcat cttcccgcca tctgatgagc agttgaaatc tggaactgcc tctgttgtgt   360
gcctgctgaa taacttctat cccagagagg ccaaagtaca gtggaaggtg gataacgccc   420
tccaatcggg taactcccag gagagtgtca cagagcagga cagcaaggac agcacctaca   480
gcctcagcag caccctgacg ctgagcaaag cagactacga gaaacacaaa gtctacgcct   540
gcgaagtcac ccatcagggc ctgagctcgc ccgtcacaaa gagcttcaac aggggagagt   600
gttaa                                                                605
```